US007014815B1

(12) United States Patent
Worthington et al.

(10) Patent No.: US 7,014,815 B1
(45) Date of Patent: Mar. 21, 2006

(54) TRACKABLE OPTICAL DISCS WITH CONCURRENTLY READABLE NONOPERATIONAL FEATURES

(75) Inventors: Mark O. Worthington, Tustin, CA (US); Jorma Virtanen, Irvine, CA (US)

(73) Assignees: Burstein Technologies, Inc., Delaware; Nagaoka & Co., Ltd., (JP)

( * ) Notice: Subject to any disclaimer, the term of this patent is extended or adjusted under 35 U.S.C. 154(b) by 0 days.

(21) Appl. No.: 09/311,329

(22) Filed: May 11, 1999

Related U.S. Application Data

(63) Continuation-in-part of application No. 09/183,842, filed on Oct. 30, 1998, now abandoned.

(51) Int. Cl.
    *G01N 21/29* (2006.01)
(52) U.S. Cl. .............................. 422/82.05; 369/124.07; 369/47.22; 369/103; 435/6; 435/287.2; 436/518
(58) Field of Classification Search ........... 369/124.07, 369/47.22, 275.1, 103; 435/6, 287.2; 436/518; 360/72.1, 75; 422/119, 82.05; 432/297
    See application file for complete search history.

(56) References Cited

U.S. PATENT DOCUMENTS

| 3,555,284 A | 1/1971 | Anderson |
| 3,966,322 A | 6/1976 | Greaves et al. |
| 4,478,768 A | 10/1984 | Takeoka et al. |
| 4,542,102 A | 9/1985 | Dattagupta et al. |
| 4,898,832 A | 2/1990 | Klose et al. |
| 5,281,540 A | 1/1994 | Merkh et al. |
| 5,310,523 A | 5/1994 | Smethers et al. |
| 5,413,939 A | 5/1995 | Gustafson et al. |
| 5,439,972 A | 8/1995 | Charles et al. |
| 5,453,969 A | 9/1995 | Psaltis et al. |
| 5,457,053 A | 10/1995 | Burd et al. |
| 5,508,985 A * | 4/1996 | Fairchild et al. ......... 369/47.22 |
| 5,537,373 A | 7/1996 | Horikiri |

(Continued)

FOREIGN PATENT DOCUMENTS

EP    0 504 432 A1    9/1992

(Continued)

*Primary Examiner*—Long V. Le
*Assistant Examiner*—Nelson Yang
(74) *Attorney, Agent, or Firm*—Knobbe, Martens, Olson & Bear, LLP

(57) ABSTRACT

Design, manufacture and use of optical discs that permit the concurrent and discriminable acquisition of signals from both operational features and nonoperational features is presented. The disc geometries and tracking schemes permit such discs to be read in, and data encoded by nonoperational features reported by, standard (or minimally-modified), optical disc readers. Single data layer first and second surface discs are described, as are multiple data layer discs. Use of the disks in analyte-specific assay is presented.

11 Claims, 40 Drawing Sheets

U.S. PATENT DOCUMENTS

| | | | |
|---|---|---|---|
| 5,580,790 | A | 12/1996 | Wall et al. |
| 5,755,942 | A | 5/1998 | Zanzucchi et al. |
| 5,781,526 | A | 7/1998 | Nishizawa et al. |
| 5,807,522 | A | 9/1998 | Brown et al. |
| 5,872,723 | A * | 2/1999 | DeCusatis et al. .......... 700/306 |
| 5,878,018 | A | 3/1999 | Moriya et al. |
| 5,909,422 | A | 6/1999 | Kamatani |
| 5,917,798 | A * | 6/1999 | Horimai et al. ............. 369/103 |
| 5,922,617 | A * | 7/1999 | Wang et al. ................ 436/518 |
| 5,932,799 | A | 8/1999 | Moles |
| 5,949,745 | A | 9/1999 | Kim |
| 6,055,218 | A | 4/2000 | Takeda et al. |
| 6,287,517 | B1 | 9/2001 | Ackley et al. |
| 6,391,625 | B1 * | 5/2002 | Park et al. ............... 435/287.2 |
| 2002/0058242 | A1 | 5/2002 | Demers |
| 2002/0071362 | A1 | 6/2002 | Worthington |
| 2002/0097658 | A1 | 7/2002 | Worthington et al. |
| 2002/0145960 | A1 | 10/2002 | Worthington et al. |
| 2002/0177144 | A1 | 11/2002 | Remacle et al. |
| 2003/0003464 | A1 | 1/2003 | Phan et al. |
| 2003/0054376 | A1 | 3/2003 | Mullis et al. |

FOREIGN PATENT DOCUMENTS

| | | |
|---|---|---|
| WO | WO 96/35940 | 11/1996 |
| WO | WO9705609 | 2/1997 |
| WO | WO 00/05582 | 2/2000 |
| WO | WO 01/47638 A2 | 7/2001 |

* cited by examiner 20 femtomoles 20 attomoles 20 zeptomoles

FIG. 41A

| AWM Muri | Supplementary sheet, mold acceptance test | | | | | CD-3-AWM |
|---|---|---|---|---|---|---|
| Job No | 36-10236 | Agent | CR-R | Ram hold | vac + mech | IFPI — |
| SM Order No | 9N.96293 | Customer | Eximpo CS | Ram dia. | 24 | Product Code No. 256 |

Dimensions

| | 0° | 90° | 180° | 270° | | |
|---|---|---|---|---|---|---|
| 0'=mold at top | R15 | 1.15 | 1.15 | 1.15 | 1.15 | mm |
| Thickness | R40 | 1.155 | 1.155 | 1.155 | 1.155 | mm |

Center hole 15.05+/−0.3    15.05    Drm. 120+/−0.3___ mm

Weight in g

| | | Min | 0 | 15 | 30 | 45 | 60 |
|---|---|---|---|---|---|---|---|
| Measure every 15 min. during test | g | | 15.26 | 15.27 | 15.26 | 15.26 | 15.26 |
| Max. diff±0.1 g | g | | | 15.26 | 15.26 | 15.26 | 15.26 |

Water in mold

| | ACTUAL | DESIRED | Tol. |
|---|---|---|---|
| Sprue bush | 9 ltr./Min. | 7 | −1/+3 |
| Embosser | 6 ltr./MIN. | 7 | −1/+3 |

Vacuum   without   with   diff.   tol.

| Handling | bar | | |
| Ram | bar | | |

Mold Function

Raw material
Embosser ✓            Makrolon 2005 ✓
Sprue ejector ✓       Lexan 1020
Ejector sleeve ✓      Panlite 5503
Sprue bush ✓

Air outlet

FS dia. ✓
BS dia. ✓

Visual faults

| Streaks | 1/4 | Center hole ✓ |
| | 1/4 | Stacking groove ✓ |
| | 1/4 | Info ✓ |
| | 1/2 | ✓ |
| Clouds | 1 | ✓ |
| Voids | 3 | ✓ |
| Black dots | 3 | ✓ |
| Matt outer edge | 3 | ✓ |
| Burrs | 3 | Center hole ✓ |
| | 3 | Outer Edge ✓ |
| Scratches | 3 | |
| Diesel effect | 3 | |
| Brown Discoloration | 5 | |

Molding compound cold

| Thickness of cavity (3) | 1.462 |
| Venting gap (5) | 0.33 |
| Position of embosser (9) | 0.876 |
| Position of spure bush (10) | 0.162 |
| Embossing stroke | 0.7 |

Measuring means

1. Polarized light
2. Halogen light
3. Neon Light
4. Black (UV Light)
5. White paper
6. Micrometer
7. Balance

| 01.01 Mold movement | | | | | |
|---|---|---|---|---|---|
| Closing movement | V33 =100% | Closing time | S33 | = | 019.0mm |
| | V34 =100% | | S34 | = | 000.7mm |
| Pressure initiation | | | T32 | = | 000. |
| Opening movement | V41 =100% | Opening time | S41 | = | 055.0mm |
| Braking | V42 =010% | | | | |
| | | | T36 | = | 000. |
| Pause time | T40 =000.000s | Mold position | S640 | = | 075. |
| Mold closing pressures | | | | | |
| Closing pressure | P682 =085% | | | | |
| Pressure Build-up | P681 =020% | T681 | = | 000.10s | |
| | C608 = 0 | Switched off | | | |

| 02.01 Summary of mold auxiliary controls/robotics | | | | | |
|---|---|---|---|---|---|
| Enable removal | T680 = 0065.0 | | | | |
| Delays | | | | | |
| Blow off sprue | T602 = 000.03 | Sprue blowing time | T603 | = | 000.1 |
| Advance ejector pin | T53 = 000.10s | | | | |
| Transfer stroke forward | T55 = 000.12s | | | | |
| Transfer Stroke return | T56 = 000.15s | Extend removal | T668 | = | 000.2 |
| Embosser forward | T62 = 001.20s | Embosser return | T63 | = | 000.1 |
| Blow on nozzle side | T75 = 000.50s | Nozzle side blowing time | T74 | = | 000.8 |
| Blow on moving side | T671 = 000.00 | Moving side blowing time | T71 | = | 000.1 |
| Unit Forward | T680 = 000.70s | | | | |
| Starting program | C683 = 00000 | T683 | = | 000.00s | S683 | = | 0004. |
| Cyle time | T11 = 009.05s | | | | |
| Removal time | T640 = 000.70s | | | | |

| 03.01 Metering | | | | | | | | |
|---|---|---|---|---|---|---|---|---|
| Screw retraction | C17 | = | 0 | Switched off | | | | |
| Metering Delay | T20 | = | 000.50 s | Metering time | T21 | = | 005.9 | |
| Metering stages | C124 | = | 2 | | | | | |
| Metering end point | S23 | = | 026.0 mm | P23 | = | 0060 bar | N23 = 100 l. | |
| | S24 | = | 029.0 mm | P24 | = | 0010 bar | N24 = 020 l. | |
| Holding pressure | P27 | = | 0010 bar | Start of injection | | | S0 = 029.0 | |

| 04.01 Injection | | | | | | | | |
|---|---|---|---|---|---|---|---|---|
| Enable injection | S682 | = | 0002.0 mm | Screw position | | | S641 = 029.0 | |
| Injection values | C121 | = | 10 | Start of injection | | | S0 = 029.0 | |
| | V196 | = | 0050 mm/s | S196 | = | 030.0 mm | | |
| | V197 | = | 0062 mm/s | S197 | = | 027.6 mm | | |
| | V198 | = | 0085 mm/s | S198 | = | 025.6 mm | | |
| | V199 | = | 0115 mm/s | S199 | = | 024.0 mm | | |
| | V200 | = | 0120 mm/s | S200 | = | 019.8 mm | | |
| | V201 | = | 0110 mm/s | S201 | = | 016.2 mm | | |
| | V202 | = | 0085 mm/s | S202 | = | 009.5 mm | | |
| | V203 | = | 0065 mm/s | S203 | = | 008.0 mm | | |
| | V204 | = | 0040 mm/s | S204 | = | 004.0 mm | | |
| | V205 | = | 0025 mm/s | S205 | = | 001.5 mm | T2 = 000.3 | |
| Enable V/P changeover | | | | V/P changeover point | | | S11 = 004.0 | |
| Forcible changeover | | | | | | | | |
| Flow number | S121 | = | 018.2 mm | S122 | = | 015.0 mm | C125 = 2776 | |
| Pressure monitoring | | | | Peak pressure | | | P125 = 01044 | |
| First stage | P101 | = | 01300 bar | T201 | = | 00.02 s | | |
| Second stage | P102 | = | 01100 bar | T201 | = | 00.02 s | S102 = 006.0 | |

FIG. 41E

| 04.02 Holding pressure, cooling | | | | | | |
|---|---|---|---|---|---|---|
| Holding pressure values | C122 | = | 04 | Changeover point | S11 = | 004.0 |
| | P12 | = | 00550 bar | | | |
| | P117 | = | 00420 bar | T117 = | 000.20 | |
| | P118 | = | 00380 bar | T118 = | 000.40 | |
| | P119 | = | 00200 bar | T119 = | 000.90 | |
| | | | | T120 = | 002.00 | |
| Holding pressure time | | | | | | |
| Cooling time | T39 | = | 005.30 s | | | |
| Melt cushion monitoring | | | | Melt cushion | S19 = | 003.7 |
| Upper limit | S219 | = | 010.0 MM | Lower limit | S119 = | 000.5 |

| 05.01 Nozzles, unit, purging/dry cycles | | | | | | |
|---|---|---|---|---|---|---|
| Standstill monitoring | C606 | = | 60 min | C640 = | 0004 min | |
| Unit | | | | | | |
| Unit forward | T680 | = | 000.70 s | V29 = | 030 % | |
| Lift | T30 | = | 000.30 s | V30 = | 050 % | |
| Unit set-up and manual movements | | | | | | |
| Move forward | V815 | = | 030 % | Lift V806 = | 030 % | |
| Purge/dry cycle/clean | | | | | | |
| Number of metering strokes | C16 | = | 20 | C201 = | 50 | |
| Metering | S16 | = | 028.0 mm | P16 = | 0060 bar | N16 = 200 |
| Injection | S18 | = | 001.5 mm | V101 = | 05 mm/s | |
| Delay for purging | T606 | = | 000.00 s | | | |

06.01 Temperature control, plastifier zones/temperature control devices

| Zone/description | Set point | Actual value | Reduced Tolerance | | | Heating outputs | Cooling |
|---|---|---|---|---|---|---|---|
| | | | | minus | plus | | |
| 10 Melt temperature | 310° C | 305° C | 180° C | 040° C | 040° C | 014% | |
| 30 Nozzle | 330° C | 330° C | 180° C | | 040° C | 025% | |
| 13 Nozzle | 315° C | 315° C | 180° C | 040° C | 040° C | 008% | |
| Cylinder head | 310° C | 310° C | 180° C | 040° C | 040° C | 005% | |
| 15 Compression | 305° C | 305° C | 180° C | 040° C | 040° C | 006% | |
| 16 Compression | 305° C | 308° C | 180° C | 040° C | 040° C | 070% | |
| 18 Feed | 300° C | 295° C | 180° C | 040° C | 040° C | | |
| 20 Inlet | 060° C | 060° C | 060° C | 040° C | 040° C | | 024 |

| Zone/description | Set point | Actual value | Reduced Tolerance | | | Heating outputs | Cooling |
|---|---|---|---|---|---|---|---|
| | | | | minus | plus | | |
| 24 Heating/cooling device | 112° C | 093° C | 050° C | 020° C | 020° C | 000% | 000 |
| 25 Heating/cooling device | 114° C | 091° C | 050° C | 040° C | 020° C | 000% | 000 |

08.01 Disk transfer

| Peripheral interface | C684 = | 0 | Without signal acknowledgement | | |
|---|---|---|---|---|---|
| Buffer switch-off size | C680 = | 65000 | | | |
| Production delay | T682 = | 001.00 s | C605 = | 0 | With interruption of cycle |
| Max. transfer time | T601 = | 001.00 s | | | |

FIG. 41F

| 09.01 Production control | | | | | | | |
|---|---|---|---|---|---|---|---|
| Application | C340 = | 2 | | No application | | | |
| Data set number | C315 = | 100 | | | | | |
| Production sequence | | | | | | | |
| | | | | Piece counter | C324 = | 29270 | |
| Item number | C303 = | 1 | | Cycle counter | C325 = | 29270 | |
| Cycle time | T11 = | 009.05 s | | Failure rate | C718 = | 30.56% | |
| Production preperation | | | | Reason | C357 = | 00 | |

| 10.01 Process statistics | | | | | | | |
|---|---|---|---|---|---|---|---|
| Q monitoring | C340 = | 2 | | Monitoring without screenning out | | | |
| Q report | C700 = | 0 | | No report | | | |
| | cycles of which | | | out of tolerance | | failure rate | |
| Total | C325 = | 29270 | | C318 = 8946 | | C718 = | 30.56% |
| Random sample | C326 = | 29269 | | C338 = 8946 | | C738 = | 30.56% |

| Process variables | Set Point x | Tolerance +/- | Actual Value x | Mean xq | Scatter 3s | Out of Tolerance |
|---|---|---|---|---|---|---|
| Metering time | 1.20 | 0.30 | 5.98 s | 2.32 | 5.408 | -06786 |
| Injection start | 30.1 | 2.0 | 29.0 mm | 28.6 | 0.82 | 2028 |
| Injection time | 0.47 | 0.20 | 0.33s | 0.39 | 0.105 | 0 |
| V/P changeover point | 3.5 | 1.0 | 4.0 mm | 4.0 | 0.04 | 0 |
| Melt cushion | 4.2 | 1.0 | 3.7 mm | 3.8 | 0.25 | 0 |
| ? peak value | 600 | 200 | 871 bar | 682 | 99.9 | -06566 |
| ? peak value | 0 | | 0 bar | 0 | 0.0 | 0 |
| Flow number | 2500 | 300 | 2776 | 2441 | 99.9 | 359 |
| Cycle time | 3.90 | 0.50 | 9.05 s | 5.08 | 6.421 | -06570 |

FIG. 41G 10.02 Configuration of the quality monitoring

Reaction: Process data outside tolerance
Switch-off behavior  C703=0   no reaction

FIG. 41H 10.03 Q report intermediate store

Manufacturer
Machine No.    DVD_F50
Job data 16.01 System characteristics

Machine data
Machine type            DISCJET 600/110     Order number    DVD_F50
Control version         PAC 13.54            IMC 12.26       CEL 10.31
Database version        DB 05.80             Date created    23.10.1996
Special                 350400               Version         17106

Mold data
Installed height        S90 = 160 mm

Plasticizing                   Identification   C806 =              024         Max metering stroke         C804 =    00⁚
Ram nominal diameter            S801          = 032.0 mm                                                     S802 =   100.⌐
Max. permissible melt pressure  PB00=01482 bar                                   Max. specific melt pressure P802 =  01482 bar
Max. permissible backpressure   P801          = 0317 bar Temperatures            Set point/actual value             Tolerance -/+            Heating          Cooling
Cabinet                 TH1 = 035  026° C                  030° C   010° C           000%             005
Oil                     TH2 = 050  051° C                  041° C   011° C

FIG. 41I

TRACKABLE OPTICAL DISCS WITH CONCURRENTLY READABLE NONOPERATIONAL FEATURES

CROSS-REFERENCE TO RELATED APPLICATIONS

This application is a continuation-in-part-of co-owned and application Ser. No. 09/183,842, filed Oct. 30, 1998, now abandoned, of which is incorporated herein by reference.

FIELD OF THE INVENTION

The present invention relates to the design, manufacture and use of optical discs and optical disk readers and writers. Specifically, the invention relates to the design, manufacture and use of optical discs that permit the concurrent and discriminable acquisition of signals from nonoperational features of the disc, such as analyte-specific signal elements, and from operational features of the disc, such as tracking attributes.

BACKGROUND OF THE INVENTION

Over the past decade, scanning confocal laser microscopy (SCLM) has revolutionized life science imaging. In scanning confocal laser microscopy, laser light is scanned across a specimen at a precisely chosen focal plane. Light reflected back from the specimen is collected, excluding light from all but the specifically-illuminated confocal plane. By excluding light reflected from all but the chosen image plane, glare is eliminated, producing crisp sectional images from full-thickness, unfixed tissues and cells. In addition, the reproducible spatial precision of the computer-driven scanning process permits the exact spatial registration of the individually-acquired sectional images, allowing the tomographic reconstruction of a three-dimensional image by overlay of the severally-acquired sectional images. Wiesendanger, *Scanning Probe Microscopy and Spectroscopy: Methods and Applications*, Cambridge Univ. Press (July 1995); Cullander, *J. Investig. Dermatol. Symp. Proc.* 3:166–171 (1998); Paddock, *Proc. Soc. Exp. Biol. Med.* 213:24–31 (1996); Ockleford, *J. Pathol.* 176:1–2 (1995); Laurent et al., *Biol. Cell.* 80:229–240 (1994).

The use of laser-excitable fluorescent dyes and proteins as ligand-specific probes has permitted scanning laser microscopy to be adapted beyond standard cell and tissue imaging to a wide variety of assays. Thus, laser scanning cytometers have proven particularly useful in fluorescence-based cytometric assays of cell cycle events. Juan et al., *Methods Mol. Biol.*, 91: 67–75 (1996); Juan et al., *Cell Biol.* 2: 261–273 (1998); Juan et al., *Cell Biol.* 2: 341–350 (1998); Clatch et al., *Cytometry* 34: 36–38 (1998); Luther et al., *Microscopy & Microanalysis*, 3: 235–236 (1997).

Ashby et al., U.S. Pat. No. 5,549,588, describes scanning laser microscopic assay of "genome reporter matrices." In these genome reporter matrices, each element of a spatially-addressable matrix contains cells in which expression of a common fluorescent reporter is driven from a distinct transcriptional regulatory element. The strength of the fluorescence signal acquired during scanning identifies the level of gene expression driven by each spatially-identifiable transcriptional regulatory element.

Scanning laser microscopy has also been adapted to scanning of nucleic acid microarrays built on silicon chips, Lashkari et al., *Proc. Natl. Acad. Sci. USA* 94: 13057–62 (1997); DeRisi et al., *Science*, 278:680–86 (1997); Wodicka et al., *Nature Biotechnology*, 15:1359–67 (1997); to measurement of ionic fluxes in cells, Schild, Cell. *Calcium* 19:281–296 (1996); Turner et al., *J. Investig. Dermatol. Symp. Proc.* 3:136–142 (1998); and to measurement of the subcellular distribution of various cellular components, Takubo et al., *Haematologica* 82:643–647 (1997).

Yet each of these applications of SCLM demands a specialized piece of computer-controlled optical equipment. There thus exists a need in the art for an inexpensive generic device that permits computer-driven confocal laser scanning of a microscopic sample.

The minimum mechanical requirements for such a device—laser, focusing and detection optics, precision scanning means, and computer interface—may all be found in standard optical disc readers or writers. Optical disc reader/writers, such as for CD and DVD, focus light from a solid state laser on a surface of a spinning disc and scan the disc to detect information that is encoded digitally in spatially-addressable patterns of submicron features.

Adaptation of optical discs and optical disc readers/writers to scanning microscopic applications would present marked advantages over existing approaches. Principal among these are availability and cost. The worldwide installed base of CD and DVD-ROM readers is estimated at present to be about 300 million units, and is expected within the next 5 years to rise to over 500 million units. *Optical Publishing Industry Assessment*, 9th ed. (Infotech, Inc., Woodstock, Vt.) (1998). The devices are inexpensive, reliable, and ubiquitous.

Other advantages of using optical discs for detection and characterization of microscopic structures are discussed in WO 96/09548 (Gordon), EP A 392475 (Idemitsu), EP A 417 305 (Idemitsu), EP A 504432 (Idemitsu), WO 98/28623 (Gamera), and WO 98/12559 (Demers), all of which are incorporated herein by reference. Further advantages are set forth in co-owned and copending U.S. patent applications Ser. No. 08/888.935, filed Jul. 7, 1997, Ser. No. 09/064,636, filed Apr. 21, 1998, Ser. No. 09/120,049 filed Jul. 21, 1998, and counterpart international applications published as WO 98/38510, Wo 98/38510 and WO 98/01533, the disclosures of which are incorporated herein by reference. There thus exists a need in the art for means to adapt optical disc readers to scanning laser microscopic applications.

Although optical disc readers possess the mechanical prerequisites for effective confocal laser microscopic scanning, operational requirements of existing disc readers present significant impediments to the successful detection and characterization of microscopic structures disposed upon the surface of an optical disc.

There are at least four basic operational requirements that must be satisfied for an optical drive correctly to read and decode the data present within an optical disc: the reader must focus correctly on the disc plane encoding the data, it must control the radial positioning of its optical pickup, it must control the tangential positioning of its optical pickup, and it must control the speed of disc rotation. The most common optical disc systems use elements of the optical medium itself to satisfy at least some of these requirements.

Thus, in a typical pressed CD, the disc substrate is impressed with a spiral track made up of a series of embossed pits, the signals from which are used by the optical disc reader to maintain proper focus and tracking. In CD-R, the data-encoding dye marks written by the user provide the requisite tracking features during subsequent reading. More generally, in each of the existing optical disc standards, the features used to encode data serve simultaneously to provide operational signals that the reader requires to control its operations. Although efficient, such standards make no provision for acquiring data from nonoperational features disposed upon the disk.

For example, because the tracking features are obligately embedded within the data layer of the disk, structures applied to the laser-proximal surface of the disc may interfere with detection of such operational features, and thus interfere with correct operation of the reader. Furthermore, such nonoperational structures may lie sufficiently outside the focal plane of the disc's operational features as to prevent their concurrent and discriminable detection by the reader's optical pickup.

One solution to this problem is to use nonstandard drives. One such proposed drive uses two optical pickups, one to detect tracking information, the other to detect surface structures, EP A 417 305 (Idemitsu). However, such modification moots a principal advantage of using optical disc readers for laser microscopic detection, which is the ecumenical distribution of such devices.

There thus exists a need in the art for optical discs that permit a standard optical disc reader/writer to acquire signals from nonoperational features of the disc, such as analyte-specific signal elements disposed thereon, concurrently and discriminably with signals generated by operational features of the disk, such as tracking attributes.

SUMMARY OF THE INVENTION

The present invention solves these and other problems in the art by providing optical discs, optical disk designs and geometries, including optical disc tracking schemes, and optical disk drive modifications that permit disc tracking signals to be acquired concurrently with and discriminated from signals generated by nonoperational features, including analyte-specific signal elements, that are disposed upon a surface of the optical disc.

We have found that the physical orientation of standard, single data-layer, CD-type optical discs may effectively be inverted, presenting what would otherwise be a laser-distal surface as the laser-proximal first surface of the disc. To compensate for the inverted physical orientation, an inverted image of the disc's operational features, particularly the disc's tracking features, is engineered into the disc.

We have also found that radial-plane tracking schemes, such as a wobble groove, that rely substantially on perturbations in the radial plane of the disc, may advantageously be used on such inverted discs (albeit compensatingly inverted), to segregate the tracking signal from the quad sum (HF, RF) signal, thus permitting the quad sum signal to be used to detect signals from nonoperational features, including analyte-specific signals.

We have demonstrated, using these approaches, that micron-sized nonoperational features—in particular, small analyte-specific signal elements— that are disposed upon the air-incident reflective first surface of such discs may be detected, measured, and characterized by an optical disc drive. We have also demonstrated that such nonoperational features may be detected when the reflective surface is presented as the second surface of the disc by attachment to the disk of a laser-refracting laser-proximal cover.

The operational features of the disc, including tracking features, may be detected concurrently with and readily discriminated from nonoperational, yet data-encoding, features, such as analyte-specific signal elements. The signals from the nonoperational features, exemplified herein by analyte-specific signals, appear as high amplitude, high frequency events in the optical disc reader's quad sum (HF, RF) signal. The signals generated by the nonoperational features provide dimensional information about the nonoperational feature, and may be distinguished from those generated by operational features in real time or subsequent to data acquisition.

The examples presented herein demonstrate that immunoassays for small molecule analytes and nucleic acid hybridization assays of high sensitivity may readily be adapted to detection using this system;) we have also demonstrated that counting and analysis of blood cells is also readily accomplished. Thus, we have demonstrated that standard clinical and research assays may readily be adapted to detection, measurement, and characterization by optical disk drives during trackable scanning an optical disk.

In a first aspect, therefore, the invention provides a trackable optical disc having readable nonoperational data, comprising: a first reflective surface having an attribute trackable by an optical disc reader; and a data-encoding nonoperational feature disposed readably with the trackable attribute. In preferred embodiments of this first aspect of the invention, the nonoperational feature and trackable attribute are readable by the same optical pickup (objective assembly). The nonoperational feature and trackable attribute may be concurrently readable, often by the same optical pickup. Typically, in such single data layer, first surface discs, the nonoperational feature is disposed confocally with the trackable attribute.

In preferred embodiments of this first aspect of the invention, the signal from the nonoperational feature is detectable as an amplitude variation in the HF signal, and the duration of the nonoperational signal provides a substantially quantitative measure of the size of the nonoperational feature in the direction of disc tracking.

The first surface, single data layer embodiments may further comprise a first solid substrate having a laser-distal side and a laser-proximal side, wherein both the first reflective surface and the trackable attribute are disposed upon the laser-proximal side of the first solid substrate. In some embodiments, the nonoperational feature is disposed on the laser-proximal side of the first reflective surface of said disc substrate. Alternatively, the nonoperational feature is disposed upon the laser-proximal side of a light transmissible coating applied to the laser-proximal surface of the first reflective surface.

Preferred trackable attributes are attributes that are disposed radially; most preferred, at present, is a wobble groove. In some embodiments, the trackable attribute is physically engineered into the disk. In alternative embodiments, the first reflective surface holographically projects a readable image of the trackable attribute, such as a wobble groove, when illuminated. The holographic image may be projected laser-proximal to the first reflective surface, and is preferably projected confocally to the nonoperational feature.

In the aforementioned embodiments, presentation of the reflective surface as the first surface of the disc eliminates the focusing effects of the air-incident, laser-refractive layer that is typical of a standard disc. In another aspect, therefore, the present invention provides an optical disc assembly having readable nonoperational data, comprising: a trackable optical disc and a laser-refracting cover, wherein the cover further focuses the laser of the optical disc reader on the disc's first reflective surface. The disc is constructed in accordance with the aforementioned principles, and thus the nonoperational feature is preferably disposed confocally with the disc's tracking attribute, which is, in preferred embodiments, a wobble groove.

The cover may be is nonintegral to the disc and attachable—permanently or reversibly—thereto. Alternatively, the cover may be integral to the disc and moveably attached, such as hingeably attached. The cover must be appropriately laser refracting, and in preferred embodiments consists essentially of a material selected from the group consisting of plastic and glass, preferably plastic. Among plastics usefully employed in manufacture of the cover are polycarbonate and polystyrene. Assembled, the optical disc assembly preferably approximates the dimensions of a unitary disc, with radial diameter between 110–130 mm (or 75–85 mm) and a depth between 1.1–1.3 mm.

Significant advantages may attend disposition of the data-encoding nonoperational features on the cover of such a disk assembly; in such embodiments, the nonoperational feature is disposed upon the laser-distal side of the cover, preferably in such location as to be rendered confocal with the disc's trackable attributes after attachment to the disc. In yet another aspect, the laser-refracting cover may be provided packaged in a kit with a disc of the present invention.

Digital versatile disc (digital video disk; DVD) physical and logical standards may also usefully be employed in the practice of the single data layer embodiments of the present invention. In another aspect, therefore, the present invention provides single data layer trackable discs with data-encoding nonoperational features and that accord with DVD standards, such as the ZCLV tracking format.

The DVD format also provides for multiple data layer discs, which prove particularly well-suited to concurrent, discriminable acquisition of tracking and nonoperational signals. In particular, the existence of multiple data layers within the DVD discs and the concomitant dual-focus of DVD readers permit the plane occupied by the operational features of the disc—particularly tracking features—to be segregated physically from the plane occupied by data encoding nonoperational features, facilitating concurrent discriminable acquisition of both types of data.

In another aspect, therefore, the present invention provides a trackable optical disc having readable nonoperational data, comprising: a first reflective surface; a second reflective surface; and a data-encoding nonoperational feature, wherein the first or second reflective surface has an attribute trackable by an optical disc reader and the nonoperational feature is disposed readably with the trackable attribute. In some embodiments of this aspect of the invention, the nonoperational feature and trackable attribute are readable by the same optical pickup (objective assembly). In some embodiments, the nonoperational feature is readable concurrently with the trackable attribute.

The multiple data layer embodiments may further comprise a first solid substrate and a second solid substrate, each having a laser-distal side and a laser-proximal side, the first reflective surface disposed upon the laser-proximal side of said first solid substrate, the semireflective surface disposed upon the laser-distal side of said second solid substrate, the second solid substrate and semireflective surface both being laser-proximal to the first solid substrate and first reflective surface. In some embodiments, the nonoperational feature is disposed confocally with the semireflective surface, typically on the laser-distal side of the semireflective surface. In other embodiments, the nonoperational feature is disposed confocally with the first reflective surface, typically on the laser-proximal side of the reflective surface. In some embodiments, the nonoperational feature will be disposed between the first reflective surface and the semireflective surface.

In the multiple data layer embodiments, the trackable attribute may, as with single data layer embodiments, include a wobble groove, and the nonoperational feature may be disposed confocally with the wobble groove.

In another aspect, the invention provides a trackable optical disc system, comprising a trackable optical disc or disc assembly, as above-described, and an optical disc reader, and may further comprise a display, with or without intermediation of a digital computer.

In another aspect, the invention provides methods of making the trackable discs of the present invention. Thus, the invention provides a method of making a trackable optical disc having readable nonoperational data, comprising the step of: disposing a data-encoding nonoperational feature on an optical disc readably with a trackable attribute of the disc. In preferred embodiments, the nonoperational feature is disposed confocally with the trackable attribute, and the trackable attribute typical includes a wobble groove.

The invention also provides, in a related aspect, a method of making a trackable optical disc assembly having readable nonoperational data, comprising the steps of: disposing a data-encoding nonoperational feature on the laser-distal side of a laser-refracting cover; and attaching the cover to a disc comprising a first reflective surface having an attribute trackable by an optical disc reader; wherein the data-encoding nonoperational feature is readable with the tracking attribute when the cover is attached to said disc.

In a further aspect, the invention provides a method of using an optical disc reader to read data encoded in a nonoperational feature of a disc, comprising the step of: trackably reading an optical disc constructed as above-described. In the embodiments demonstrated herein, the data are detectable in the optical disc reader's HF signal, and the data includes dimensional information about the nonoperational feature.

In yet another aspect, the present invention provides a method of segregating tracking signals from signals generated by readable nonoperational features disposed upon an optical disc, comprising: disposing the nonoperational feature confocally with a trackable attribute that produces minimal variation in the HF signal during trackable reading of the optical disc. In preferred embodiments of this aspect of the invention, the trackable attribute includes a wobble groove.

A myriad of nonoperational features that encode useful data may be disposed upon the trackable optical discs of the present invention. Among such useful nonoperational features are analyte-specific signal elements. Thus, the invention further provides trackable discs, trackable disc assemblies, and methods of making and using the same for analyte-specific assay.

In a first such aspect, therefore, the invention provides a single data layer trackable optical disc for analyte-specific assay. The disc comprises a first reflective surface having an attribute (alternatively denominated a "feature") that is trackable by an optical disc reader, and at least one analyte-specific signal element disposed readably with this trackable attribute. In a preferred embodiment, the analyte-specific disc has a first solid substrate with a laser-distal and laser-proximal side; the substrate has impressed upon its laser-proximal side a wobble groove forming a spiral track; the first reflective surface is disposed upon the laser-proximal side of the solid substrate; and at least one analyte-specific signal element is disposed confocally with the wobble groove.

In one embodiment, the analyte-specific signal elements are disposed directly upon the laser-proximal reflective surface of the disc. In an especially preferred embodiment, the analyte-specific signal elements are disposed substantially within the wobble groove. In an alternative embodiment, the analyte-specific signal element is disposed upon the laser-proximal side of a light transmissible coating applied to the laser-proximal surface of the first reflective surface, confocally with the disk's tracking features.

In these embodiments, the signal from the analyte-specific signal elements is preferably detectable as a variation in the amplitude of the HF signal, and the duration of analyte-specific signal provides a substantially quantitative measure of the size of the analyte-specific signal element in the direction of disc tracking.

In another series of embodiments of the single data layer discs of the present invention, the operational features of the disc—particularly tracking features—are encoded in a reflective hologram rather than through physical impression in the disc substrate. Thus, the invention provides an analyte-specific trackable optical disc in which the first reflective surface holographically projects a readable image of the trackable attribute when the surface is illuminated by incident laser light. In preferred embodiments, the holographic image is projected laser-proximal to the physical plane of the hologram, and is most preferably projected in a plane substantially confocal with the analyte-specific signal elements. In an especially preferred embodiment, the projected tracking attribute is an image of a wobble groove.

In the aforementioned embodiments, presentation of the reflective surface as the first surface of the disc eliminates the focusing effects of the air-incident, laser-refractive layer that is typical of a standard disc. In another aspect, therefore, the present invention provides an optical disc assembly for analyte-specific assay, the assembly comprising a trackable analyte-specific optical disc and a laser-refracting cover, wherein the cover further focuses the laser of said optical disc reader on the disc's first reflective surface. In one set of embodiments, the cover is moveably attached to the disc; in another set of embodiments, the cover is nonintegral to the disc and is attachable thereto. For the nonintegral covers, the invention further provides a kit in which an analyte-specific trackable optical disc and a nonintegral laser-refracting cover are packaged together.

The laser-refracting cover may consist essentially of glass or plastic, with polystyrene and polycarbonate at present preferred. In some embodiments, the analyte-specific signal elements are disposed upon the laser distal (disk-proximal) surface of the cover, which places the signal elements confocal with the disk's operational features when assembled to the disk.

Digital versatile disc (digital video disk; DVD) physical and logical standards may also usefully be employed in the practice of the single data layer embodiments of the present invention. In another aspect, therefore, the present invention provides single data layer analyte-specific discs with trackable attributes that accord with DVD standards, such as the ZCLV tracking format.

The DVD format also provides for multiple data layer discs, which prove particularly well-suited to concurrent, discriminable acquisition of tracking and analyte-specific signals. In particular, the existence of multiple data layers within the DVD discs and the concomitant dual-focus of DVD readers permit the plane occupied by the operational features of the disc—particularly tracking features—to be segregated physically from the plane occupied by analyte-specific elements, facilitating concurrent discriminable acquisition of both types of data.

In another aspect, therefore, the present invention provides analyte-specific trackable optical discs that comprise a first reflective surface, a second reflective surface, and at least one analyte-specific signal element; the first or second reflective surface has an attribute trackable by an optical disc reader, and the analyte-specific signal element is disposed readably with the trackable attribute.

In preferred embodiments of the multiple data layer analyte-specific trackable optical discs of the present invention, the disc has a first solid substrate and a second solid substrate, each having a laser-distal side and a laser-proximal side; a first reflective surface disposed upon the laser-proximal side of the first solid substrate, and a semireflective (second reflective) surface disposed upon the laser-distal side of the second solid substrate. In these embodiments, the second solid substrate with its semireflective surface is laser-proximal to the first solid substrate and its first reflective surface.

In especially preferred embodiments, the analyte-specific signal element is disposed confocally with a wobble groove. Because the trackable attribute may be engineered into either the first or second reflective layer, the analyte-specific signal element may be disposed confocally with the semireflective (second reflective) surface, confocally with the first reflective surface, or disposed substantially confocally with both.

The multiple data layer geometry permits disc assemblies in which the first and second solid substrates are reversibly separable, permitting the disposition of analyte-specific signal elements upon either the laser-proximal side of the reflective second surface or the laser-distal side of the semireflective surface prior to assembly. Further, the geometry permits embodiments in which channels, engineered into the disc, permit the introduction of sample for contact with the analyte-specific signal elements.

In yet another aspect, the invention provides an analyte-specific assay system, comprising an analyte-specific trackable optical disc of either single data layer- or multiple data layer-type; an optical disc reader; and a display, wherein the analyte-specific signal from the analyte-specific signal element is transmitted to the display by the optical disc reader. In the examples presented herein, the display is a digital oscilloscope, and the analyte-specific signal appears on the oscilloscope as a high amplitude, high frequency perturbation in the buffered HF signal. Although a digital oscilloscope is used in this prototypical system, in preferred embodiments of the present invention, the display is preferably the monitor of a digital computer, connected either directly or indirectly to the disc reader. Indirect connection, e.g., by means of a network or internet connection, permits the remote display of assay data.

In yet another aspect, the invention provides an analyte-specific assay kit, comprising: an analyte-specific trackable optical disc of either single data layer- or multiple data layer-type, and a sampling device, the sampling device adapted for collection of samples testable for the disc's specific analyte. Thus, for discs containing signal elements specific for analytes detectable in blood, the assay kit includes a blood sampling device; for discs containing signal elements specific for analytes detectable in water, as for environmental testing, the assay kit includes a field water sampling device; for disks containing signal elements specific for analytes detectable in urine, the assay kit includes a urine sampling device.

In another aspect, the invention provides a method of making the analyte-specific trackable optical discs. The invention thus provides a method of making an analyte-specific assay device, comprising the step of: disposing an analyte-specific signal element on an optical disc readably with a trackable attribute of said disc. In preferred embodiments, the method includes disposition of the analyte-specific signal element confocally with the trackable attribute, which preferably includes a wobble groove. As exemplified, the analyte-specific signal element includes an antibody or nucleic acid, and the analytical assay site is anchored to the disc by sulfur-gold bond; however, as further described the signal element, which may include any moiety capable of providing analyte specificity, may alternatively be disposed upon a cover, attachment of which renders the analyte-specific signal elements confocal with the disk's trackable attribute.

In yet another aspect, the invention provides methods of using the analyte-specific trackable optical discs of the present invention.

In one such aspect, the invention provides a method of using an optical disc reader/writer to signal the presence of analyte in a sample, comprising the step of: trackably reading (scanning) an analyte-specific optical disc after contacting the analyte-specific trackable optical disc with sample, and concurrently detecting analyte-specific signal therefrom. As would of course be understood, concurrent detection does not obligate concurrent discrimination of the analyte-specific signal, which may be effected subsequently. In preferred embodiments, the analyte-specific disc includes a wobble groove, the analyte-specific signal is detectable in the optical disc reader's HF signal, and the analyte-specific signal includes dimensional information about the analyte-specific signal element.

In especially preferred embodiments, the analyte-specific signal element reports the result of an immunoassay or nucleic acid hybridization assay. In other preferred embodiments, the analyte-specific signal element reports information about eukaryotic cells in the sample, particularly cells in a mammalian blood sample.

In another such aspect, the invention provides a method of segregating tracking signals from signals generated by an analyte-specific signal element disposed upon an optical disc, comprising: disposing analyte-specific signal elements confocally with a trackable attribute that produces minimal variation in the HF signal during trackable reading of said optical disc. In preferred embodiments, the trackable attribute is used in a substantially radial plane tracking scheme, and in most preferred embodiments, includes a wobble groove.

BRIEF DESCRIPTION OF THE DRAWINGS

The above and other objects and advantages of the present invention will be apparent upon consideration of the following detailed description taken in conjunction with the accompanying drawings, not drawn to scale, in which like characters refer to like parts throughout, and in which.

DETAILED DESCRIPTION OF THE INVENTION

In order that the invention herein described may be fully understood, the following detailed description is set forth. In the description, the following terms are employed.

As used herein, the term "nonoperational feature" means any structure on or within an optical disc that is capable of producing a signal when the disc is read by an optical disc reader, the signal of which, however, is not required (although possibly useful) for drive operation during reading. Nonoperational features include samples for analysis, objects or structures subject to inspection, molecules, cells, bead complexes, and analyte-specific signal elements, as described immediately below.

As used herein, the term "analyte-specific signal element" refers to any structure that may be used to signal the presence of a specific analyte in a sample applied to an optical disc. The term thus includes, inter alia, such signal elements as are exemplified herein—including cells—as well as those that are described in co-owned and copending U.S. patent applications Ser. No. 09/120,049 filed Jul. 21, 1998 and 08/888,935 filed Jul. 7, 1997, the disclosures of which are incorporated herein by reference in their entirety. The term includes both those structures that are alone detectable by an optical disc reader and those that require additional components to be rendered detectable.

Brief Description of a Conventional
  Optical Disc Reader And Disc

Figure 1A:
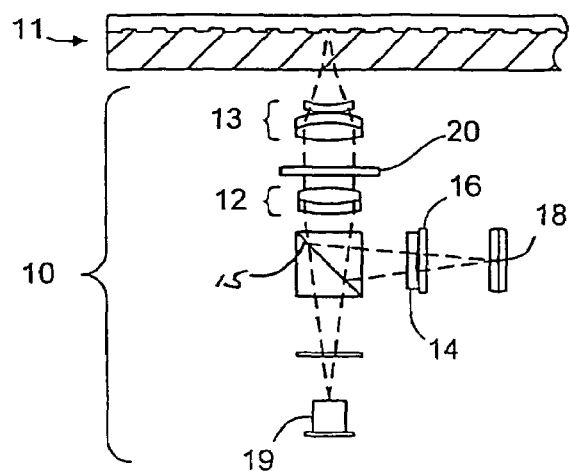
FIG. 1 shows a typical single-layer CD type disc and reader, with FIG. 1A presenting a side view of the reader's optical pickup oriented to read a CD disc which is shown in side cross-sectional view, with the laser optical path indicated by lines; with FIG. 1B showing a side cross-sectional view in the same orientation of the disc at greater magnification; and with FIG. 1C showing a perspective view of the surface of a CD-R disc with wobble groove.
Figure 1B:
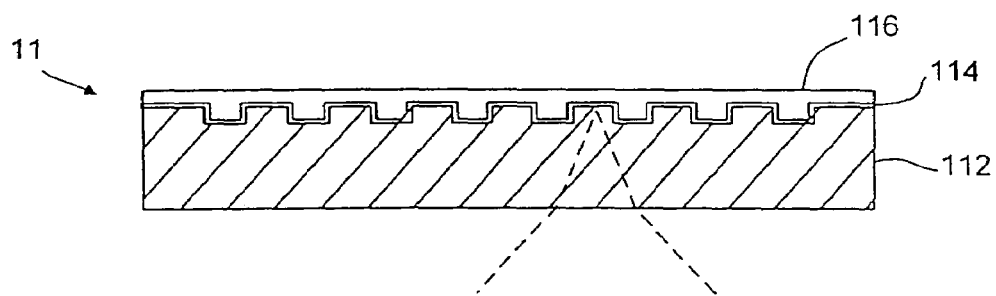

To provide some background for further discussion of the present invention, salient features of a conventional optical disc reader and optical disc are described briefly in connection with FIG. 1. FIG. 1A depicts the reader's optical pickup (objective assembly) 10 and a standard CD-type optical disc 11 with the light path therebetween indicated as dashed lines. For clarity, FIG. 1A depicts a minimal complement of the reader's optical pickup components. FIG. 1B provides a side cross-sectional enlarged view of disc 11 in the same orientation relative to the incident laser.

With reference to FIGS. 1A and 1B, the reader's optical pickup 10 includes laser source 19, lenses 12–14, beam splitter 15, quarter wave plate 20, and detector 18. Laser source 19, typically a laser diode, emits a laser beam which is collimated by lens 12. The collimated beam is then reflected toward optical disc 11 by beam splitter 15. Objective lens 13 focuses the laser beam onto a small spot on the laser-proximal, or first, surface of optical disc 11. By convention, disc layers are numbered upwards from laser-proximal to laser-distal surfaces.

The laser beam is reflected from reflective surface (also termed second surface) 114 of the disc and returned through objective lens 13 and quarter wave plate 20 to beam splitter 15. Quarter wave plate 20 changes the polarization of the laser beam so that beam splitter 15 directs the reflected laser beam through lens 14, which focuses the reflected laser beam onto detector 18. Astigmatic element 16, which may be a cylindrical lens, may be included between beam splitter 15 and detector 18 to introduce astigmatism in the reflected laser beam.

As shown in greater detail in FIG. 1B, CD-type disc 11 comprises three layers: from laser-proximal to laser-distal, the layers are transparent substrate 112, reflective layer 114, and protective layer 116. The total depth of the layers combined is nominally 1.2 mm. The figure is not drawn to scale.

Although the nominal thickness is 1.2 mm, the senior standard for compact disks, republished as IEC 908 (colloquially, the "Red Book"), permits physical thickness of 1.1–1.5 mm for all layers combined. Although the disc comprises three separate physical layers, there is only a single data layer, and the disc is thus conventionally described as a single data-layer (or "single layer") disc. Such discs are also termed herein "CD-type" discs.

Transparent substrate 112 makes up most of the 1.2 mm thickness of a typical CD-type disc, as measured along the optical axis, and provides both optical and structural features necessary for disc operation.

With respect to the optical features, the refractive properties of transparent substrate 112 serve further to focus the incident laser light on reflective layer 114. On the laser-proximal, or first, surface of a CD-type disc, the laser spot has a diameter of approximately 800 µm. Transparent substrate 112 further focuses the beam, achieving a diameter of approximately 1.7 µm at reflective surface 114, also called the second surface.

In design and manufacture of optical discs, the thickness and index of refraction of transparent substrate 112 are selected to assist in focusing a laser beam that passes through transparent substrate 112 onto reflective layer 114 so that data encoded thereon can be read or written. In a typical CD-recordable (CD-R) disc, transparent substrate 112 is composed principally of polycarbonate, and has an index of refraction is 1.55. It will be apparent to one skilled in the relevant arts that materials other than polycarbonate may be used, as long as the thickness and index of refraction of the materials provide sufficient assistance to the focusing system of the optical disc reader.

Transparent substrate 112 also provides the principal structural integrity of the disc. Reflective layer 114 is approximately 0.05 to 0.1 microns in thickness, and protective layer 116 typically comprises a lacquer material that hardens when exposed to UV light, and has a thickness between 10 and 30 microns. Thus, transparent substrate 112 makes up the major layer, and is the only layer capable of imparting sufficient rigidity to the disc to encode embossed data.

Substrate layer 112 is typically impressed with a spiral track that starts at the innermost readable portion of the disc and then spirals out to the outermost readable portion of the disc. In a non-recordable disc, this track is made up of a series of embossed pits, each having a depth of approximately ¼ the wavelength of the light that is used to read the disc. The pits have varying lengths, the length and spacing of the pits encoding the data. As further discussed below, the spiral groove of a recordable disc contains a dye rather than pits. Two portions of such a wobble groove 118, similar to the wobble groove found on a recordable disc, are shown in the perspective view of FIG. 1C.

Transparent substrate 112 is typically manufactured by an injection molding process, in which molten polycarbonate is injected into a mold cavity having a "stamper" with a reverse image of spiral groove 118 on one face of the mold cavity. The stamper is made from a master of the disc by electro-forming, which will be more fully described below. The injection molding process typically takes 5 to 10 seconds per disc.

Reflective layer 114 is approximately 0.05 to 0.1 microns in thickness, and typically comprises a reflective metallic material, such as aluminum, silver, gold, or copper. For the CD-R format, a reflection coefficient of approximately 65 percent is recommended in the official format specification, but few discs actually meet this level. Most drives have gain control circuitry, and are capable of reading discs having a much lower reflection coefficient. When the disc is being read, reflective layer 114 reflects the laser beam that is used to read or write the disc back through optical pickup 10 to sensors in the disc reader.

Reflective layer 114 is typically applied through a magnetron sputtering process, in which a solid target is bombarded with ions, releasing metal molecules that are used to form reflective layer 114. The vapor deposition process is slow, and is generally only used for mastering discs. A chemical wet "silvering" process (using silver, nickel, or other metal) may also be used to form reflective layer 114 on transparent substrate 112.

Protective layer 116 typically comprises a lacquer material that hardens when exposed to UV light, a process called "curing", and has a thickness between 10 and 30 microns. Protective layer 116 serves to protect reflective layer 114 from scratches and oxidation, and provides a convenient surface on which a label may be printed. Protective layer 116 is typically applied to transparent substrate 112 and reflective layer 114 through a spin-coating process, whereby a small amount of a material that hardens when exposed to UV light is sprayed on the disc near the inner diameter of reflective layer 114, and the disc is spun at high speed, causing a thin layer of the material to cover the surface of the disc. The disc is then exposed to UV light, causing the material to harden.

The various CD and DVD standards contemplate discs having a nominal depth (in the dimension defined by the optical axis) of 1.2 mm and a nominal diameter in the radial dimension of 120 mm.

Although the nominal thickness is 1.2 mm, the senior standard for compact disk technology (colloquially, the "Red Book"), republished as IEC 908, permits physical thickness of 1.1–1.5 mm (for all layers combined). Readers are capable of accommodating some additional variance, however, and discs suitable for reading by CD and DVD drives may have a depth maximally of about 2.4 mm and minimally of about 0.8 mm, preferably 1.0–1.4 mm, more preferably 1.1–1.3 mm, most preferably 1.2 mm. With respect to the nominal 120 mm diameter, disk readers may accommodate disks of radial diameter of 100–140 mm, preferably 110–130 mm, more preferably 115–125 mm, most preferably 120 mm.

Furthermore, the standard also provides for disks with radial diameter of 8 cm (80 mm): the dimensions of the mounting and clamping rings remains the same as that for 120 mm disks, as does disk depth; only the outer diameter is reduced, reducing the data area of the disk. Commercially available CD and DVD readers and reader/writers accommodate disks of this diameter in their disk tray. Such disks present certain advantages in the practice of the present invention, among which are a commensurate reduction in assay sample volume required to effect contact with the entire disk surface, as well as the ability to package such disk in a sleeve dimensioned identically to the sleeve of a 3 ½" magnetic floppy disk.

Furthermore, various additional standards, such as those defining a (magnetooptical) "minidisc" or analogue laser disk have been, or will be, developed. Thus, the discs of the present invention may have a radial diameter as small as 50 mm and as large as that for a standard laser disc, and may be adapted to such size standards as are developed in the future. One skilled in the art would further recognize that the term "disk" contemplates any suitably rotatable media, whether or not perfectly circular.

Figure 2A:
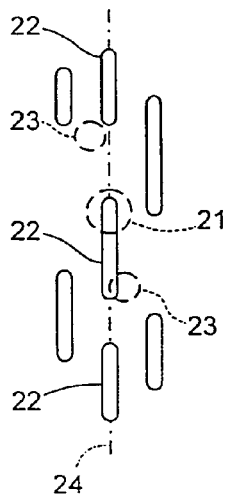
FIGS. 2A and 2B show, respectively, the position of beams from a typical three-beam pickup relative to a track on an optical disc, and an exemplary optical disc detector and associated electronics that use the three beams for tracking, focusing, and reading.
Figure 2B:
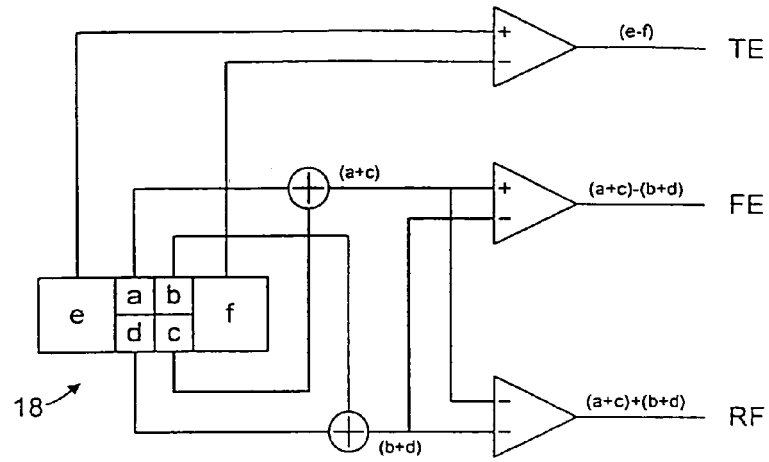

Referring now to FIG. 2, exemplary detector 18 and its associated electronics are described in more detail. Detector 18 typically comprises a central quad detector flanked by two additional detector elements. The quad detector is split into four elements arranged as shown by sensor elements 18a–18d in FIG. 2. Detector elements 18a–18f each provide an electrical signal indicative of the intensity of the reflected laser beam striking that element.

Typically a CD drive uses a three-beam pickup, wherein the laser beam is split into three beams, a main beam and two tracking beams. The main beam is focused onto the surface of an optical disc so that it is centered on a track, whereas the tracking beams fall on either side of the track. For example, as shown in FIG. 2A, main beam 21 is centered on track 24 as defined by pits 22, and tracking beams 23 fall on either side of track 24. By design, the three beams are reflected from the optical disc and directed to detector 18 such that main beam 21 falls on the quad detector, and tracking beams 23 fall on sensor elements 18e and 18f.

The sum of the signals from the quad sensor, e.g., 18a+18b+18c+18d, provides the radio frequency (RF) signal, also referred to as a high frequency (HF) or quad-sum (quad-sum) signal. As used herein the notation "18a+18b" indicates the sum of the signals from sensor element 18a and 18b. The RF (HF, quad-sum) signal is demodulated to recover data recorded on the optical disc.

Various pairs of the signals from sensor elements 18a–18f are also combined to provide feedback signals for tracking and focus control. For example, a tracking (tracking error, or TE) signal may be obtained from the difference between the 18e and 18f signals, e.g., 18e–18f. And, because of astigmatism introduced by astigmatic element 16, a focus error (FE) signal may be obtained from the difference between the 18a+18c and 18b+18d signals.

The circuitry of FIG. 2 is just one example of circuitry for providing focus and tracking error signals in an optical disc player. Numerous methods are known for providing these signals. For example, a focus error signal may be obtained by the critical angle method, described in patent U.S. Pat. No. 5,629,514 or the Foucault and astigmatism methods, described in *The Compact Disc Handbook*. Similarly, tracking error signals may be obtained using the single beam push-pull or three beam methods described in *The Compact Disc Handbook*, the differential phase method described in U.S. Pat. No. 5,130,963 or the single beam high frequency wobble method.

The RF signal, obtained from summing the signals from all of sensor elements 18a–18d, is processed to extract whatever data is recorded on the optical disc. First, the analog RF signal is conditioned, with normalization and equalization performed. Next, the analog signal is converted to a digital signal comprising a serial stream of digital data referred to as channel bits. The channel bit stream is then demodulated according to the modulation standard used for the type of optical disc being read. For example, CD type discs use eight-to-fourteen (also denominated "eight-of-fourteen") modulation (EFM) wherein a data byte, or eight data bits, are encoded in fourteen channel bits. There are three merging bits between each group of fourteen channel bits. Thus, when reading a CD type optical disc, seventeen channel bits are read from the optical disc, the merging bits are discarded, and the remaining fourteen bits are decoded, or demodulated, to obtain the original data byte. The data bytes themselves are grouped into blocks, which are further processed to reduce the effects of disc defects, such as scratches on the disc surface.

Typically, the processing is performed by analog circuitry in combination with one or more integrated circuit chips. Often, the circuitry may take the form of a special chip set.

Figure 3A:
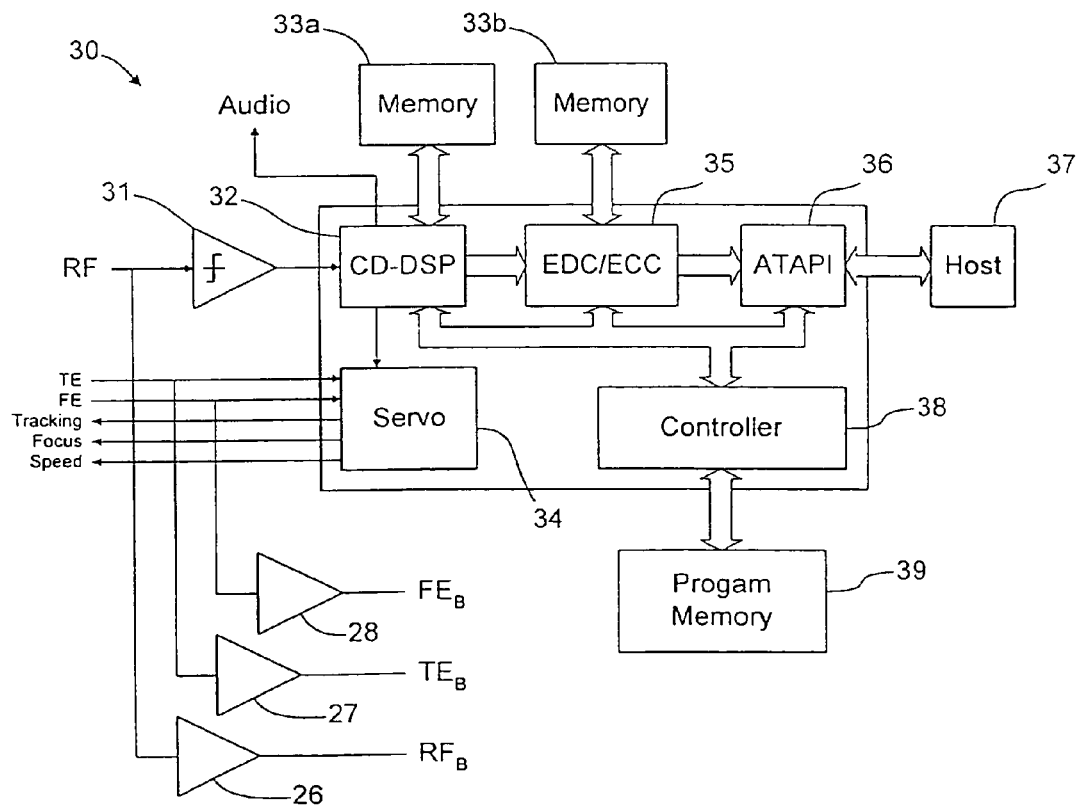
FIG. 3A shows an illustrative block diagram of chip set of a typical CD-type optical disc reader, modified to monitor signals for determining the presence of analyte-specific signal elements.
Figure 3B:
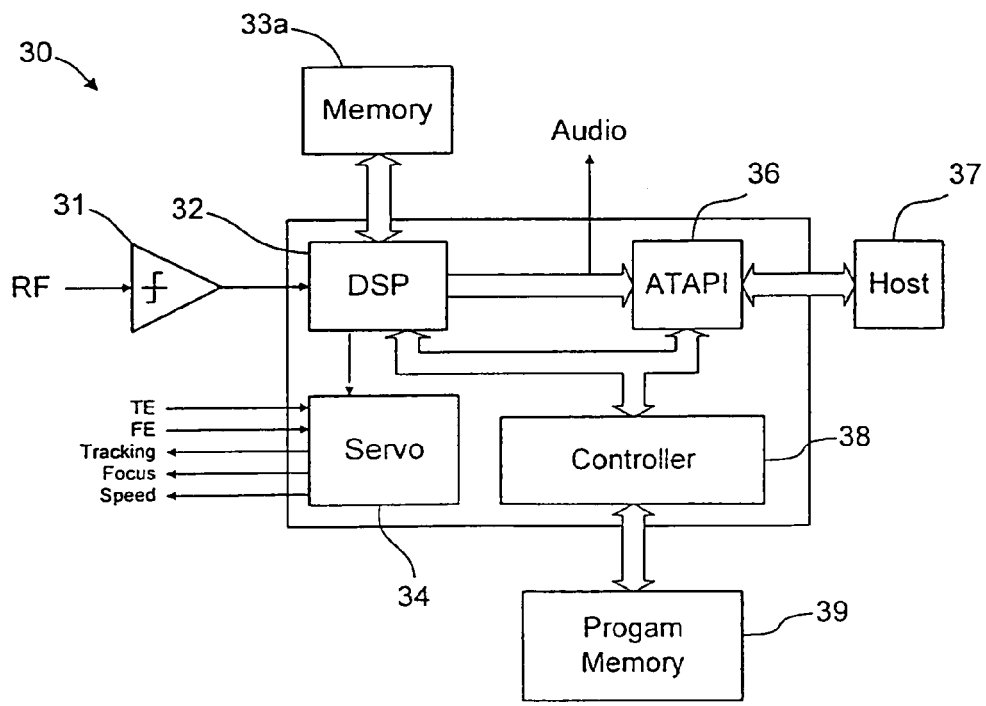
FIG. 3b shows an illustrative block diagram of chip set of a typical DVD-type optical disc reader.

FIGS. 3A and 3B are illustrative block diagrams of exemplary chip sets for a typical CD drive and DVD drive, respectively. In discussing the operation of typical CD and DVD drive circuitry, the CD circuitry of FIG. 3A is first described, then the differences in the DVD circuitry of FIG. 3B are addressed.

The RF signal from sensor 18 is converted to a square wave by comparator 31 which provides a high output when the RF signal is above a threshold level, and a low output when the RF signal is below the threshold.

CD-DSP 32 then samples the resulting square wave signal to determine the value of each channel bit. CD-DSP 32 further demodulates the channel bits to extract the data bytes which are then grouped into blocks and processed to correct errors that may have occurred. Memory 33a provides temporary storage for the data as it is being processed by CD-DSP 32 and assembled into blocks.

Servo block 34 analyzes the tracking error signal (TE) and provides a tracking control signal to the tracking mechanisms to ensure the pickup assembly maintains proper tracking. Similarly, a focus control signal is provided based on focus error signal FE. CD-DSP 32 provides an indication of the data rate of the RF signal which is used by servo block 34 to provide a speed control signal to the spindle motor of the optical disc drive.

In an audio CD player, after processing by CD-DSP 32, each data block is sent to audio reproduction circuitry not shown in FIG. 3. However, in some data storage applications, each data block may contain additional error detection codes (EDC) and error correction codes (ECC). EDC/ECC circuitry 35 uses the EDC and ECC codes to increase the integrity of the data block by detecting and correcting errors not already corrected by CD-DSP 32. Memory 33b, which may be combined with memory 33a, provides temporary storage for data blocks being processed by EDC/ECC circuitry 35.

Finally, the data blocks are transferred from the optical disc player to host 37 by means of interface circuitry 36. Although an ATAPI interface is shown, it will be understood by the skilled artisan that other interfaces, such as SCSI, Firewire, or Universal Serial Bus (USB), could also be used.

Controller 38 coordinates the operation of the various components of chip set 30, for example by coordinating the transfer of data blocks between CD-DSP 32 and EDC/ECC circuitry 35. Controller 38 also keeps track of which data block is being read and may keep track of various parameters indicative of the operational status of the optical disc reader.

For example, CD-DSP 32 and EDC/ECC circuitry 35 may provide information about the number of errors that were detected and corrected in the current data block. This information may be used by controller 38 to determine if the optical disc reader is operating satisfactorily and may adjust various operating parameters to optimize performance. For example, controller 38 may reduce the spindle speed of the optical disc reader if the error rate reaches an unacceptably high level. The information available to controller 38 may also be provided to host computer 37 via interface 36.

Program memory 39 contains program code for the operation of controller 38. In many optical disc reader chip sets, program memory 39 may also contain program instructions for CD-DSP 32 or EDC/ECC circuitry 35. This is advantageous for manufacturers in that the operation of the disc drive may be changed by simply changing the program code in program memory 39. For example, a newly developed method of modulating or encoding data on an optical disc may be accommodated by changing program memory 39.

While the foregoing description is sufficient for a basic understanding of the present invention, there are numerous alternative designs and configurations of an optical pickup and associated electronics which may be used in the context of the present invention. Further details and alternative designs are described in *Compact Disc Technology*, by Nakajima and Ogawa, IOS Press, Inc. (1992); *The Compact Disc Handbook*, by Pohlmann, A-R Editions, Inc. (1992); *Digital Audio and Compact Disc Technology*, by Baert et al. (eds.), Books Britain (1995); *CD-Rom Professional's CD-Recordable Handbook: The Complete Guide to Practical Desktop CD*, Starrett et al. (eds.), ISBN: 0910965188 (1996); which are incorporated herein in their entirety by this reference.

FIG. 3A also includes buffer amplifiers 26–28. These amplifiers enable external circuitry, such as oscilloscopes and analog to digital converters, to be connected to signals within the optical disc drive without interfering with normal drive operation. The digital oscilloscope tracings presented as FIGS. 13–18 herein represent such buffered RF (RFB) signals from a prototype reader.

As shown by the block diagram of FIG. 3B, circuitry for a DVD drive is similar to that of a CD drive. There are, however, some differences. For example, DVD formats do not use the same type of EDC/ECC circuitry as used in most CD-base data storage applications, so EDC/ECC circuitry is not needed. Rather, the function of the EDC/ECC codes and circuitry is built into the data-encoding method used for DVD, so the EDC/ECC function is performed by DSP 32.

As a general principle, there are four operational requirements that must be met for a typical optical disc system to function correctly: the reader must adequately monitor and control focus, radial position, tangential position, and speed. Control of radial and tangential position may collectively be subsumed under the rubric of tracking.

As discussed above and schematized in FIG. 1B, transparent substrate layer 112 of the optical disc is required to focus the reader's laser properly upon the reflective surface layer 114 of the disc. Failure to maintain correct thickness, transparency, and refractive index of transparent substrate layer 112 may render reflective surface 114 unreadable.

And as further discussed above, operational features encoded in the plane of reflective surface 114 must be read to maintain correct tracking. In standard pressed CDs, for example, the reader tracks a pitted spiral groove that is impressed upon transparent substrate 112. In recordable CDs, the reader similarly tracks a spiral groove impressed upon transparent substrate 112, but in this latter implementation, a groove filled with dye.

Figure 4:
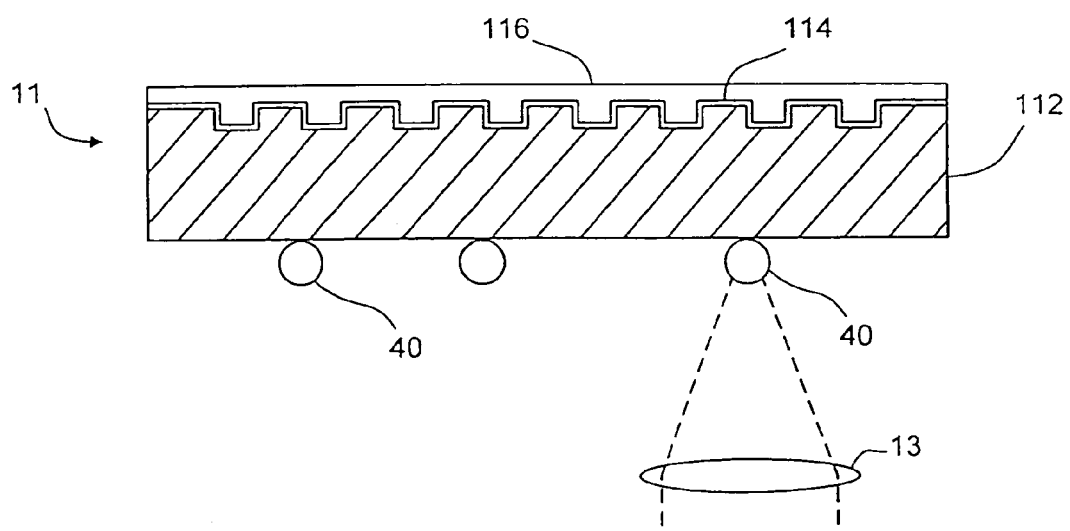
FIG. 4 shows structures applied to the air-incident, laser-proximal first surface of a typical single layer CD-type optical disc shown in side cross-sectional view, demonstrating interruption in the optical path to and from the reader's optical pickup.

FIG. 4 demonstrates that structures 40 applied to the air-incident, laser-proximal first surface of a typical CD-type optical disc lie laser-proximal to the optimal focal plane of the incident laser. Signal elements that are so disposed would be undetectable by standard means. First, these signal elements would have to be in the range of the beam size at the incident surface (800 $\mu$m) to be detectable by the laser source. And if so large, these structures 40 may, by virtue of their interposition between the laser and the reflective surface 114, interfere with reading operational features encoded in the reflective surface 114. It is for this reason that substantial efforts are undertaken during disc manufacture to ensure that the laser-proximal first surface of the disc is substantially free of imperfections by keeping surfaces on stampers and masters clean and clear of dust.

Thus, to adapt standard optical disc technology for purposive detection of analyte-specific structures and signal elements, there is a need for optical disc geometries and tracking schemes that overcome these problems. There is a need for optical disc geometries and tracking schemes that permit disc tracking signals to be acquired concurrently with and discriminated from signals generated by analyte-specific signal elements disposed upon the surface of an optical disc.

Single Data Layer Analyte-Specific Assay Discs

A first series of embodiments of discs built in accordance with the principles of the present invention, herein collectively termed "single data layer" embodiments, solves these problems by exploiting two novel approaches.

First, we have found that the physical orientation of standard, single data-layer, CD-type optical discs may effectively be inverted, presenting what would otherwise be a laser-distal surface as the laser-proximal first surface of the disc. To compensate for the inverted physical orientation, an inverted image of the disc's operational features is used. Second, we have found that radial plane tracking schemes, such as the wobble groove scheme utilized in CD-R, may advantageously be used on such inverted discs to provide tracking signals that may be detected concurrently with, and discriminated from, analyte-specific signals produced by analyte-specific signal elements disposed upon the disc's first surface.

Examples 2–3 presented herein below demonstrate the successful use of such single-layer, first surface discs (1) to detect IgG in human blood by immunoassay, and (2) to detect and characterize human erythrocytes captured upon the surface of an optical disc by specific immunologic reaction, using a minimally-modified optical disc reader.

Example 7 demonstrates the adaptation of a nucleic acid-based assay to the detection principles herein defined.

For purposes solely of orientation and discussion, FIGS. 5A–5D demonstrate a stepwise conversion of a standard single data layer CD-type optical disc to a single data layer, first surface, analyte-specific trackable disc of the present invention. FIGS. 5A–5D are not intended to imply a manufacturing scheme; manufacture of the single data layer first-surface analyte-specific discs of the present invention is further discussed below and exemplified in Examples 1 and 5.

Figure 5A:
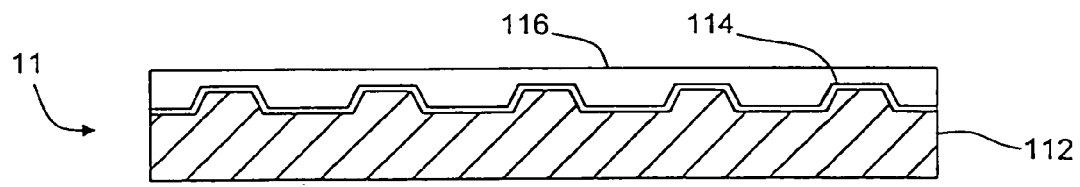
FIG. 5 demonstrates a hypothetical stepwise conversion of a standard CD-type single layer optical disc to a single layer, first surface, trackable analyte-specific disc of the present invention, with FIG. 5A showing a side cross-sectional view of a typical disc, with laser incident from below.
FIG. 5B demonstrating physical inversion of the disc.
FIG. 5C showing compensatory inversion of the data-encoding pits/grooves and lands.
FIG. 5D demonstrating further removal the protective layer.
Figure 5B:
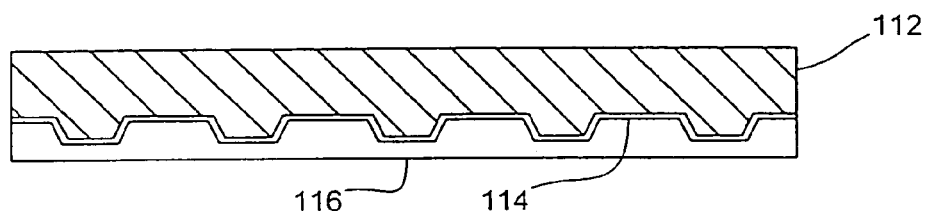

Shown in FIG. 5A is a side cross-sectional view of a standard CD-type optical disc identical to the disc depicted in FIG. 1B. As in FIG. 1, laser light by convention herein is incident from below. FIG. 5B demonstrates physical inversion of the disc, with protective layer 116 now presented as the most laser-proximal layer, reflective surface 114 presented distal thereto, with transparent substrate 112 following thereafter as the most laser-distal surface of the disc.

Figure 5C:
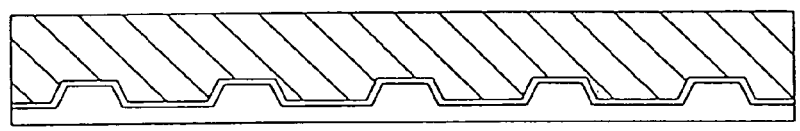

From the perspective of the optical pickup of the reader, physical inversion of the disc effectively converts each land to a groove (or pit) and each groove (or pit) to a land. Inversion also effects a reflection, in the radial plane, of any nonsymmetric feature, such as a spiral track. To restore the proper orientation of data after physical inversion of the disc, and in particular to restore the proper orientation of data encoding operational features of the disc, such as tracking features, it would thus be necessary to engineer a compensatory inversion of the lands/grooves, as depicted in FIG. 5C.

Figure 5D:
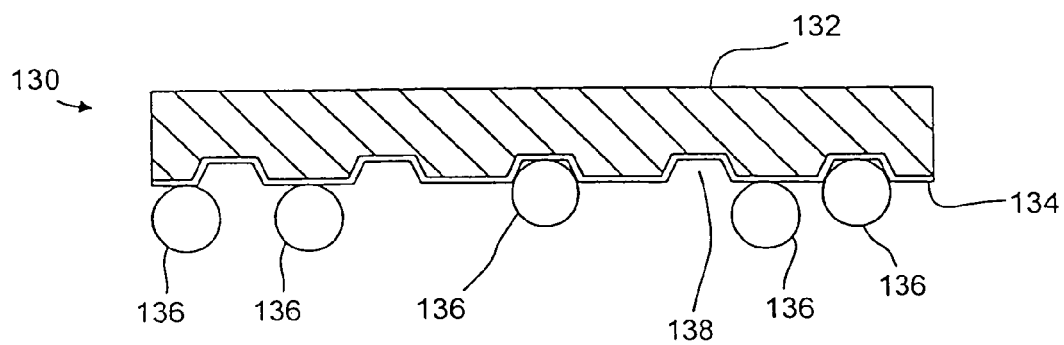

FIG. 5D shows a single data layer first surface disc 130 of the present invention. As compared to the inverted disc of FIGS. 5B and 5C, the protective layer 116 has been removed and analyte-specific signal elements 136 have been disposed upon reflective surface 134.

In such first surface assay discs, the analyte-specific signal elements are located in substantially the same focal plane as—that is, substantially confocal with—the tracking (or other operational) features encoded in the reflective surface layer of the disc. The confocal geometry greatly simplifies the problem of achieving and maintaining focus concurrently on the disc's operational features and the analyte-specific signal elements.

It will be understood that the analyte-specific signal elements and the operational (particularly, tracking) features need not be in the identical focal plane—it suffices that the signal elements and operational features are sufficiently confocal as to permit the disc reader's optical head to detect them both.

Figure 6A:
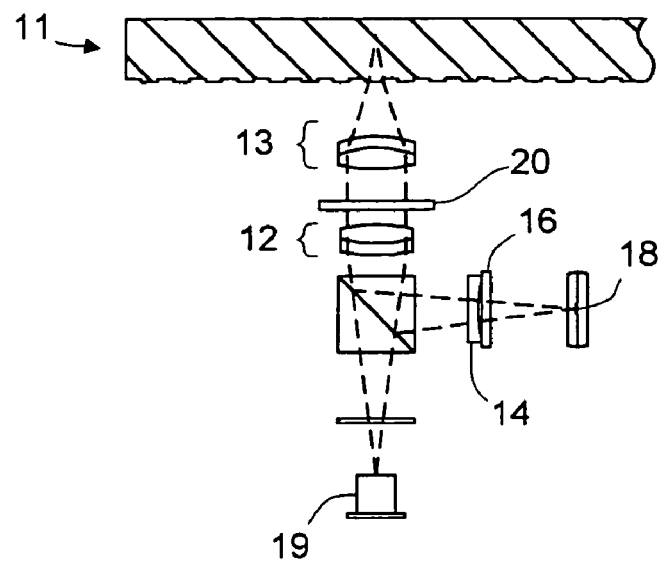
FIG. 6 is a side view of an optical pickup positioned to read a single layer, first surface, trackable analyte-specific disc of the present invention shown in side cross-sectional view, with the laser optical path indicated by lines, with FIG. 6A demonstrating the focus before addition of a further focusing lens to the optical pickup, and FIG. 6B demonstrating the change in focus with addition of a further focusing lens to the optical pickup.
Figure 6B:
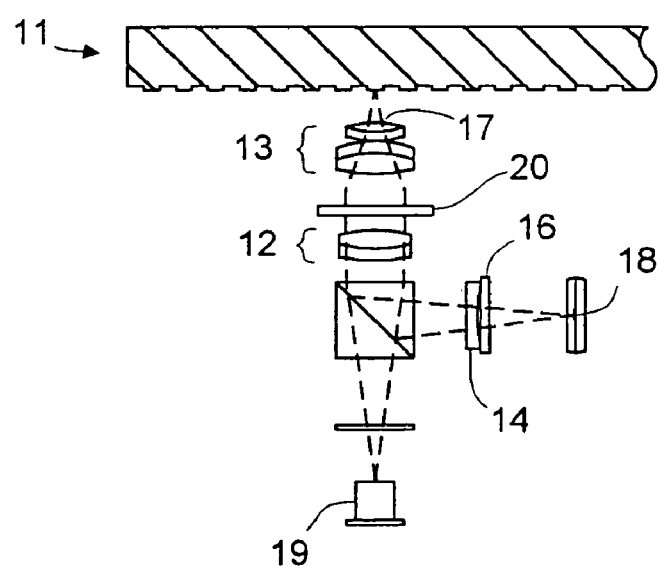

Of course, it is also readily apparent that, with reflective layer 134 now presented as the first surface of the disc, there is no transparent substrate layer 112 present to assist the laser focus, as in a standard disc. One simple solution, shown in FIG. 6B, is to add an extra focus correction lens 17 to the disc reader's optical head pickup. The reader used to produce the data presented in Examples 2 and 3 herein was so modified.

Alternatively, or in addition, the distance between the optical pickup and the disc's first surface may be adjusted so that the laser will focus correctly on the first surface of the disc.

Yet another alternative, a preferred embodiment further described below, adjusts the disc itself, rather than the reader. In this preferred embodiment, a nonintegral laser-refracting member is attached as a cover to the laser-proximal side of the disc. This nonintegral cover serves to refract, and thus to focus, the incident light on the disc's operational plane. By convention, that operational plane would now be counted the second surface of the disc. Although a nonintegral member is presently preferred, an integral cover, hingeably or otherwise modifiably attached, may also be used.

Whichever solution or combination of solutions is used to readjust focus, it should be apparent that the described single data layer disc geometry eliminates optical constraints on the composition chosen for substrate 132, relative to the optical constraints above-described for transparent substrate 112. That is, since layer 132 of the present first-surface assay discs is not used to refract the incident laser light, in contrast to layer 112 of a standard disc, the transparency, index of refraction and thickness of layer 132 may be adjusted without regard to these optical parameters. This presents advantages in manufacture not readily achievable with standard discs. However, given the installed base of existing disc manufacturing devices, it is presently preferred to manufacture the first-surface assay discs of the present invention using polycarbonate, as described below.

Although the novel disc geometry just described solves the problem of focus, it does not of itself solve the problem of maintaining tracking concurrently with the reading of analyte-specific signals.

A standard, nonrecordable, pressed CD-ROM disc, as mentioned above, contains a spiral track of pits impressed upon transparent substrate layer 112, the size and spacing of the pits encoding the data, the pits themselves required to meet the operational requirements of the disc reader. Coating with reflective layer 114 renders the pits and information encoded thereby detectable through changes in light intensity at detector 18.

As is well known in the art, the depth of the pits is chosen to maximize optical discrimination of the pits from the lands therebetween. The problem in adapting such discs for laser microscopic or other analyte-specific uses is that analyte-specific signal elements disposed upon the disc surface will similarly cause changes in light intensity, changes that may be insufficiently distinguishable from tracking signals as to prevent concurrent acquisition and discrimination of both tracking and analyte-specific signals.

Put more generally, any tracking scheme that includes pits is predicated in part upon signals generated by disc perturbations that lie outside the disc's radial plane, including perturbations in the optical axis defined by the relationship of the optical head pickup to the disc's first surface. And as is apparent in FIG. 5D, analyte-specific signal elements also present perturbations in the nonradial direction, that is, in the axis of the optical path.

We have found that radial-plane tracking schemes, such as a wobble groove, that rely substantially on perturbations in the radial plane of the disc, present a preferred solution to this problem, segregating the tracking signal from the quad sum (HF, RF) signal, permitting the quad sum signal to be used to detect signals from nonoperational features, such as analyte-specific signal elements.

Figure 1C:
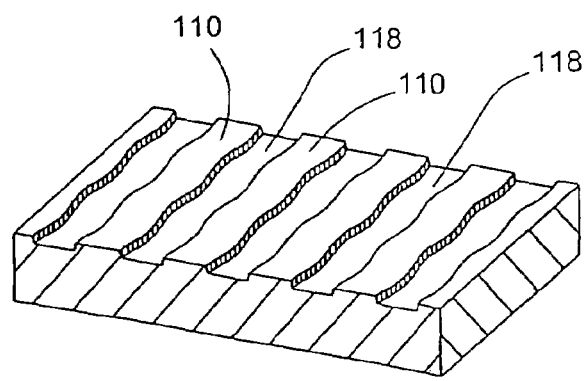

Typical CD-Recordable (CD-R) discs have a spiral groove having a track pitch of approximately 1.6 microns. As shown in FIG. 1C, this tracking groove 118, several sections of which are shown, includes a wobble that lies strictly in the radial plane of the disc. For CD-R discs, the wobble provides a signal with a frequency of 22.05 KHz; for DVD-R discs, the wobble in the spiral groove provides a wobble signal with a frequency of 140 KHz. The optical reader/writer drive adjusts the spindle rotation rate to maintain this frequency, and thus to maintain a constant linear velocity beneath the objective assembly (optical pickup), irrespective of the place being read on the disc.

The depth of wobble groove 118 is typically chosen to optimize the tracking signal. A depth that is approximately ⅛ of the wavelength of the incident laser light will provide a very strong tracking signal. Thus, assuming that a "standard" 780 nm laser is used to read disc 130, wobble groove 138 should have a depth of approximately 97.5 nm. Alternatively, the track may have a depth approximately equal to any odd multiple of ⅛th of the wavelength (such as ⅜λ or ⅝λ).

Critically, however, whatever depth is chosen for this groove, that depth remains substantially constant; it is the wobble itself, a perturbation that lies solely in the radial plane, that provides the information for tracking. Thus, tracking may be accomplished by focusing on the groove itself or, alternatively, on the lands therebetween; the information content, lying as it does in the radial plane, would be the same.

The result, from the standpoint of detector 18, is that the wobble groove causes minimal change in the quad-sum (A+B+C+D) signal; tracking is accomplished with minimal quad-sum signal variance. Thus, wobble tracking, or any other substantially radial-plane tracking scheme, allows tracking with no distinguishable features in the HF pattern. We refer to this as segregation of the tracking signal from the nonoperational (here, particularly, analyte-specific) signal.

A second major advantage of wobble tracking in the single data layer embodiments of the present invention is that the wobble gives a relatively low frequency to lock for tracking. Under the existing CD-R standard, the wobble provides a wobble signal with a frequency of 22.05 KHz. The much higher frequency events occasioned by analyte-specific signal elements, exemplified herein by structures in the 0.5–10 micron size range, may be readily distinguished, and are of sufficiently short duration as to prevent loss of tracking. Furthermore, a low-pass filter may be applied to remove such high frequency events from the signal reported by detector 18 for purposes of tracking, further ensuring correct tracing. As would be understood, such filter would of course be omitted from that portion of the incident signal used to detect analyte-specific signals.

A third major advantage of a wobble groove as tracking scheme for single data layer analyte-specific assay discs is that the wobble signal may be used by the drive to maintain a constant linear scanning velocity at all points on the disc. This permits dimensionality information about the high frequency analyte-specific event readily to be calculated, as shown in Example 3 and further discussed below.

A fourth major advantage of a wobble groove as a tracking scheme for single data layer analyte-specific assay discs relates to the increased density of user data that may usefully be encoded and decoded relative to other tracking schemes.

The smallest digital structure permissible by the CD standard is the block (or frame), which includes 24 bytes of user data embedded within a total of 33 bytes of data, as follows:

| Synch   | Subcode | User data | Parity  | User data | Parity  |
|---------|---------|-----------|---------|-----------|---------|
| 27 bits | 1 byte  | 12 bytes  | 4 bytes | 12 bytes  | 4 bytes | where "synch" is 27 bits of synchronization data, "subcode" contains a byte of control information, and two 4 byte parity words are interpolated for purposes of error detection and error correction.

With a wobble, there is no overhead required for synchronization, subcode, or parity—all of that information is encoded or encodable in the wobble. Thus, with a wobble tracking scheme, a total of 33 bytes are available for user data per frame (block), increasing substantially the information that may placed readably upon the disk.

On CD-R discs, an additional signal, known as a bi-phase mark signal, may be encoded, also in the radial plane of the disc, within the wobble, to provide logical position information. For DVD-R formats, similar information is provided using a "land pre-pit" encoding, whereby pre-stamped notches in the land areas (i.e., between the wobble grooves) encode address information. In either CD or DVD format used for the present invention, the biphase mark or land prepit coding may optionally be left out of the assay area.

It should be noted that at present, only optical disc recorders (writers) include the ability to detect the wobble groove, the biphase mark signal, or the land pre-pit encoded information. For this reason, the optical drive used to read the discs described herein will usually be an optical reader/writer, rather than a standard optical reader, even though the ability to write data to an optical disc is not necessary in many embodiments the present invention. It will be understood, however, that any drive that may be designed in the future to detect such tracking features, whether or not capable of writing, will similarly be useful in the practice of the present invention.

As was mentioned briefly above, the standard wobble groove used on a CD-R disc cannot be used identically on the single data layer assay disc of the present invention, the latter presenting an inverse orientation to the detector relative to a standard CD-R disc. Instead, an inverse image of a standard CD-R wobble groove must be impressed on substrate 132 of disc 130.

As set forth in detail in Examples 1 and 5 herein below, standard disc manufacturing processes must be modified to generate such a reverse image.

As is well known in the art, a stamper is needed for use in the injection molding process. The stamper is produced through an electroforming process.

Briefly, the process begins with the creation of a nickeled (or silvered) glass master disc. The master disc is placed in a galvanic nickel electrolyte bath, where it serves as the cathode of an electric circuit. A nickel anode is used to deposit a layer of nickel on the surface of the master disc, creating a nickel "father" part. When this electroforming process is complete, the nickel father part is separated from the master, typically destroying the master in the process. As a result of this process, the father part is embossed with a negative reverse image of the master.

Although the father part may be used directly as a stamper in the injection molding process, it has proven more efficient in the art to generate multiple identical copies of the father, termed "sons", to permit the injection molding process to be performed in parallel. The creation of a family of electroformed parts from one original nickel part is termed "matrixing."

Thus, the father part is typically used galvanically to generate numerous "mother" parts, each of which is identically embossed with a positive forward image of the master disc. The mother parts, in turn, are used to generate numerous stampers (or "sons"), identical in orientation to the "father" and which thus have a negative reverse image of the master disc. The "sons" may then be used as "stampers" in the injection molding process.

To produce a disc with a reverse image, as in the single data layer embodiments of the present invention, a stamper with forward image, rather than reverse image, is needed. One solution is simply to generate, at the outset, a master disc with an inverse image of the requisite tracking features, such as a wobble groove meeting the CD-R or DVD-R standards.

Alternatively, a standard master may be used to begin a modified matrixing procedure in which a "mother" part, rather than "son" part, is ultimately used as a "stamper" in the injection molding machine. As set forth in Examples 1 and 5, the discs used in the experiments reported herein were generated at EXIMPO S. R. O. (Prague, Czech Republic), using such modified matrixing procedure.

In the modified matrixing procedure, the use of a mother part directly in the injection molding process occasioned some initial difficulty with venting in a standard injection molding machine. Various parameters of the injection molding machine, as would be apparent to the skilled artisan, were adjusted so that molten polycarbonate flowed over the mold properly. For example, the temperature at which the polycarbonate is injected was raised to ensure that the molten polycarbonate was less viscous. Though this increased temperature may alter the optical properties (e.g., birefringence) of the polycarbonate, the optical properties of polycarbonate layer 132 are immaterial to the performance of these assay discs, inasmuch as the laser never passes through this layer. FIGS. 41A–41I present the mold settings used in the manufacture of the disks manufactured as set forth in Example 5.

To demonstrate that these principles may be used to generate a trackable optical disc with concurrently readable analyte-specific signal elements, single data-layer, first-surface analyte-specific assay discs were manufactured as set forth in detail in Example 1 and essentially as schematized in FIG. 5D. Each disc contained an inverse image wobble groove impressed upon substrate 132, composed of injection-molded polycarbonate, the groove pitch being 1.6 $\mu$m and the wobble frequency approximating that set forth in the CD-R standard. A gold layer was deposited on the laser-proximal surface thereof to form reflective layer 134.

In a first series of experiments, reported in detail in Example 2, an assay site specific for human immunoglobulin G (IgG) was constructed on a small portion of the air-incident gold surface of the disc.

Figure 7A:
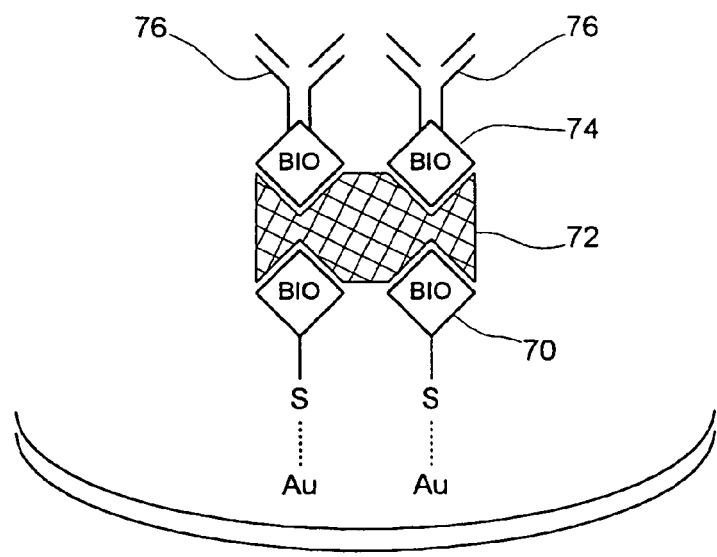
FIG. 7 schematizes the molecular components an IgG-specific immunoassay site constructed on the reflective surface of a first surface, trackable analyte-specific optical disc of the present invention, with FIG. 7A showing the assay site prior to addition of sample and FIG. 7B showing the immunospecific adherence of a latex sphere mediated by IgG in a human blood sample following addition of a human blood sample and "development" thereafter by further addition of anti-IgG conjugated latex spheres.

As schematized in FIG. 7A, the assay site was constructed as a three-layer sandwich; as would be understood by those skilled in the art of clinical assays, the purpose of such sandwich is to present the final sandwich layer, antibody 76, for analyte capture and detection. As would also be understood by those skilled in the art, the assay site itself contains many such trimolecular sandwiches, only one of which is schematized in FIG. 7.

In the first series of experiments, antibody 76 was chosen for its specificity for human immunoglobulin G (IgG), which is found at a concentration of approximately 1.1 g/dl in normal human blood.

A sample of human blood, drawn from an adult volunteer, was applied to the assay site of the disc and briefly incubated thereon. The disc was washed, and then "developed" by application of 3 $\mu$m latex spheres, each of which had previously been coated with antibodies specific for human IgG. The disc was then washed again. As schematized in FIG. 7B, the result of such a process is the IgG-mediated specific adherence of the latex spheres 79 to the disc. Absent IgG in the blood sample, the latex spheres would be removed during wash.

Figure 8:
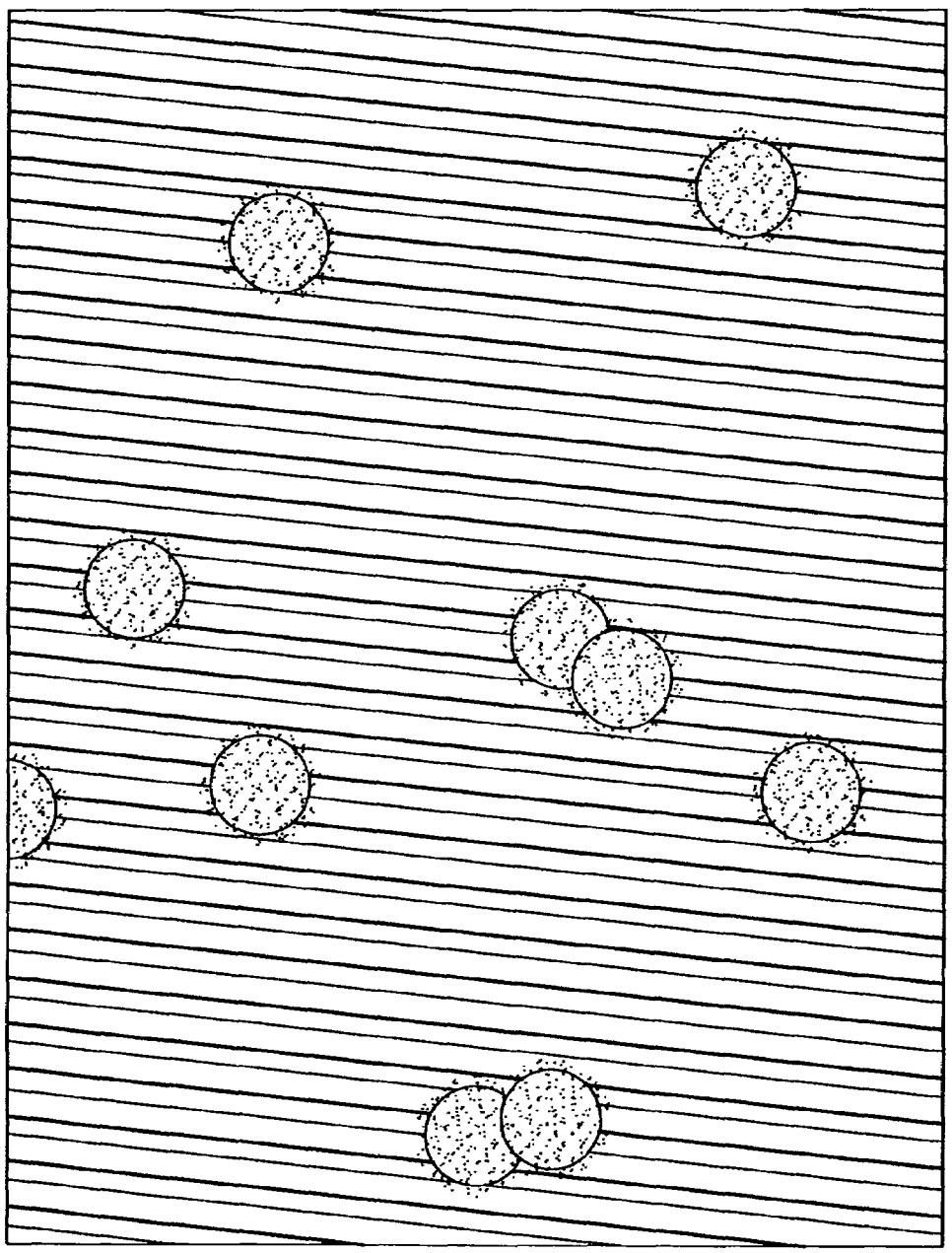
FIG. 8 is a video image captured from a light microscopic examination of a portion of the IgG-specific first surface analyte-specific Trackable assay disc after application of human blood and antibody-conjugated latex spheres.

FIG. 8 is a video image captured from a light microscopic examination of a portion of the IgG-specific disc following application of human blood and antibody-conjugated latex spheres. The latex spheres are readily apparent, as is the wobble groove itself. In this video capture image, the lighter areas are the grooves and the darker areas the "lands" between the grooves. Magnification precludes the continuity of the groove from being observed.

The video capture image suggests that many, if not all, of the latex spheres are positioned directly over the wobble groove. This orientation proves remarkably advantageous, maximizing the analyte-specific perturbation, and thus analyte-specific signal, in the tracking direction.

It should be readily apparent that the size of the signaling moiety relative to the width of the groove may advantageously be adjusted to facilitate such centering. Example 4 presents a calculation of an optimized relationship of the signaling moiety's size to groove width. Similarly, the size of the molecular tether at the assay site, here a trimolecular biotin-streptavidin-biotin sandwich, may advantageously be adjusted to facilitate a moderate, albeit circumscribed, movement of such signaling moieties to allow such positioning. Polymeric backbones of varying length that prove useful for signaling moieties are described in co-owned and copending U.S. patent application Ser. Nos. 09/120,049, filed Jul. 21, 1998 and 08/888,935 filed Jul. 7, 1997, the disclosures of which are hereby incorporated by reference. Furthermore, the shape of the groove itself may be adjusted, within the CD and DVD specifications, to facilitate such positioning.

Figure 9:
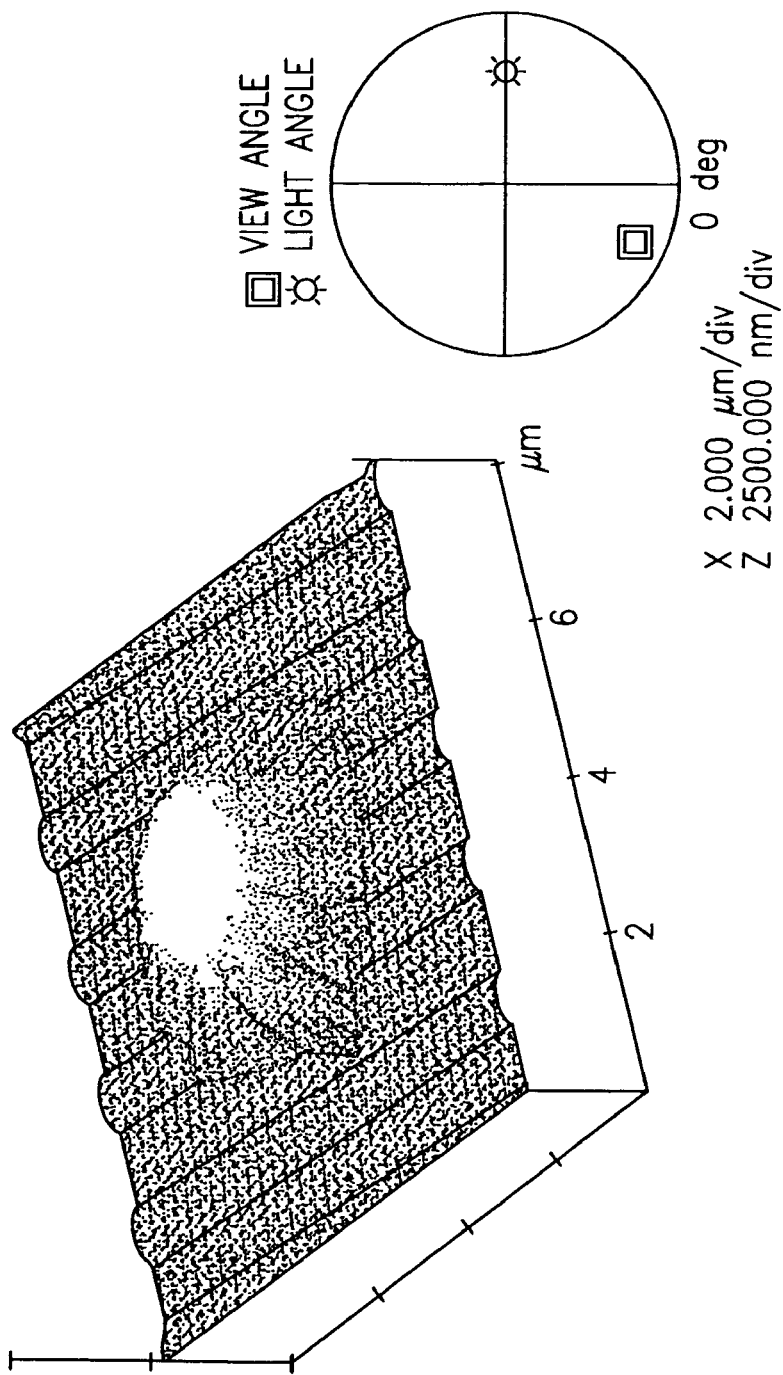
FIGS. 9 and 10 are atomic force microscope (AFM) images of a single latex sphere immunospecifically adherent to a first-surface trackable human-IgG specific disc, at somewhat higher magnification than that used in FIG. 8, with summaries quantitating dimensions observed by the AFM during image acquisition.
Figure 10:
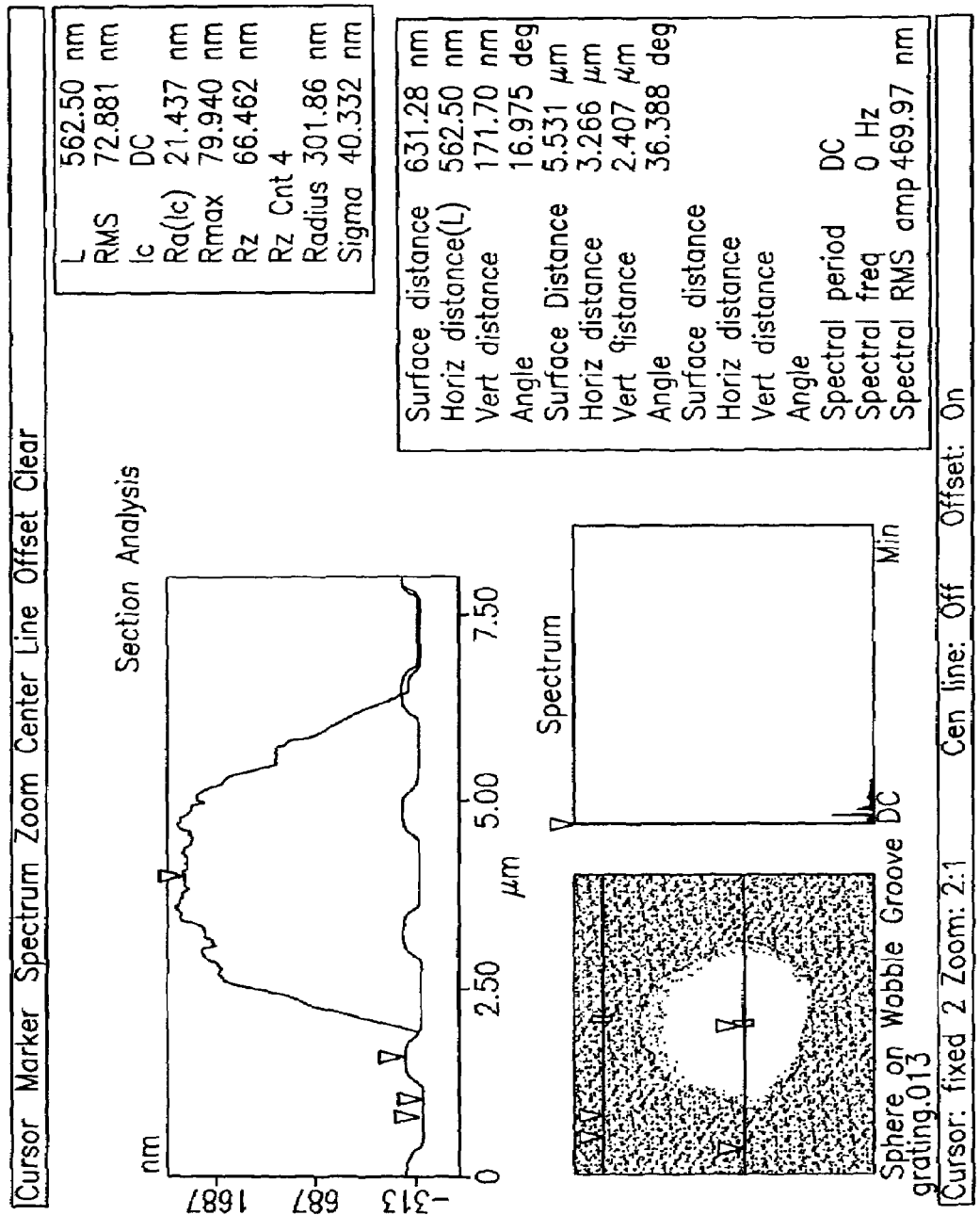

FIGS. 9 and 10 are atomic force microscope (AFM) images of a single latex sphere adherent to the disc, at somewhat higher magnification than that used in FIG. 8. Readily evident in FIG. 9 is the wobble groove itself and a single latex sphere centered over one turn of the groove. FIG. 10 presents AFM-acquired quantitative data. The groove measures 171.70 nm deep. The height of the latex sphere above the bottom of the groove is 2.407 $\mu$m.

Figure 11:
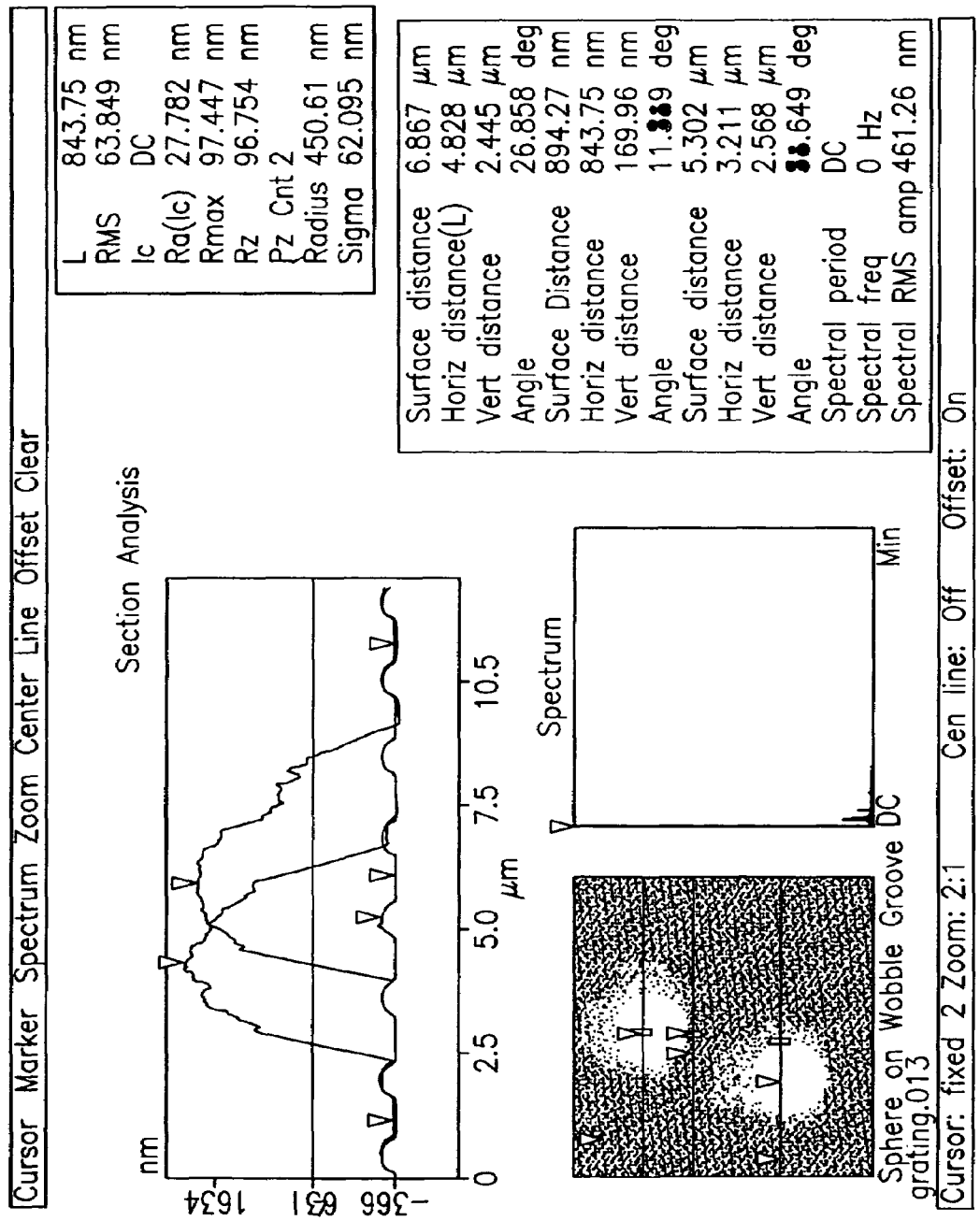
FIG. 11 is an atomic force microscope image of two latex spheres immunospecifically adherent to a first-surface trackable human-IgG specific disc and present in the same AFM field, with summary quantitating dimensions observed by the AFM during image acquisition.

FIG. 11 is an atomic force microscope image of two latex spheres in a single microscopic field. The quantitative sectional analysis illustrates the uniformity of the latex spheres used to develop this anti-IgG immunoassay. In addition, the quantitative sectional analysis identifies the horizontal distance between the center of the land and the center of the adjacent groove as 843.75 nm (0.84 $\mu$m), in excellent agreement with the desired track pitch of 1.6 $\mu$m. FIG. 11 further illustrate that the center of each of the spheres falls over a groove.

A second series of experiments, reported in Example 3, demonstrates that such analyte-specific signal elements may reliably be detected by a minimally-modified CD-R device as high frequency, high amplitude changes in the HF signal. That is, the above-described single-layer first surface assay disc with inverted image wobble groove permits tracking signals to be acquired concurrently with and discriminated from signals generated by analyte-specific signal elements disposed upon the surface of an optical disc.

As further described in Example 3, single data layer, first surface discs were prepared as set forth in Example 1. An assay site was prepared essentially as in Example 2, but substituting an anti-glycophorin antibody for the anti-IgG antibody 76 used in Example 2. Glycophorin is a protein that appears on the surface of all human erythrocytes (red blood cells, RBCs).

A heparinized sample of human blood (10 µl) was applied to the assay site, and the disc was then rinsed briefly.

Figure 12:
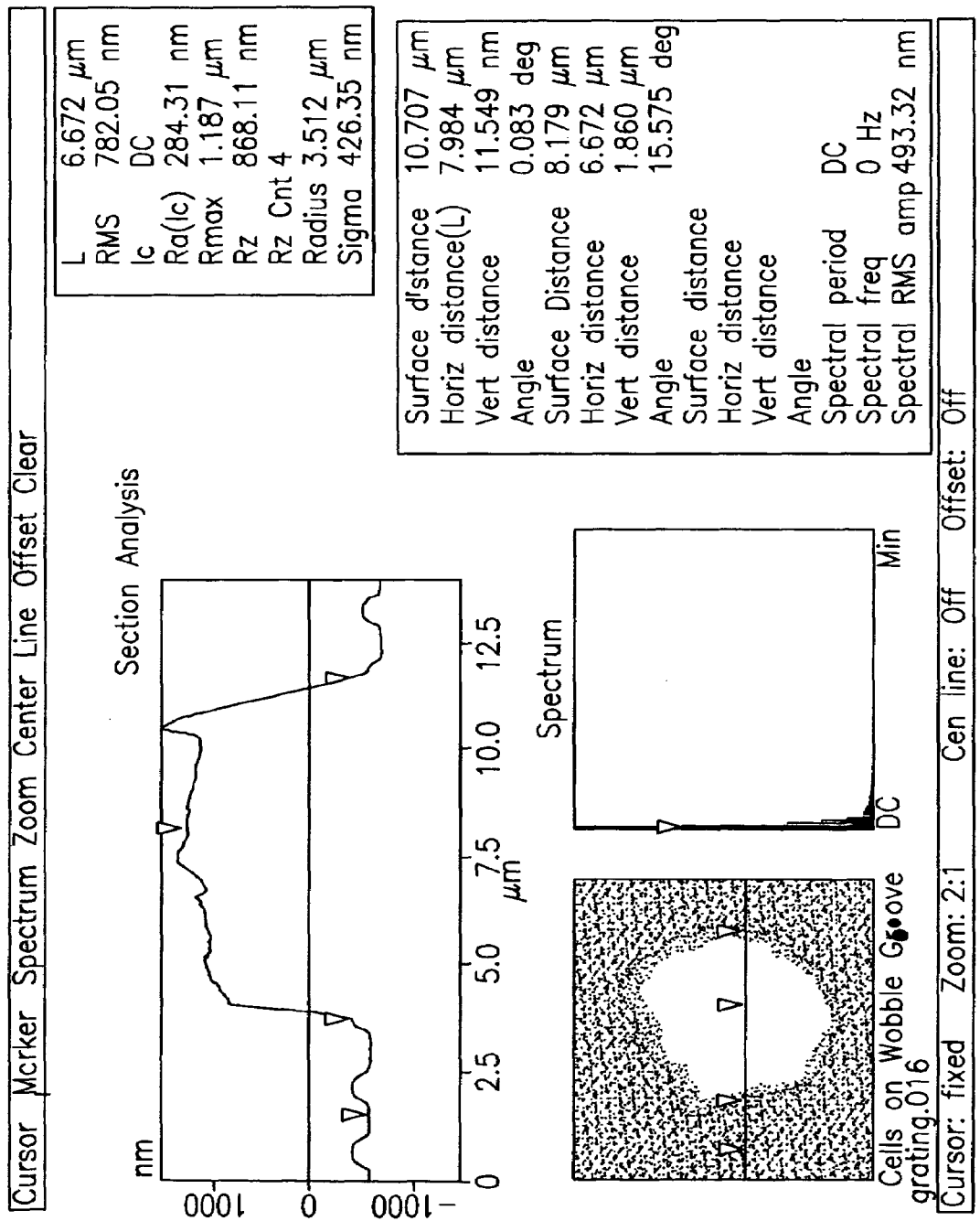
FIG. 12 is an AFM image and quantitative dimensional summary of a red blood cell (RBC) immunospecifically adherent to the surface of a first surface trackable human RBC-specific disc.

FIG. 12 is an atomic force microscopic image confirming the immunospecific adherence of RBCs to the assay site of the disc. As noted in the quantitative analysis, the RBC's horizontal size is given as 7.984 µm, in agreement with the known diameter of red blood cells (8 µm); this size is clearly different from the uniform 3 µm diameter of the latex spheres used and observed in Example 2. The height of the RBC above the bottom of a groove is observed to be 1.8 µm.

Figure 13:
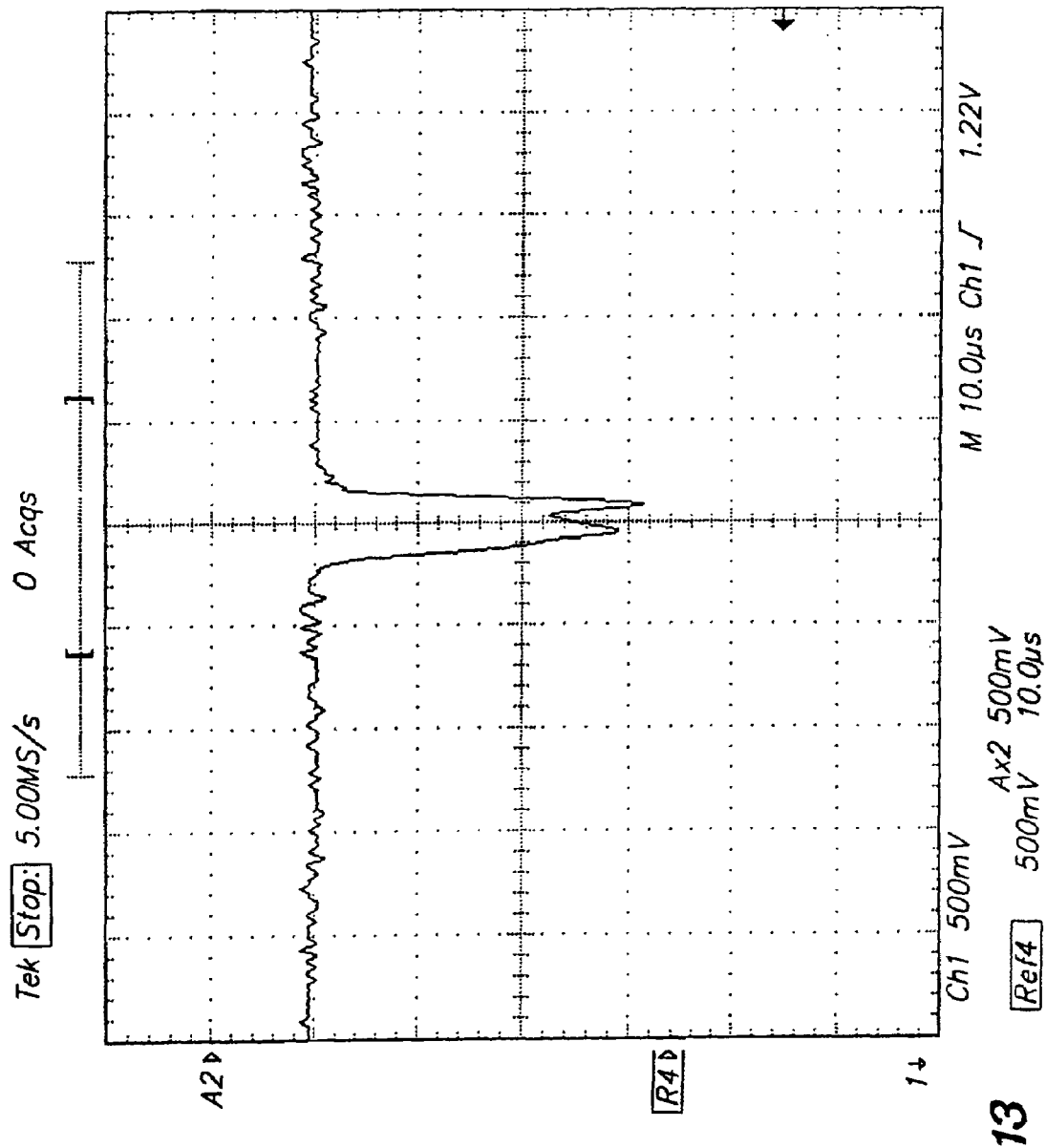
FIG. 13 is a digital oscilloscope tracing showing the analyte-specific perturbation in HF (quad-sum) signal obtained by an optical disc reader's trackable scanning over a red blood cell immunospecifically adherent to the surface of a first surface trackable RBC-specific disc, with X axis displaying time and Y axis displaying the magnitude of the quad sum signal.

As further described in Example 3, a CD-R device manufactured by CD Associates, Inc. (Irvine, Calif.) for quality control use in the optical disc industry was used to read the disc. The drive's CD-R wobble tracking system (model RSL100) was modified by addition of lens 17 to the optical pickup 10 to adjust focus in the absence of a refractive layer 112 on the disc; the height of the spindle was also raised. The HF (RF, quad sum) signal was amplified by the electronic circuitry in the RSL100 so that an oscilloscope display could be provided without adversely affecting the performance of the wobble tracking device. FIG. 13 presents a representative tracing, with the X axis displaying time and the Y axis displaying the magnitude of the quad sum signal.

FIG. 13 demonstrates that the red blood cell is directly visible as a high frequency, high amplitude event in the HF signal of a CD-R reader; for an analyte the size of a mammalian cell, no latex sphere or other exogenous signaling moiety is required to generate an analyte-specific signal.

Also evident from the oscilloscope tracing in FIG. 13 is that the deviation from the HF baseline is a double peak. Although red blood cells are well known to have a characteristic biconcave shape, we have observed this dual peak when latex spheres are used, as in Example 2, to report the presence of analytes. The dual peak appears to result from reproducible changes in reflectance as the laser traverses a sphere in the groove. Such reproducible electronic signatures may advantageously be used to identify and discriminate signals from variously dimensioned analyte-specific signal elements.

A further observation readily apparent from the oscilloscope tracing in FIG. 13 is that the baseline on either side of the signaling event is steady; that is, tracking of the wobble groove (here manufactured as an inverse image wobble groove) does not itself cause significant change in the quad sum signal.

The optical reader, in accordance with CD-R standard, maintained a constant linear velocity irrespective of the location being read on the disc, modifying spindle speed to lock a constant wobble frequency. Based upon the known linear velocity of the disc and the time increments marked on the oscilloscope tracing, each division on the oscilloscope tracing may be shown to correspond to a linear distance on the disc of 13 µm. As measured on the tracing shown in FIG. 13, the deviation in the quad sum signal baseline thus gives 10 µm as the approximate uncorrected size of the object in the direction of the tracking groove.

The actual size of the object is smaller. Prior calibration of the reader and oscilloscope using 3 µm latex spheres had given oscilloscope peaks reporting an apparent size of 5 µm, 2 µm wider than the actual object. This likely is accounted for by the 1.5 µm laser focus diameter at the first surface of the assay disc.

Taking into account the 2 µm difference between measured and actual size occasioned by the diameter of the laser at the disc surface, the event captured on the oscilloscope tracing in FIG. 13 as a high frequency, high amplitude deviation in quad sum signal reports an object size of 8 µm, in excellent agreement with the known 8 µm diameter of a human erythrocyte.

Figure 14:
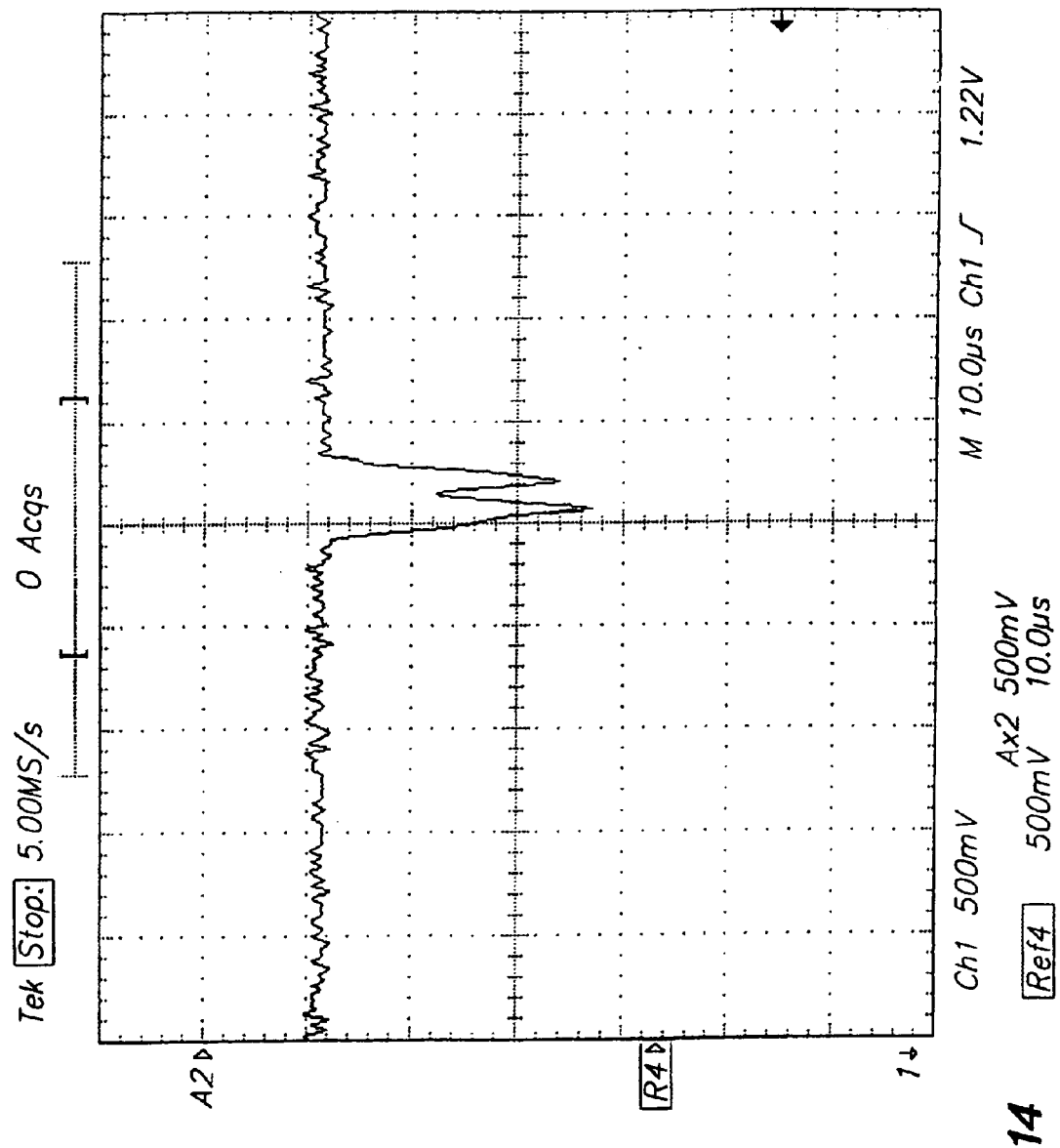
FIGS. 14–17 present digital oscilloscope tracings showing the analyte-specific perturbation in HF (quad-sum) signal obtained by an optical disc reader's trackable scanning over several distinct red blood cells immunospecifically adherent to the surface of a first surface trackable RBC-specific disc, with X axis displaying time and Y axis displaying the magnitude of the quad sum signal.
Figure 15:
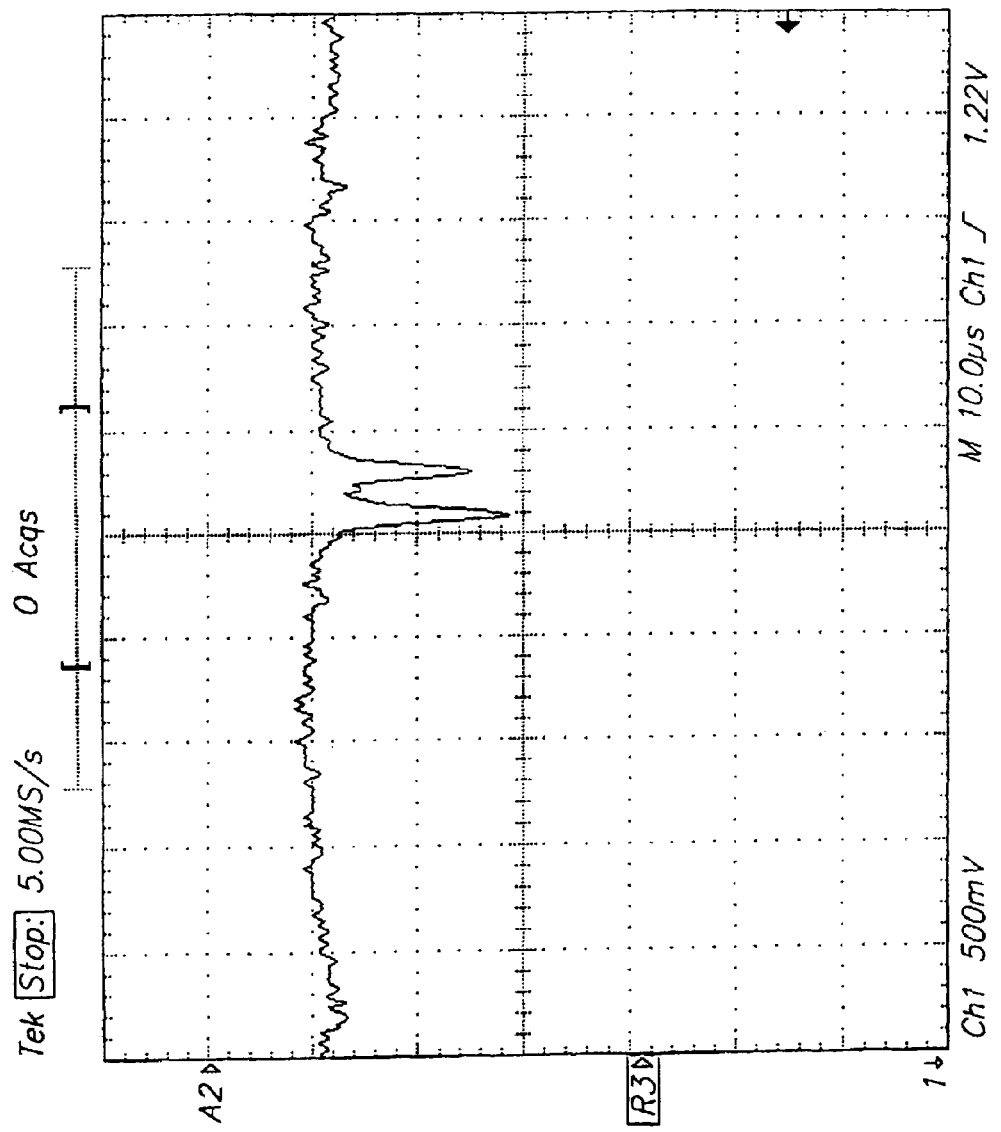
Figure 16:
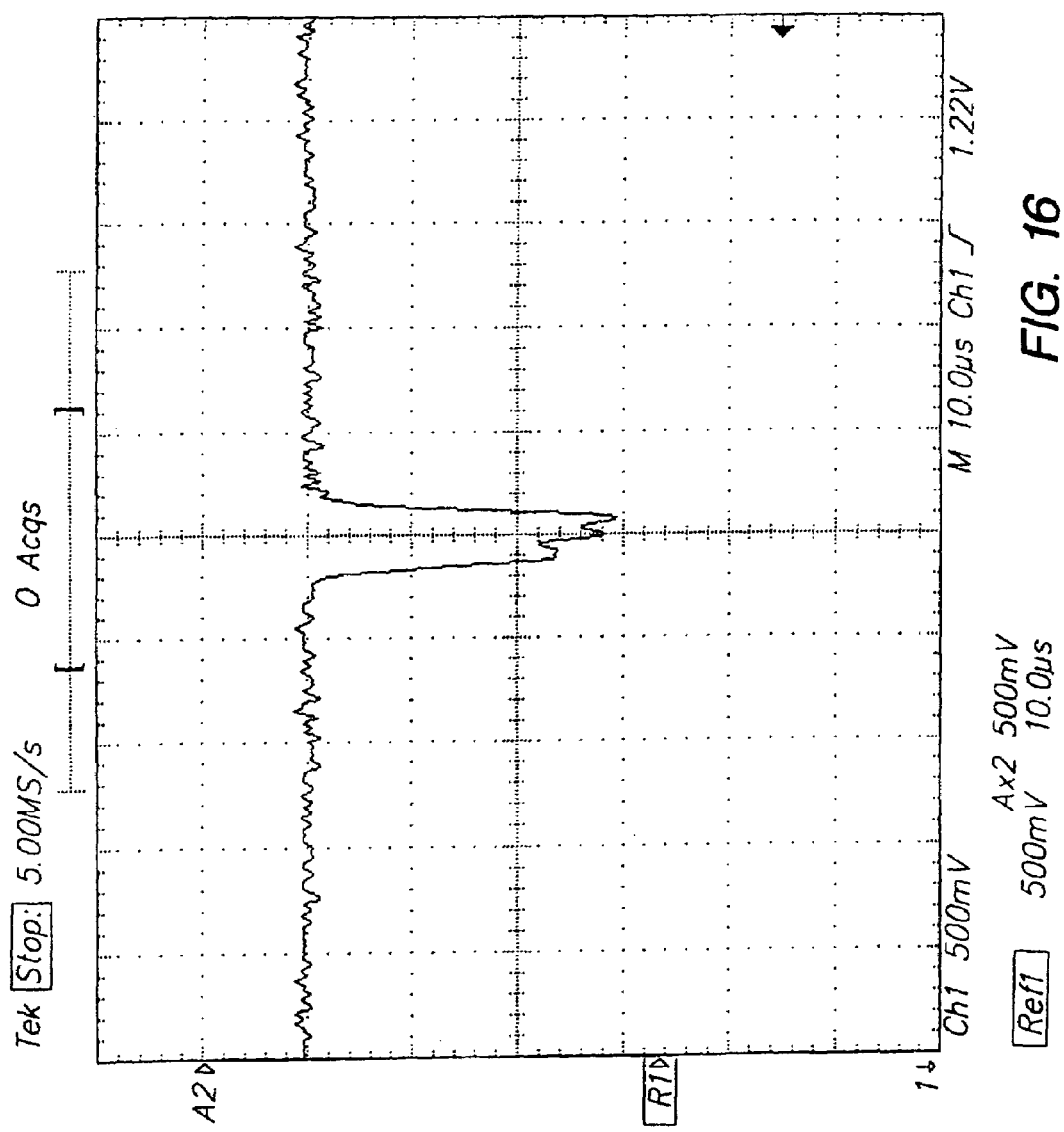
Figure 17:
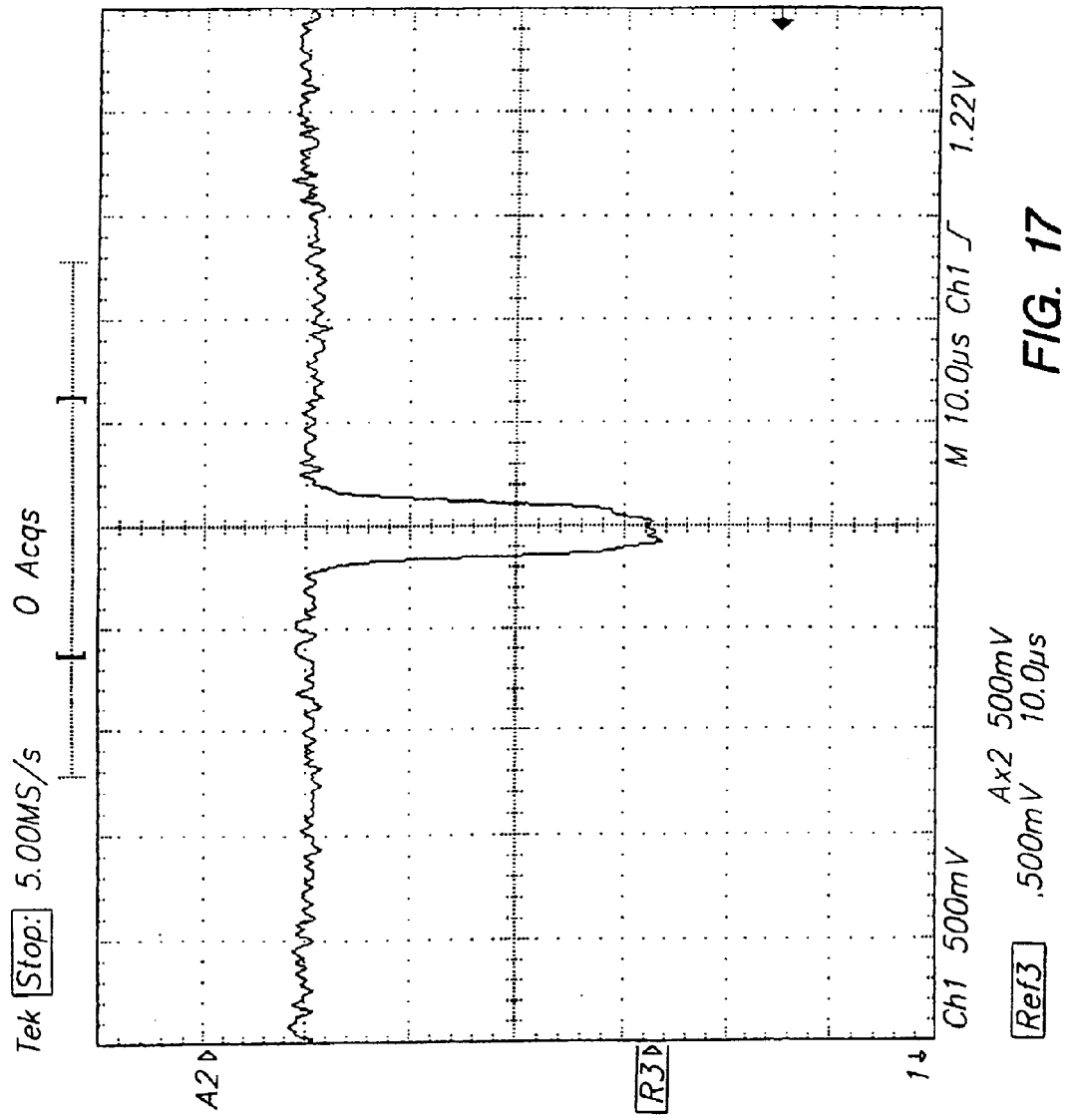

FIG. 14 presents another oscilloscope tracing of the HF event signaled by detection of a separate red cell on the same disc. The biphasic peak is more pronounced. FIGS. 15–17 are additional examples.

Figure 18:
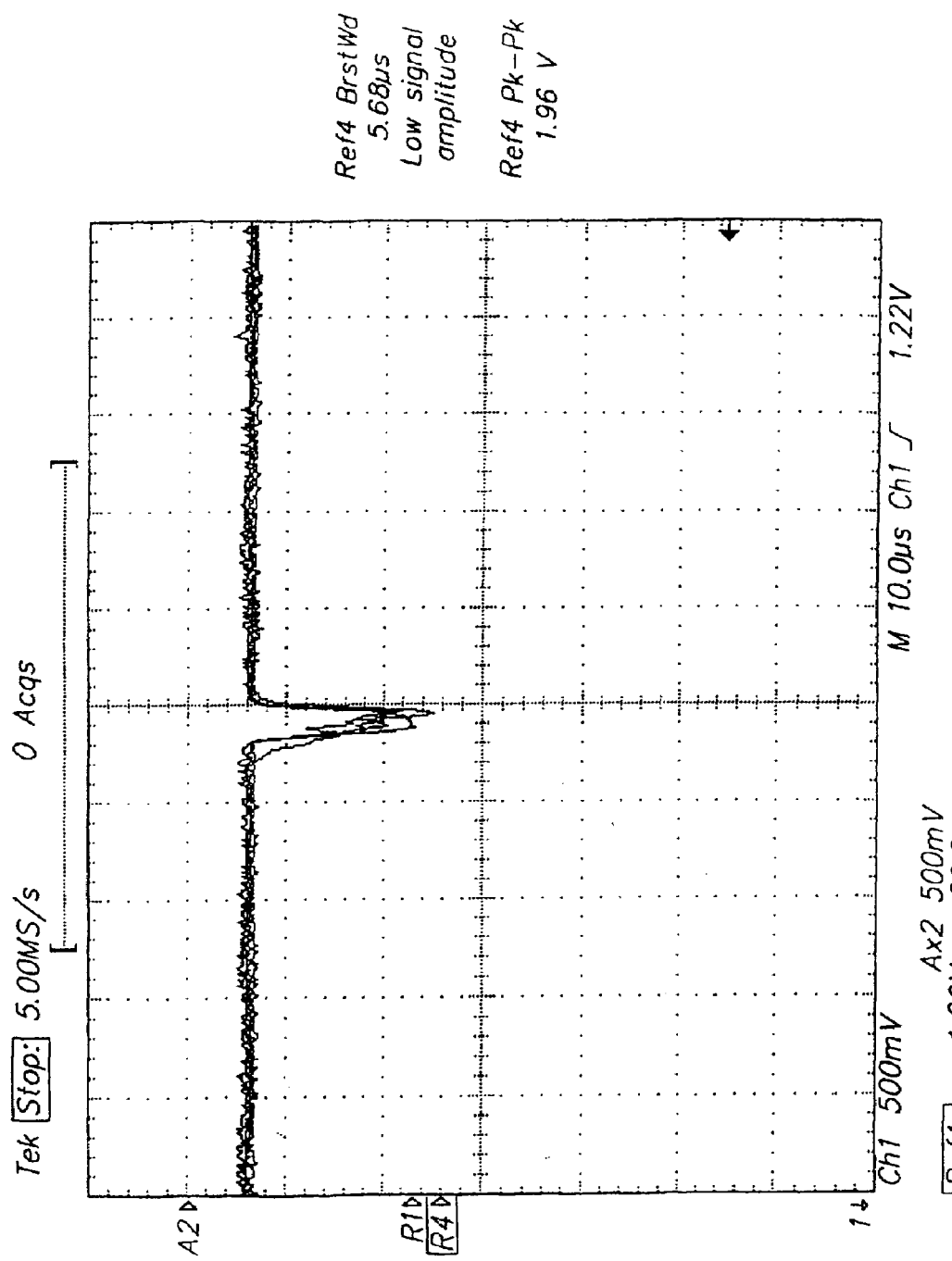
FIG. 18 is a digital superimposition of multiple events acquired from the same disc, demonstrating the reproducibility of the size and shape measurements over several different red blood cells immunospecifically adherent to the disc.

FIG. 18 is a digital superimposition of multiple events acquired from various areas of the same disc, demonstrating the reproducibility of the size and shape measurements over several different red blood cells immunospecifically adherent to the disc.

In summary, Examples 1–3 demonstrate that micron-sized analyte-specific signal elements disposed upon the first surface of a single-layer disc constructed according to the principles described herein may be detected, measured, and characterized by a minimally-modified standard optical disc reader. The operational features of the disc, including tracking features, are detected concurrently with and readily discriminated from analyte-specific signals using a single optical pickup. Example 2 particularly demonstrates that immunoassays for small molecule analytes may readily be adapted to detection using this system; Example 3 demonstrates that cell counting and cellular analysis are also readily accomplished.

Example 7, in turn, demonstrates that assays based upon nucleic acid hybridization may similarly be adapted to detection using the trackable optical disks of the present invention.

As set forth in detail in Example 7, solution phase hybridizations were performed in parallel at various concentrations of target nucleic acid in the presence of constant amounts of: (1) a single-stranded nucleic acid probe complementary in sequence to a first portion of the target ("3' probe") and (2) a single-stranded nucleic acid probe complementary in sequence to a second portion of the target ("5' probe"). The 3' probe was further conjugated to a paramagnetic bead and the 5' probe was further conjugated to biotin: the paramagnetic bead serves to permit magnetic separation and purification of the partially duplexed target, and further permits direct detection by an optical disk reader; the biotin moiety of the 5' probe permits capture of the partial duplex by streptavidin applied to the metallic surface of a first surface disk of the present invention.

Figure 36:
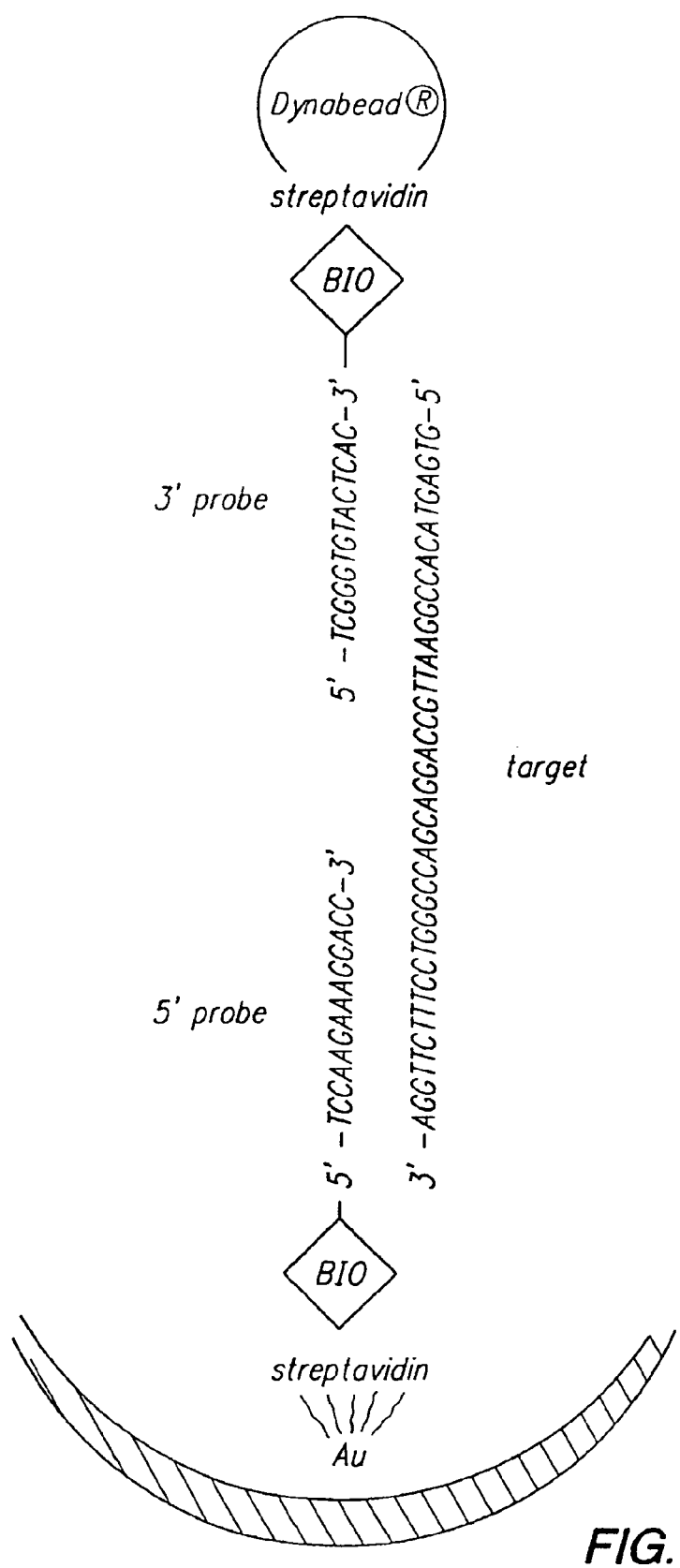
FIG. 36 schematizes a nucleic acid-based analyte-specific assay site constructed on a trackable disk of the present invention, in which specific adherence of a single 2.8 $\mu$m sphere to the disk surface is driven by nucleic acid sequence complementarity.

FIG. 36 schematizes the assay site at the time of visualization. Directly adherent to the gold surface of the trackable optical disk is a coating of streptavidin, bound by van der Waal's forces and by sulfur-gold bonds formed between free sulfyhydryls of the streptavidin protein and the gold surface of the disk. The streptavidin captures the biotin moiety of the 5' probe. The 5' probe, in turn, captures the target nucleic sequence by Watson-Crick complementarity with 14 nucleotides at the 3' end of the target. The target, in turn, captures the 3' probe through Watson-Crick complementarity of 14 nucleotides at its 5' end, thus tethering the Dynabead® to the disk.

Figure 37A:
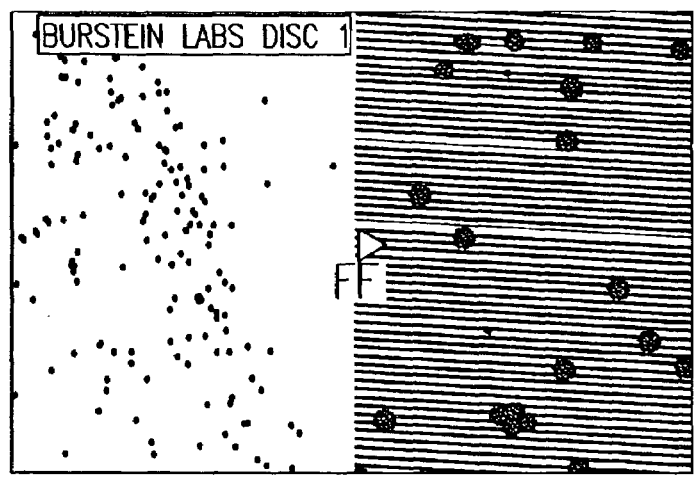
FIG. 37 presents light microscopic images of three disks, each at two magnifications, constructed using the assay geometry shown in FIG. 36, with FIG. 37A showing nucleic acid sequence complementarity-driven adherence of spheres to the disk surface at 20 femtomoles ($20 \times 10^{15}$ moles) target nucleic acid; with FIG. 37B showing nucleic acid sequence complementarity-driven adherence of spheres to the disk surface at 20 attomoles ($20 \times 10^{-18}$ moles) target nucleic acid.
FIG. 37C showing nucleic acid sequence complementarity-driven adherence of spheres to the disk surface at 20 zeptomoles ($20 \times 10^{-21}$ moles) target nucleic acid.
Figure 37B:
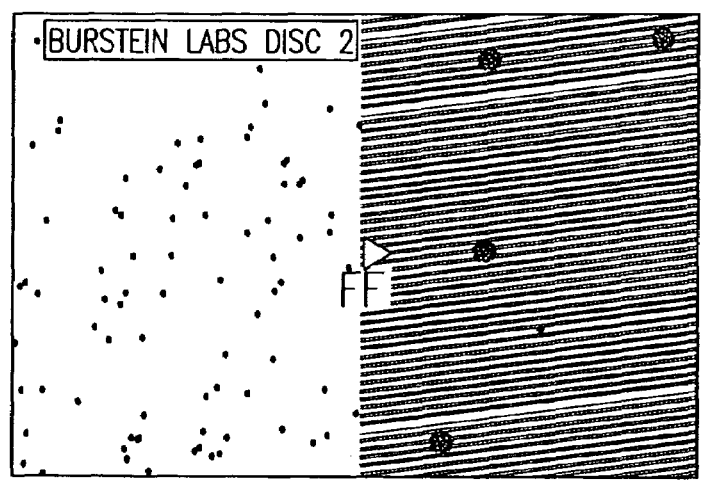
Figure 37C:
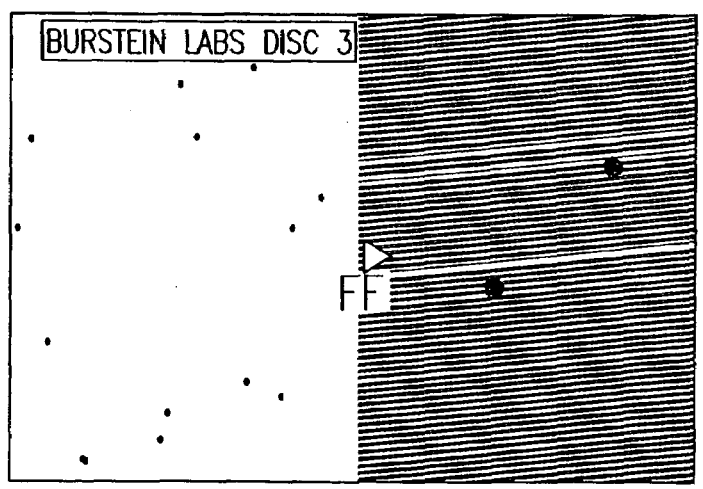

FIG. 37 presents light microscopic images taken separately of assay disks 1–3, each disk at two magnifications: adherent spheres and the wobble grooves are clearly visible in the higher magnification panels of all three. Increasing numbers of adherent beads are clearly seen with increasing amounts of nucleic acid target, with disk 3 (FIG. 37C) showing complementarity-driven adherence of spheres to the disk surface at 20 zeptomoles ($20 \times 10^{-21}$ moles; $12 \times 10^3$ molecules) nucleic acid target, with disk 2 (FIG. 37B) showing complementarity-driven adherence of spheres to the disk surface at 20 attomoles ($20 \times 10^{-18}$ moles; $12 \times 10^6$ molecules) nucleic acid target, and disk 1 (FIG. 37A) showing complementarity-driven adherence of spheres to the disk surface at 20 femtomoles ($20 \times 10^{-15}$ moles; $12 \times 10^9$ molecules) of nucleic acid target. No beads were observed on the surface of either control disk (not shown). It will be appreciated that FIG. 37 presents, in each image, only a portion of the assay field.

Example 7 thus demonstrates that nucleic acid hybridization-based assays may readily be adapted for detection by the trackable optical disks of the present invention. Example 7 further demonstrates that magnetic beads, long used for separation and purification in molecular biology, may now additionally be used directly for signaling, providing an efficient system for separation, purification, and detection without the obligate further labeling of the nucleic acid with radionuclides, fluorophores, enzymes, chemical moieties, or the like.

Co-owned and copending application Ser. No. 08/888,935 filed Jul. 7, 1997 and Ser. No. 09/120,049 filed Jul. 21, 1998, incorporated herein by reference, describe a variety of other approaches and chemistries that would permit adaptation of existing assays to detection using the trackable optical discs of the present invention.

Single Data-Layer Disc Variants

As will be understood by one skilled in the art, numerous variations of the single data-layer analyte-specific optical disc 130, with or without a removable cover, may be manufactured. Preferred embodiments are discussed below.

Holographic Operational Features

Figure 20:
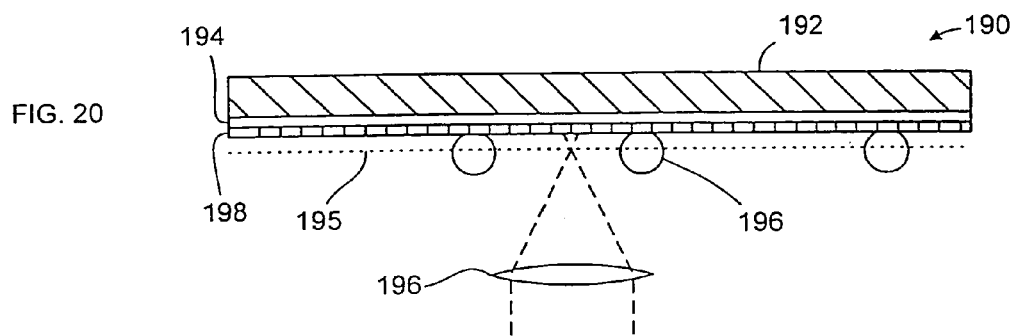
FIG. 20 shows a preferred embodiment of the single layer trackable analyte-specific optical disc of the present invention, with the disc's operational features encoded in a reflective hologram reflecting an image of the disc's tracking features in a plane confocal with analyte-specific signal elements disposed upon the first surface of the disc.

Referring now to FIG. 20, a preferred single data layer embodiment is shown. In this embodiment, the operational features of the disc are encoded in a reflective hologram rather than by physical impression in the disc substrate.

Disc 190 comprises disc substrate 192, hologram 194, and transparent protective coating 198. Hologram 194 is a reflective hologram containing the operational features required by disc 190. Specifically, when a laser is reflected from hologram 194, it will appear as though a wobble groove of correct orientation is present at hologram image plane 195.

In a preferred embodiment, the hologram image plane 195 is laser-proximal to the hologram physical plane 194 and is substantially confocal with analyte-specific signal elements 196 disposed upon the first surface of the assay disc. The laser is focused, as before, on the plane shared by the analyte-specific signal elements and the operational features (here, an image of a wobble groove), permitting concurrent and discriminable acquisition of operational data (specifically, tracking data) and analyte-specific data.

It should be apparent, of course, that optimizing laser focus on the image plane of the hologram—confocal with the analyte-specific signal elements—necessitates that the laser be less tightly focused on the hologram's physical plane. Yet the very nature of holographic imaging not only tolerates such "error" but benefits therefrom. As is well known in the optical arts, each portion of hologram's physical surface can generate the entirety of the image that is interferometrically encoded thereon; however, as the illuminated portion decreases in size, the resolution degrades. Conversely, the larger the portion of the hologram illuminated, the better the image. Thus, the larger the illuminating laser spot, the better the image of the disc's operational features—in preferred embodiments, a wobble groove—will be.

As would be understood by the skilled artisan, the hologram image plane may also usefully be projected so that it is no longer exactly confocal with the analyte-specific signal elements, so long as the operational features, such as a wobble groove, are concurrently detectable with the analyte-specific signals. Thus, the image may be projected not only laser-proximal to the hologram's physical plane, but also laser-distal thereto.

Furthermore, although shown as integral to disc 190, hologram 194 may be removable. This permits hologram 194 to be mass-produced using existing high-speed holographic printing processes. Furthermore, depending on the application, hologram 194 may also be reversibly attachable to disc substrate 192, potentially permitting reuse of substrate 192. The holographic single data layer embodiments of the trackable assay discs of the present invention permit low cost mass-production of discs readable by the wide installed base of optical readers.

As in the other, physically embossed, embodiments of the single data layer discs of the present invention, disc substrate 192 need not meet the optical requirements of standard transparent disc substrate 112, inasmuch as disc substrate 192 lies laser-distal to the data planes.

Also as in the embodiments above-described in which the operational features are embossed and reflectively coated, the holographic embodiments may usefully include a laser-proximal, nonintegral cover that assists in focus. In the holographic embodiments, the focus is thereby adjusted onto the hologram image plane.

Zoned CLV

Both the physically-impressed and holographically-encoded single data layer discs described herein above may usefully employ substantially radial tracking schemes other than a CD-R standard wobble groove. In particular, first surface trackable analyte-specific assay discs may be built in accordance with the principles of the present invention with a "Zoned Constant Linear Velocity" (ZCLV) format for laying out regions of the disc. Briefly described here, the ZCLV format, as is well known in the art, is detailed in various industry standards, including the DVD-RAM specification.

Figure 21:
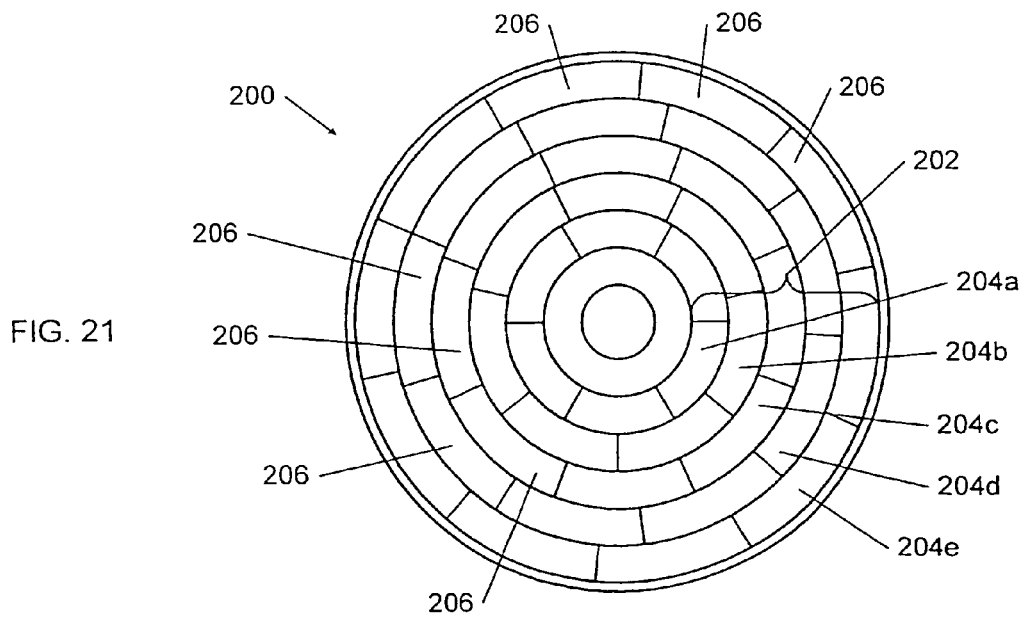
FIG. 21 shows a simplified top side view of the physical organization of a disc constructed to the zoned constant linear velocity (ZCLV) standard.

As shown in FIG. 21, a top side view, ZCLV disc 200 has data area 202 that is divided into multiple zones 204a–204e. Although only five zones are shown, actual ZCLV format discs may have different numbers of zones. The DVD-RAM ZCLV format, for example, has 24 zones within its rewritable data area.

Each of zones 204a–204e is divided into multiple sectors 206. Inner zones have fewer sectors than outer zones, since the radius of inner zones is less than the radius of outer zones. The layout of the disc is arranged so that header information for each block of data on each track (i.e., each turn of the spiral) aligns radially within each sector. This permits an embossed, non-wobble header area to be used for each block of data, followed by a "wobbled land and groove" area in which data may be written.

In use, the optical disc reader may rotate a ZCLV disc at a constant rate within each zone, and still maintain a substantially constant data rate within a zone. For inner zones, the disc must be rotated quickly to maintain an overall substantially constant data rate, while for outer zones, the disc may be rotated at a lower rate.

Figure 22:
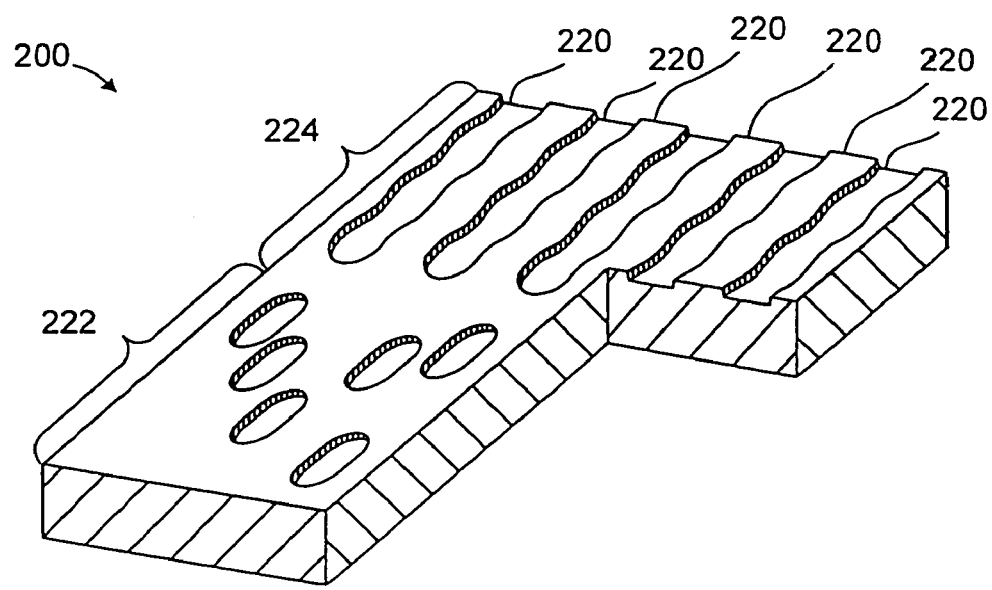
FIG. 22 shows an enlarged perspective view of one of the sectors of the ZCLV disc of FIG. 21.

FIG. 22 shows an enlarged perspective view of a portion of one of the sectors of ZCLV disc 200. As can be seen, multiple tracks 220 are arranged radially within the sector, so that each track has header information for a block of data embossed in "pre-groove" area 222. Data for each track may then be recorded both within the wobble grooves, and on the wobbled land areas between the grooves within "wobbled land and groove" area 224.

Figure 23:
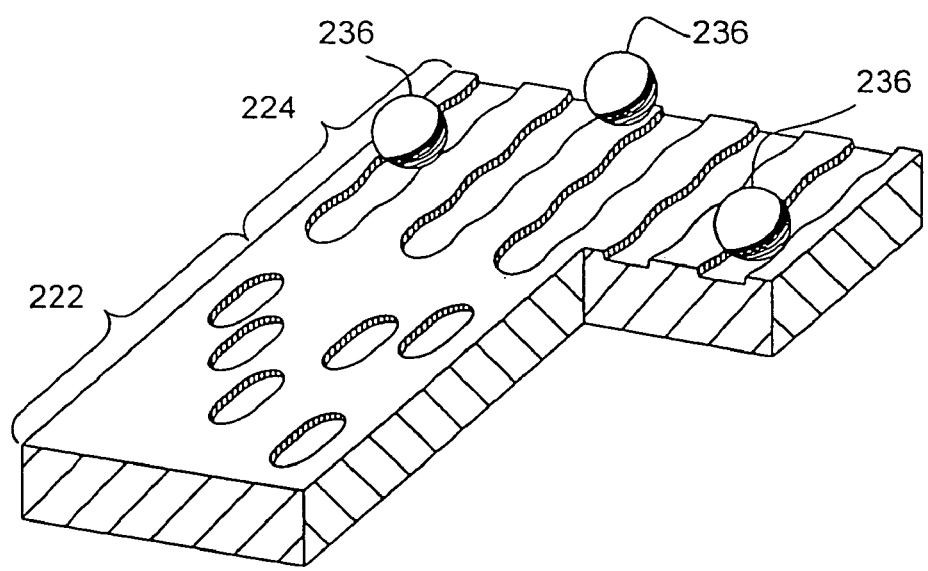
FIG. 23 shows analyte-specific signal elements disposed upon wobbled land and groove area of the sectors on a ZCLV first surface analyte-specific disc.

For use as an assay disc in accordance with the present invention, analyte-specific signal elements 236 may be deposited within wobbled land and groove area 224 of sectors on the disc, as shown in FIG. 23. Since, within each sector, wobbled land and groove area 224 forms a continuous region, an assay disc using a ZCLV format can use each of the sectors to perform a different assay. The embossed header information in pre-groove area 222 can be used to store information identifying the assay within the wobbled land and groove area. The wobbled lands and grooves within the wobbled land and groove area, and the embossed data tracks in the pre-groove areas, satisfy the functional requirements of an optical disc reader.

As suggested above, aspects of the various digital versatile disc (DVD) standards may usefully be employed in the practice of the single data layer embodiments of the present invention. The present invention is, therefore, not limited to existing CD-type discs or CD standards. In addition to the specific utility of the ZCLV format for multiassay discs discussed above, it will be readily apparent that the smaller feature size and lower wavelength laser specified in the DVD standards permit a higher density of analyte-specific signal elements to be detected with higher spatial discrimination than is possible using CD standards. Furthermore, the dual data layer DVD format offers unique advantages, further discussed in sections below.

Disk Covers

The CD-R reader used in Examples 2 and 3 herein had been modified by addition of focusing lens 17 to adjust the drive's focus to account for the absence of a laser-proximal refractive substrate as the first surface of the analyte-specific disk. An alternative approach, which will often be preferred, adjusts the disc itself, rather than the disk reader. In this latter approach, a laser-refracting member is attached to the laser-proximal side of the disc as a cover; the cover serves to refract, and thus to focus, the incident light on the disc's reflective surface. Suitably designed, the cover obviates alteration in the drive's focusing optics. The data presented in FIG. 40 were obtained, without assistance of a further focusing lens 17, using such a cover.

Figure 19:
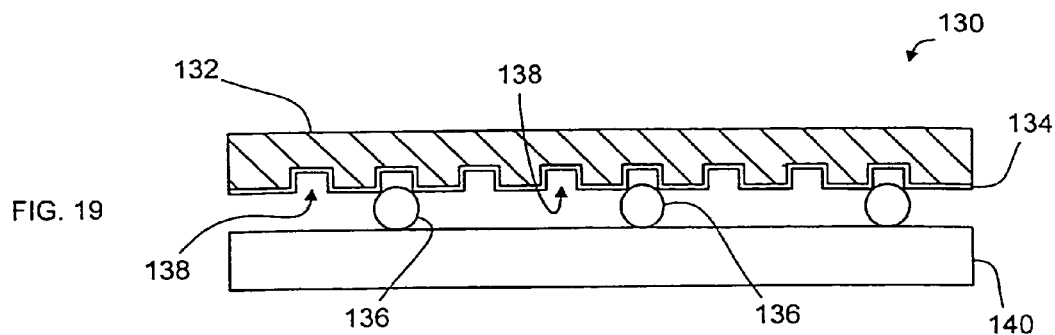
FIG. 19 is a side cross sectional view of a single layer trackable analyte-specific disc assembled with a nonintegral laser-proximal, laser-refractive cover.

Such an approach is depicted in FIG. 19. By convention herein, laser light is incident from below in this side cross-sectional view. Disc 130 comprises disc substrate 132 and reflective layer 134, upon which analyte-specific signal elements 136 are disposed. Reverse image wobble groove 138, impressed in substrate 132 and coated by reflective layer 134, is indicated. Also shown is nonintegral cover 140. One embodiment of such a cover is further shown in top perspective view in FIG. 35.

Preferably, the disc assembly (disk plus attached cover) is so dimensioned as to approximate the size standard for a unitary optical disc, that is, 1.2 mm in depth and either 80 mm or 120 mm in diameter. However, it is also contemplated that the disc assembly may vary from this size. In these latter cases, despite variance from the physical size specifications of the optical disk standards, the assembly must still prove capable of meeting the necessary optical and mechanical requirements of the drive: among other requirements, the laser must correctly focus on the disk's operational plane, the disk assembly must clamp properly onto the spindle, and the disk assembly must not vary so far from standard weight that the drive's motor cannot maintain proper rotational speed.

Example 6 presented herein below describes the manufacture of polycarbonate covers approximately 1.17 mm thick, but otherwise dimensioned identically to a standard 120 mm disk. The covers were manufactured from polycarbonate to take advantage of the well known optical qualities of polycarbonate and to take advantage of the ready availability of devices adapted to its molding. As further discussed below, however, other plastics may advantageously be used in constructing disk covers.

The single data layer disks manufactured as in Example 5 are 1.2+/−0.05 mm thick; the covers manufactured as in Example 6 are about 1.17 mm thick. Assembled, the two approximate 2.4 mm in depth, outside the maximal physical thickness provided by the Red Book standard (1.1–1.5 mm for all layers combined). Although this does not present an optical problem—the optical path remaining within specification—it seemed possible that this increased physical depth might present difficulties in the clamping of the disk assembly in the drive. Furthermore, the assembled disk and cover exceeded the weight of standard, unitary disks.

Empirically, however, we found that the assembly both clamped and spun without problem. The data presented in FIG. 40 were obtained using disks manufactured according to Example 5 and assembled, before reading in an optical disk drive, with a cover manufactured in accordance with Example 6. The cover provided sufficient assistance to focusing to obviate addition of a further focusing lens 17 to the drive's optical pickup in producing the data set forth in FIG. 40.

Although a nonintegral member is presently preferred as a laser refracting disk cover, an integral cover, hingeably or otherwise moveably or modifiably attached, may also be used. Nonintegral covers may be reversibly (removably) or irreversibly attachable to the disk, depending on desired usage.

Figure 40:
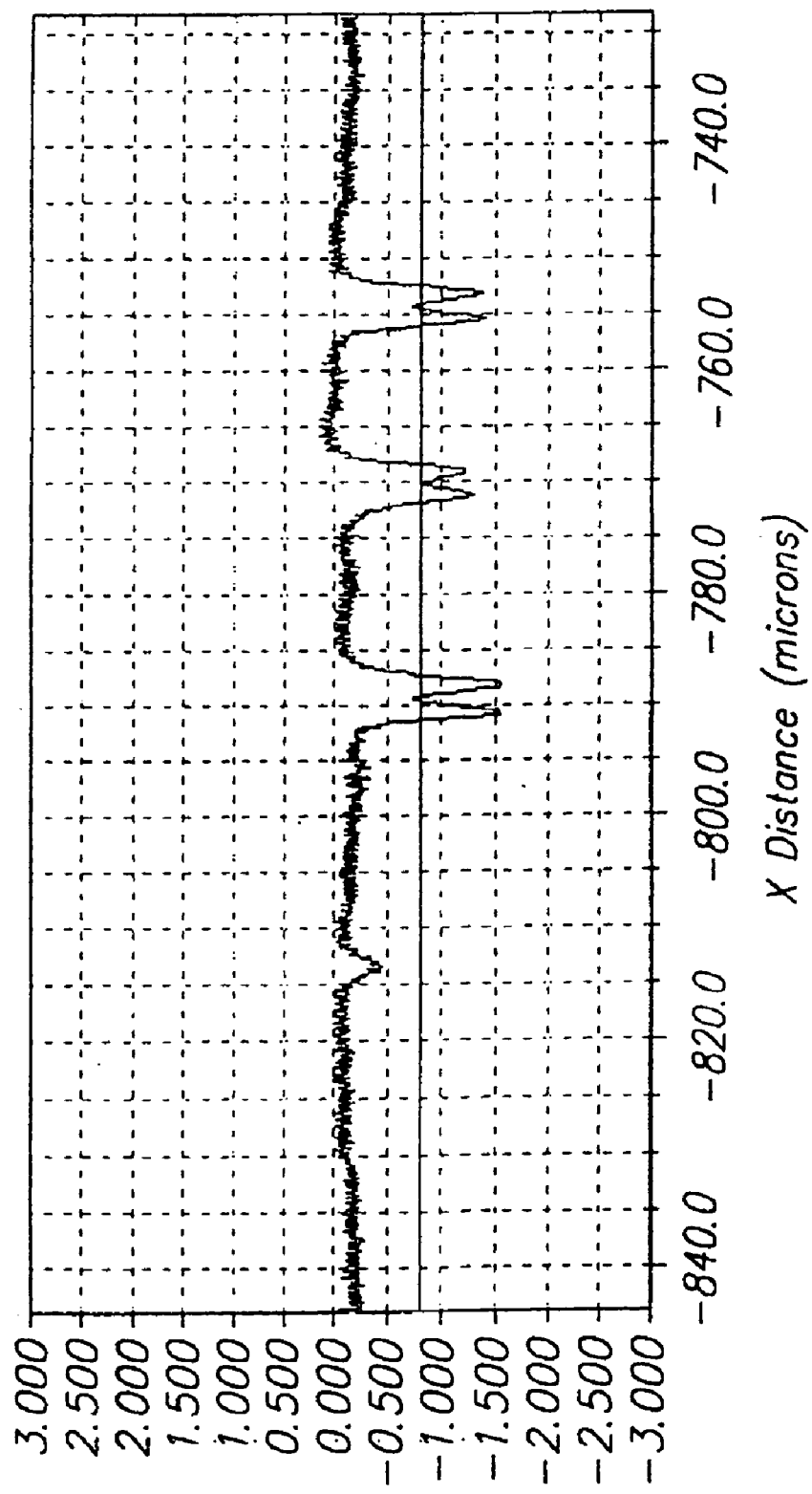
FIG. 40 shows the electrical response reported in the HF signal along a single one of the tracks that passes through the area of the disk shown in FIG. 39.
Figure 41B:
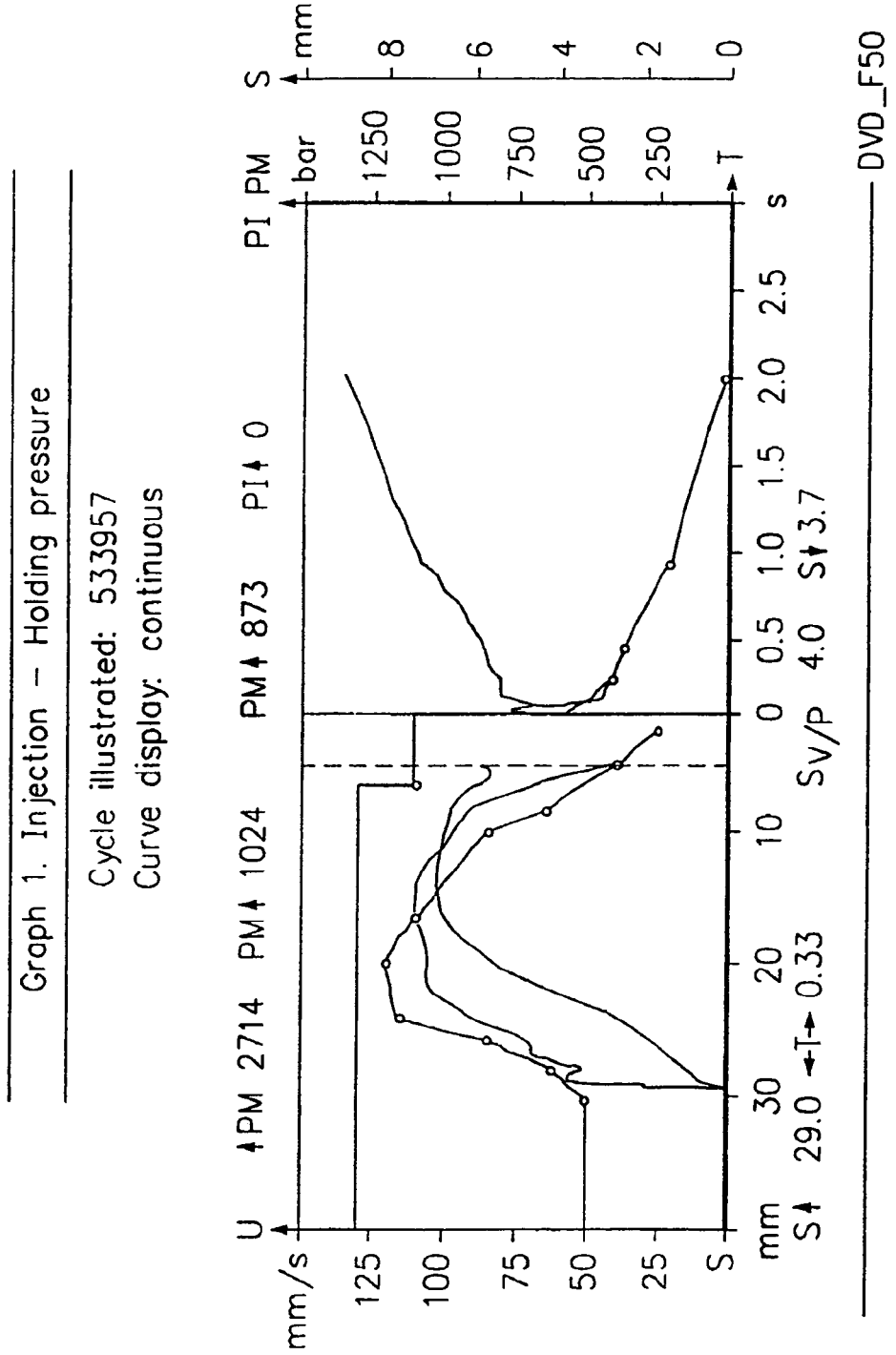
FIG. 41 presents the mold settings used in the manufacture of the disks described in Example 5, and shown in FIGS. 31, 32, 37, 38 and 39.

To generate the data presented in FIG. 40, a nonintegral polycarbonate cover manufactured as in Example 6 was affixed irreversibly to disks manufactured according to Example 5. Two to three small drops of methylethylketone (MEK), which partially dissolves the polycarbonate and renders it tacky, were applied to the disk's clamping ring 142. A commercially available paint stripping grade was used. The cover was then pressed gently against the disk for about 30 seconds. The MEK permanently affixes the cover to the disk at the clamping ring; at the outer diameter of the assembly, the disk and cover remain closely apposed but unattached.

The optical and mechanical requirements of the system require that the disk and cover be assembled in close radial registration to prevent the disk from going out of round; eccentricity during rotation could prevent the servo from locking the tracking signal.

To ensure proper registration, the analyte-specific disk and matching nonintegral cover will preferably have structural features that intermesh and/or interlock. In one preferred approach, the cover will circumferentially overlap the edge of the disk. The prototypical covers manufactured according to Example 6, lacking such engineered features, were centered on the disk as follows.

In initial efforts, a plastic tray from a CD holder ("jewel case") was used to immobilize the analyte-specific trackable optical disk. MEK was applied with dropper to the disk's clamping ring and the cover was then placed on top and pressed into place. The deformable spindle in the jewel case held disk and cover in sufficiently close registration to permit successful assembly. Subsequent to these efforts, a simple, dedicated, device was fashioned to accomplish the registration.

The disk and cover manufactured according to Examples 5 and 6, respectively, each have a stacking ring 144 that delimits the clamping ring 142 from data area 146. The stacking ring, which protrudes from one side of the disk (and cover) but not the other, is designed to keep adjacent disks, when stacked, from approaching one another closely enough to scratch. Accordingly, the disk and cover were assembled with stacking rings facing away from one another.

MEK was used in the experimental examples herein because it conveniently and quickly permits attachment of polycarbonate structures. Other glues may also be used, and may be required where plastics other than polycarbonate are used for the cover and/or disk. Furthermore, MEK frosts the polycarbonate surface; although its application to the clamping ring 142 presents no optical problems, lying as it does outside the data area, MEK cannot be used as readily if bonding is desired within the data area, closer to the disk's outer diameter. For those purposes, glues that are more optically suitable would likely be preferred; among such glues, those typically used to adhere the separate laminae in DVD disks (see below) may prove preferable. One such glue is described in U.S. Pat. No. 5,879,774, incorporated herein by reference. Co-pending and co-owned U.S. patent application Ser. No. 09/263,972 by Virtanen, entitled "Monomolecular Adhesion Methods for Manufacturing Microfabricated Multilaminate Devices," incorporated herein by reference, presents yet other alternatives to standard glues that may prove particularly useful in affixing laser refracting covers to trackable optical disks with analyte-specific signal elements.

Polycarbonate was chosen for the covers exemplified herein to take advantage of the well known optical qualities of polycarbonate and the ready availability of devices adapted to its molding. However, other plastics may advantageously be used in constructing disk covers. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof. Glass may also be used.

As noted above, the analyte-specific signal elements are preferably disposed confocally with the operational features of the disk in the single data layer disks of the present invention. This permits the laser to focus concurrently on the analyte-specific signal elements and operational features of the disk. Furthermore, when signal elements fall directly into the operational features—in the disks exemplified herein, into the wobble groove—signal is maximized.

It will be understood, however, that the analyte-specific signal elements and the operational (particularly, tracking) features need not be in the identical focal plane—it suffices that the signal elements and operational features be sufficiently confocal as to permit the disc reader's optical head to detect them both.

Thus, analyte-specific signal elements may be disposed upon the laser-distal (that is, disk-proximal) side of the cover rather than, or in addition to, on the disk surface itself. This presents several significant advantages.

First, disposing the analyte-specific signal elements on the plastic increases dramatically the chemistries that may be used to affix the signal elements to the surface. Although gold-sulfur bonds prove widely adaptable—as demonstrated by the adherence of antibodies (Example 2), adherence of cells (Example 3), and attachment of nucleic acids (Example 7)—plastic presents a far wider selection of available attachment chemistries.

Second, although the gold surface may be patterned to present discrete sites for such attachment, plastic surfaces may even more readily be derivatized to present chemically reactive groups in spatially defined patterns; these patterns of reactive groups, in turn, facilitate the application of analyte-specific signal elements in spatially addressable patterns.

Some of these patterns, and their advantages, are described in co-owned and copending U.S. patent application Ser. No. 08/888,935, filed Jul. 7, 1997 and Ser. No. 09/120,049, filed Jul. 21, 1998, incorporated herein by reference. Among the advantages discussed therein is the ability to array signal elements in patterns that report analyte concentrations across a wide dynamic range.

Other spatially-defined and spatially-addressable patterns readily suggest themselves. For example, the utility of arraying nucleic acids in spatially addressable formats on other substrates, such as silicon chips or glass slides, is well known. Furthermore, analyte-specific elements placed closer to the inner diameter of the disk are read at the outset of disk motion; analyte-specific elements placed progressively further from the inner diameter are read after progressively greater rotational delay. In nonequilibrium analyses, such patterning readily permits kinetic assays to be performed, with earlier reaction time points thus reported by assay sites disposed more peripherally on the disk.

Third, plastic surfaces may also readily be derivatized to present a desired degree of hydrophilicity, presenting further advantages over metal surfaces when the surface must uniformly be wet with an aqueous sample. In addition, the surface may be patterned with areas that present varying degrees of hydrophilicity and hydrophobicity.

Figure 38:
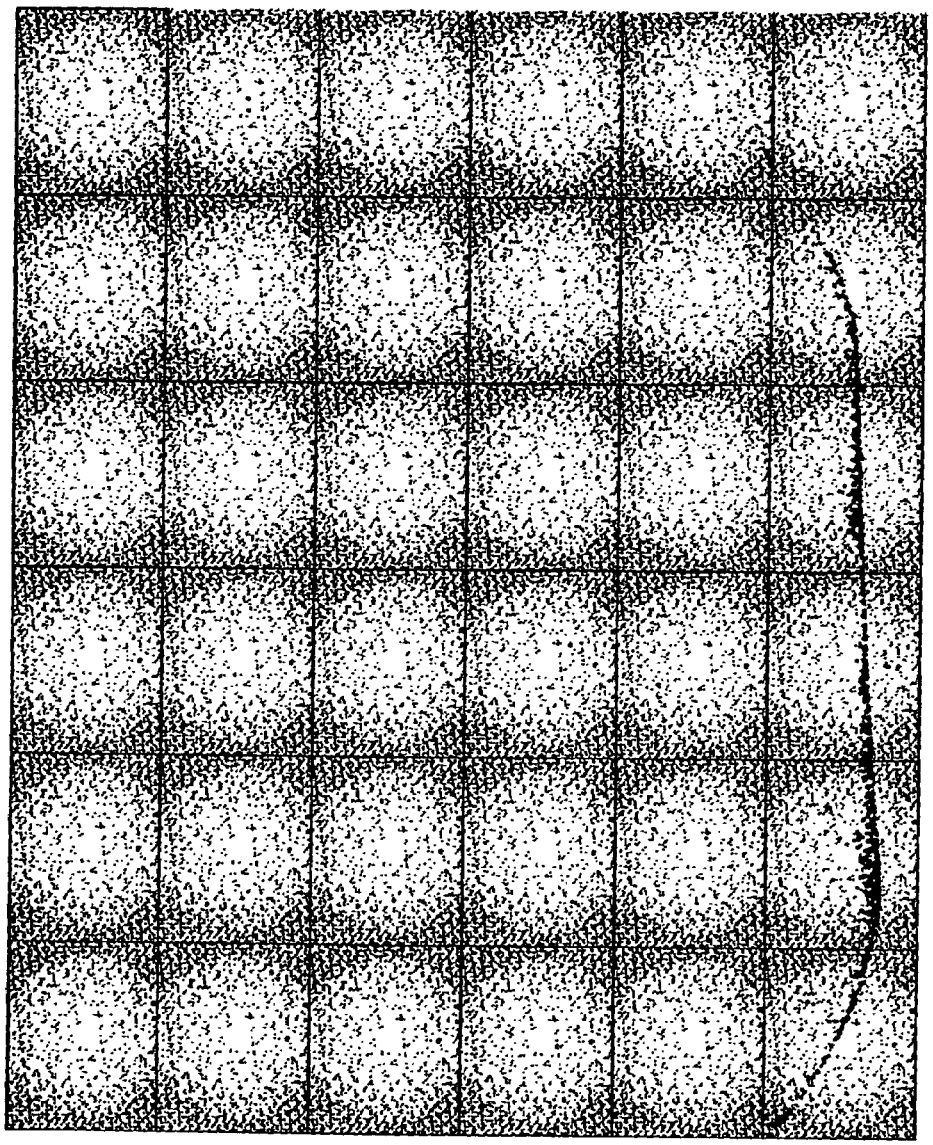
FIG. 38 is a two-dimensional composite of light microscopic images acquired at 300× magnification of the laser proximal surface of a disk identical in dimension to those measured by AFM in FIGS. 32 and 33, with 2.8 $\mu$m spheres electrostatically adherent to the metalized surface and manually aligned substantially along a groove.
Figure 39:
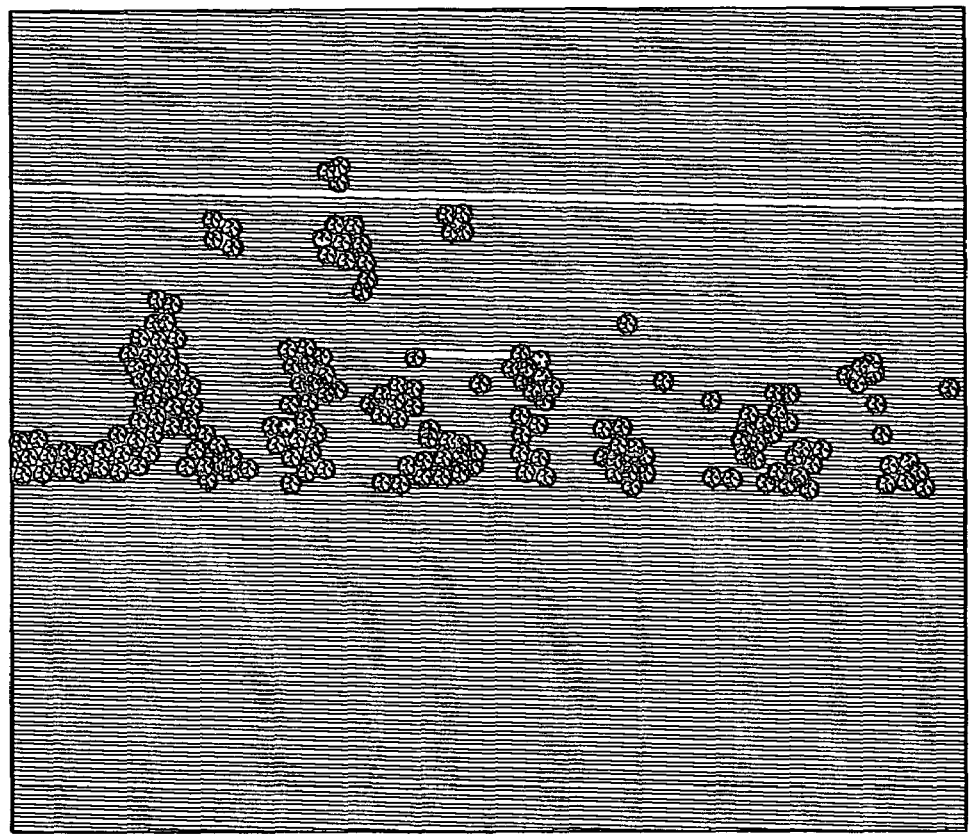
FIG. 39 is a higher magnification of a portion of the same disk as shown in FIG. 38.

Fourth, we have observed that the flow of fluids across the surface of the disk is influenced by, and at times impeded by, the wobble groove itself. This is demonstrated in FIG. 38, in which applied microbeads were easily caused to align along the groove. The flat surface of a disk cover presents no such impediment to the uniform flow of fluids across its surface.

Fifth, microfluidic components may readily be engineered into a plastic cover. Such microfluidics are described, inter alia, in co-owned and copending application Ser. No. 09/064,636, incorporated herein by reference.

And yet another advantage of disposing analyte-specific signal elements on a plastic cover is that, when the cover is both nonintegral and removable from the disk assembly, the trackable disk itself may be reused.

The cover—whether integral or nonintegral, removable or affixed permanently, with or without analyte-specific signal elements disposed thereon—serves other advantageous functions as well. It should be apparent that the reflective surface of discs of the present invention is exposed to air, in contrast to the reflective layer 114 of a standard disc. For this reason, nonoxidizable metals, such as gold, are preferably used in their manufacture, although aluminum or oxidizable metals may be used if covered by a thin layer of plastic. Being exposed, the reflective layer 134 of a first surface analyte-specific assay disc of the present invention is subject to abrasion, dust, and the like, that may degrade the signal obtainable therefrom. A plastic cover usefully protects the reflective surface, and the information thereon, from environmental degradation.

In addition, the cover serves to isolate infectious and other pathogenic agents from the user, a significant benefit in immunoassays for viral agents, such as HIV.

From an operational standpoint, application of removable cover 140 after signal elements 136 have been deposited on reflective layer 134 may compress the signal elements and drive them into wobble groove 138, further approximating the signal elements to the operational features of the disc, increasing signal.

Among plastics useful in construction of laser-refracting covers, polystyrene proves particularly useful: many current clinical assays are conducted on polystyrene surfaces. Standard microtiter dishes, used in enzyme-linked immunosorbent assays (ELISA) and radioimmunoassay (RIA), are made of polystyrene. A wealth of experience attends the conduct of clinical assays on polystyrene surfaces; such assays may thus readily be adapted to the present platform. Additionally, precision molding of polystyrene is presently practiced and readily accomplished.

As would of course be understood, the thickness of cover 140 would have to be adjusted to account for differences in the refractive index of the chosen plastic in order to focus the laser correctly on the disk's operational features. Such adjustments are well within the skill of the optical disk artisan.

It is also possible to achieve many of the advantages that are conferred by disposing analyte-specific signal elements on a plastic cover by coating the reflective surface of the disk with a thin, transparent layer of plastic, the analyte-specific signal elements then applied thereupon (i.e., on the most laser-proximal surface of this multilaminate structure). Polystyrene resin may readily be used for this purpose and then cured in situ. The resin is applied by vacuum deposition or by spin coating, then cured with UV light; the process is presently practiced in the art with polymethylacrylic, widely known as the "2P" process.

This latter approach confers the aforementioned advantages of disposing signal elements on plastic. Furthermore, it eliminates the boundary condition that otherwise exists between the cover and gold surface of the disk, permitting return from the disk operational plane of a more coherent light. However, because the layer is designed to be sufficiently thin as to place the signal elements substantially confocal with the disk's operational features, the layer is alone insufficient fully to assist in focusing. A cover, suitably dimensioned, may then additionally be used.

As noted above, adding a laser refracting cover to the disk to create a disk assembly restores second surface characteristics to the disk, permitting extra lens 17 to be removed from the optical pickup. The data presented in FIG. 40 were obtained using disks manufactured as in Example 5, with cover manufactured as in Example 6, read by a Ricoh 6200S CD-RW drive without the additional focusing lens required to assist focusing in Examples 2 and 3.

However, it should also be noted that the disks manufactured in Example 5 were optimized for first surface, rather than second surface, detection. As noted earlier, the depth of wobble groove 118 is typically chosen to optimize the tracking signal. Absent a laser-refracting first surface substrate, a wobble depth of approximately ⅛ the wavelength of the incident laser light will provide maximal signal: assuming that a "standard" 780 nm laser is used to read disc 130, wobble groove 138 should have a depth of approximately 97.5 nm.

Figure 31:
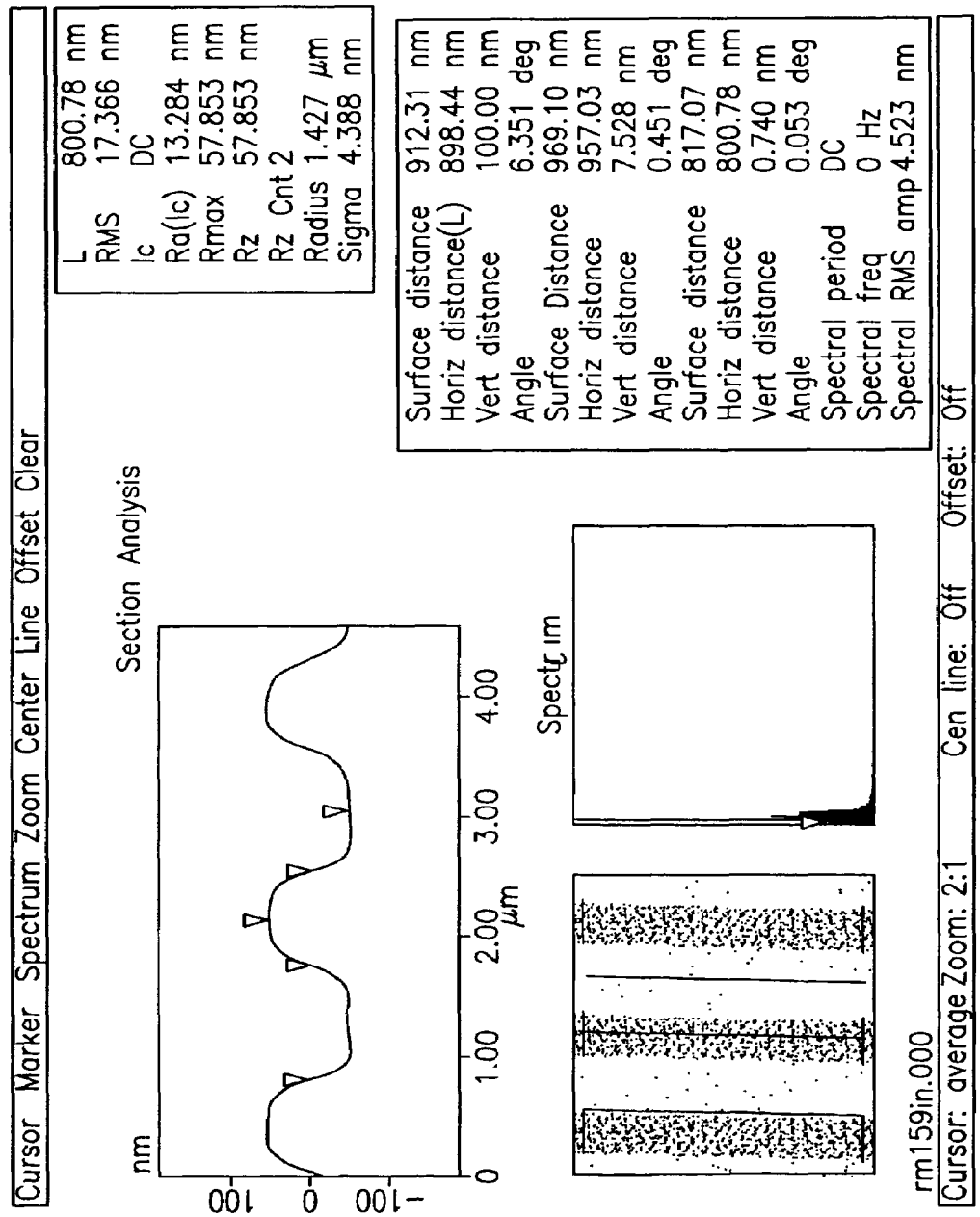
FIG. 31 presents data from atomic force microscopic examination of the inner diameter of a single data layer disk of the present invention, the disk further optimized for first surface detection relative to those shown in FIGS. 8–12, and having a reported groove depth of approximately 100 nm.
Figure 32:
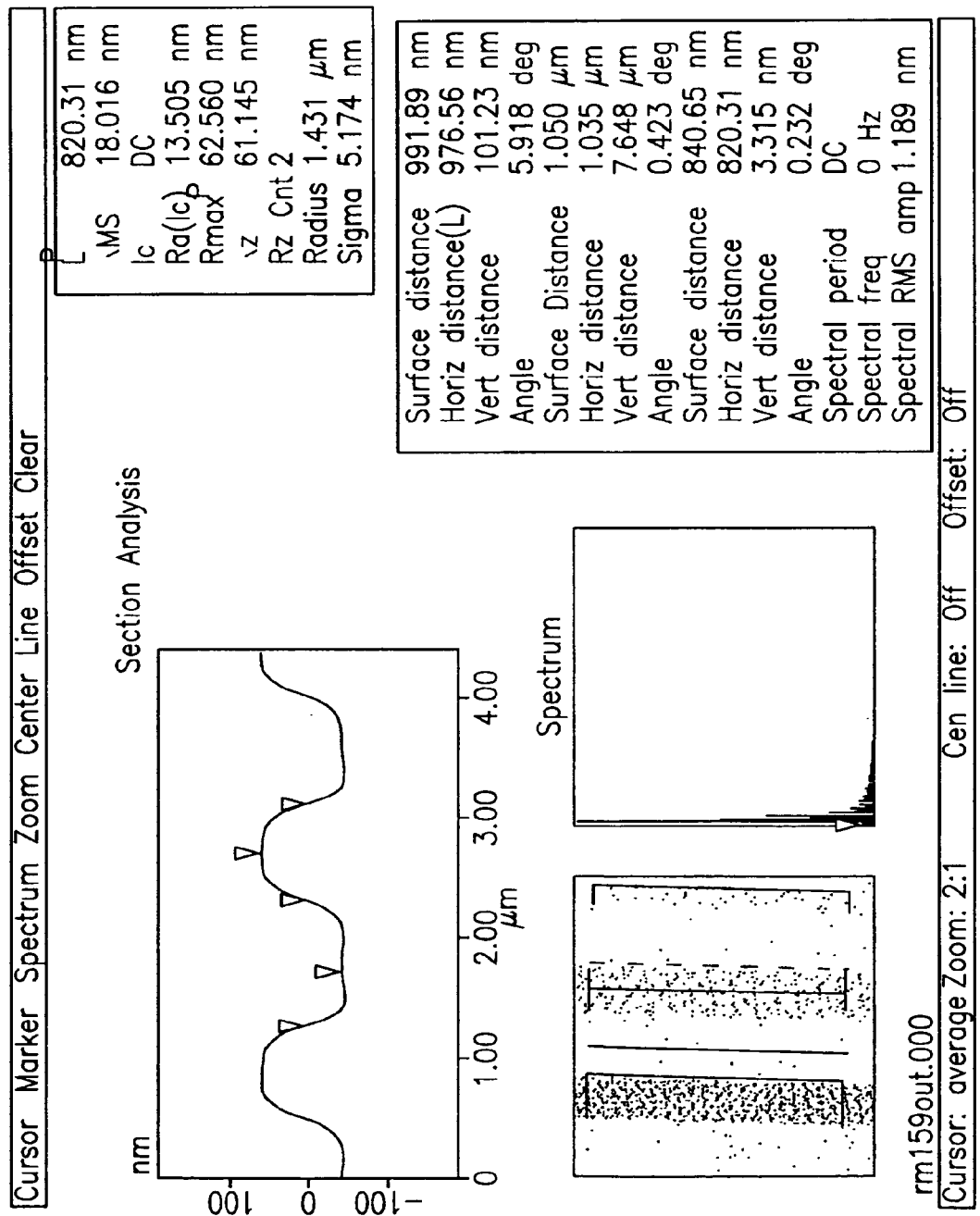
FIG. 32 presents data from atomic force microscopic examination of the outer diameter of a single data layer disk of the present invention, the disk further optimized for first surface detection relative to those shown in FIGS. 8–12, and having a reported groove depth of approximately 101 nm.

As shown in FIGS. 31 and 32, the disks manufactured in Example 5 and used to generate the data shown in FIG. 40 had groove depths of approximately 100 nm, near the optimum for first surface detection. Upon application of a polycarbonate cover, however, the depth is no longer optimal. With such a polycarbonate cover, the theoretic optimum for wobble groove depth would be approximately 62.5 nm.

Nonetheless, even with cover, the 100 nm groove depth permitted ready discrimination between signal and background, as evidenced by the electronic tracings shown in FIG. 40, demonstrating that the present approach to constructing single data layer trackable disks with concurrently readable analyte-specific signal elements is remarkably robust.

Cover 140 is optionally not present while assay sites are being prepared on the disc, sample applied, and further assay steps, as needed to develop the assay, are performed. Thereafter, to prepare the disc for reading, cover 140 is placed over reflective layer 134 and signal elements 136.

Wobble Detection, Data Acquisition and Data Storage

The wobble groove, which as a radial plane tracking scheme proves particularly advantageous for the concurrent and discriminable detection of tracking and analyte-specific signals in the single data layer embodiments of the present invention, was first added to the optical disk standard to permit user-directed recording of CD (and later DVD) media. As set forth in the relevant standard, colloquially termed the Orange Book, the wobble is detected by the recording device solely during writing of data to the disk; thereafter, tracking is accomplished by detecting the data so written along the wobble groove. The standard, and all existing implementations of the standard, thus contemplate that the wobble becomes redundant after writing.

Because the wobble is typically detected only during writing, a process that is unnecessary to most implementations of the present invention and a process that causes laser pulsing at amplitudes that might interfere with detection of analyte-specific signals, a reader/writer specially designed for quality control purposes in CD manufacture was used in Examples 2 and 3; this device detects and tracks the wobble without obligate pulsing of the laser at the energies required for disk writing.

Signal Processing

In Example 3, described briefly above and in detail below, the analogue HF signal was fed to a digital oscilloscope to generate the real-time tracings shown in FIGS. 13–18. In contrast, the data in FIG. 40 were first acquired, digitized, stored on computer magnetic disk, and only thereafter displayed on a computer monitor by appropriate interpretive software.

Multiple Data Layer Analyte-Specific Assay Discs

A second series of embodiments of the present invention takes advantage of the multiple data layer features specified in the recently-developed Digital Versatile Disc (DVD) format. As discussed in detail below, the DVD format is particularly well-suited to providing optical disc geometries and tracking schemes that permit disc tracking signals to be acquired concurrently with and discriminated from signals generated by analyte-specific signal elements.

Figure 24:
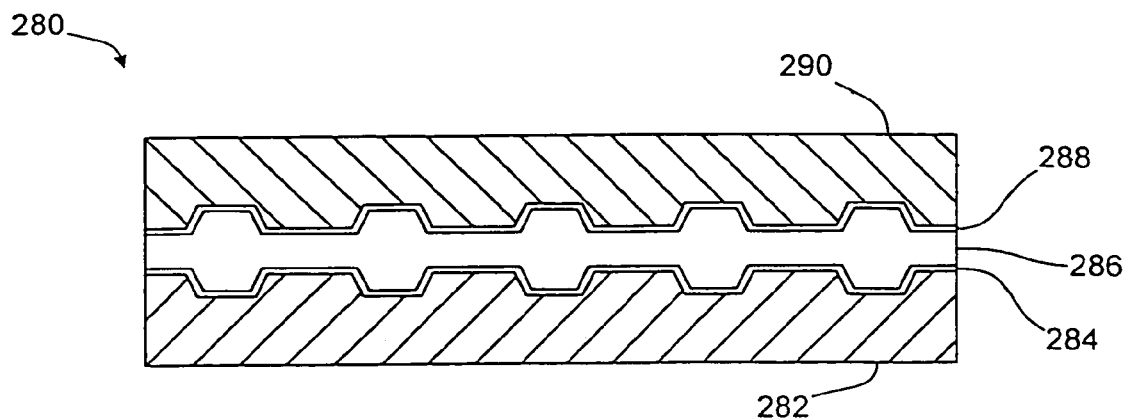
FIG. 24 shows a side cross-sectional view of a typical dual layer DVD format disc.

Referring now to FIG. 24, a side cross-sectional view of a typical dual layer DVD format disc is shown. By convention herein, laser light is incident from below. Disc 280 comprises laser-proximal substrate 282, semi-reflective layer 284, spacer layer 286, reflective layer 288, and laser-distal substrate 290.

Proximal substrate 282 comprises a transparent optical material, such as polycarbonate, having an index of refraction chosen to assist in focusing a laser beam onto either one of the two layers of data. Proximal substrate 282 may be manufactured by an injection molding process similar to the process described above for manufacturing CD-Recordable format discs. Proximal substrate 282 is typically embossed with data arranged along a spiral track. These data are typically referred to as residing in "layer 0" of a two layer disc.

The data-bearing surface of proximal substrate 282 is coated with semi-reflective layer 284. Semi-reflective layer 284 comprises a very thin coating of a material such as silicon, gold, aluminum, silver or copper that reflects some light and transmits some light. Semi-reflective layer 284 typically has a reflectivity of approximately 30%, although a range of reflectivity may be accommodated. Thus, semi-reflective layer 284 may have a reflectivity of about 20%–40%, more preferably 25%–35%, most preferably about 30%.

Distal substrate 290 comprises a material such as polycarbonate that can be molded with a spiral data track. Since the laser beam will not pass through distal substrate 290, its optical characteristics are unimportant. Distal substrate 290 may be manufactured by an injection molding process, such as described herein above.

Distal substrate 290 is embossed with data in a spiral data track that may run parallel with the spiral data track of layer 0 (i.e., from the inner portion of the disc to the outer portion), or in the opposite direction of the spiral data track of layer 0 (i.e., from the outer portion of the disc to the inner). The data embossed in distal substrate 290 is referred to as residing in "layer 1" of the two layer disc.

The data-bearing surface of distal substrate 290 is coated with reflective layer 288, which may comprise a thin layer of any reflective material, such as gold, aluminum, silver, or copper. Reflective layer 288 typically has a reflectivity that is designed to be as close as possible to the reflectivity of layer 0. This is done to obviate readjustment by the automatic gain control when switching reading from one to the other layer; such changes in the gain may adversely affect tracking. For this reason, layer 1 of a dual layer disc most often has a reflectivity far lower than 70%.

Spacer layer 286 provides 40 to 70 microns of space between layer 0 and layer 1 of the two layer disc, and also serves to bind proximal substrate 282 and semi-reflective layer 284 to distal substrate 290 and reflective layer 288. Spacer layer 286 typically comprises an optical adhesive having an index of refraction that is close to the index of refraction of the material from which proximal substrate 282 is manufactured.

In use, a DVD reader can focus its laser either on semi-reflective layer 284, to read the data in layer 0, or on reflective layer 288, to read the data in layer 1. The multi-layer nature of DVD discs and the concomitant dual-focus of DVD readers make DVD particularly well-suited for use in the present invention: the plane occupied by the operational features of the disc may, in these embodiments, be segregated physically from the plane occupied by analyte-specific elements, facilitating concurrent discriminable acquisition of both types of data.

Thus, in one embodiment, analyte-specific signal elements are placed confocally with data layer 0; the disc's tracking and other operational features are positioned at data layer 1. In another embodiment, conversely, analyte-specific signal elements are placed confocally with data layer 1, and the disc's tracking and other operational features are positioned at data layer 0. In yet another alternative, assay elements are disposed in spacer layer 286, substantially confocal with either of the two data layers.

Figure 25:
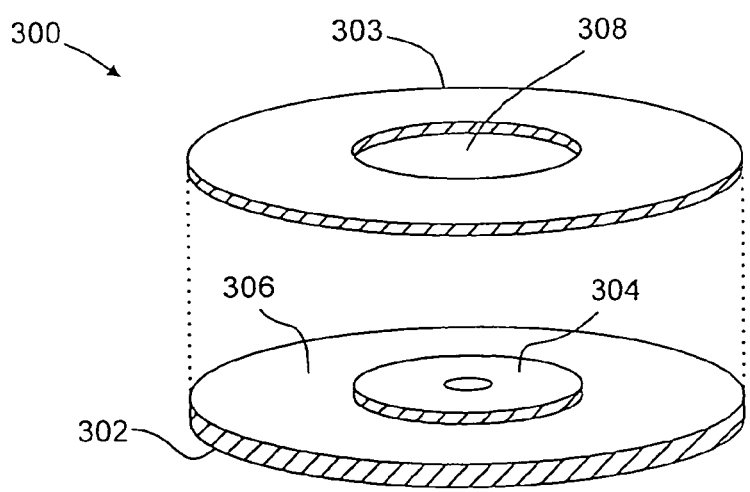
FIG. 25 shows an exploded side perspective view of an assemblable dual data layer analyte-specific assay disc.

Several of these principles are demonstrated by reference to a preferred embodiment, shown in FIG. 25. FIG. 25 presents an exploded side perspective view of DVD-type dual data layer assay disc 300. The disc disassembles substantially along the plane that is defined in a typical dual layer DVD disc by spacer layer 286.

Disc 300 comprises two portions: main portion 302 and cover portion 303. The portions may be permanently affixed to one another, may be separate and assemblable, or may be separate and reversibly assemblable. In any of these configurations, prior to reading of the disc the cover portion 303 is assembled over outer assay area 306 of main portion 302. Opening 308 and area 304 are so dimensioned as to permit a snug and reliable fit of the two pieces.

Outer assay area 306 of main portion 302 comprises a single data layer area upon which are disposed analyte-specific signal elements. Analogously to the single data layer embodiments presented herein above, outer assay area 306 is embossed with a wobble groove (not shown), or other substantially radial plane tracking features, for use in providing tracking information to an optical disc reader. Pursuant to DVD standards, and in contrast to the single-layer embodiments presented above, the wobble groove may be either a forward image or reverse image groove. As mentioned, a ZCLV format may be used.

Main portion 302 also comprises inner data area 304. Inner data area 304 is formatted in a manner similar to any normal dual layer DVD disc. Programs and data may be stored on layer 0 and/or layer 1 of this area of the disc.

In particular, inner data area 304 preferably contains instructions that direct the optical disc reader to adjust its focus to the correct data layer to read the analyte-specific signals present in assay area 306. Furthermore, inner data area 304 may store data used to adjust the firmware or "flash" components of the drive chipset, as needed to permit the drive correctly to read and interpret the analyte-specific signals.

Cover portion 303 preferably comprises a transparent optical material, such as polycarbonate, polymethyl acrylic, or glass, selected so as to optimize the detection of the operational features (e.g. the wobble groove) of disc 300, as well as the detection of the signal elements.

As will be apparent, variations well within the skill in the art include disposing the analyte-specific signal elements at either layer 0 or layer 1 in area 306, or at both such layers, segregating tracking features physically from the assay plane, which may itself lack tracking features, or combinations thereof. Further, the assay may be performed on cover portion 303, by depositing the signal elements on the laser-distal surface of cover portion 303 before assembly of the disc.

It will be apparent to one skilled in the art that there are many minor variations that could be made in this embodiment. For example, if large amounts of data or programming are needed to interpret the results of an assay, inner data area 304 could have data written both on layer 0 and on layer 1, without altering the wobble groove and assay results (i.e., signal elements) of layer 0 of outer assay area 306.

Figure 26:
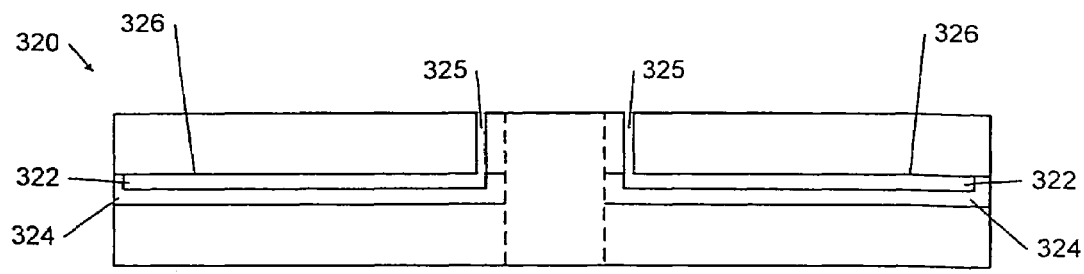
FIG. 26 shows a side cross-sectional view of a dual layer analyte-specific assay disc embodiment containing internal channels.

Another set of advantages of the multi-layer DVD format may be seen by reference to FIG. 26, a side cross-sectional view of another multi-layer embodiment of an assay disc built in accordance with the present invention. By convention herein, laser light is incident from below.

Disc 320 comprises channels 322 located in spacer layer 324. Assays may be performed by introducing materials to be tested into channels 322 through openings 325 that lie on the laser-distal side of the disc. When the assay is performed, signal elements are deposited on reflective layer 326 of layer 1 of disc 320.

Layer 1 of disc 320 is embossed with a wobble groove, providing the minimal operational needs of an optical disc reader. Layer 0 of disc 320 contains data and programming necessary to read the assay disc, and to interpret the results.

As will be apparent to one skilled in the art, multiple assays may be performed on a single disc by using multiple separate channels 322, each designed to handle a different assay. Additionally, it will be apparent that the location of channels 322 within spacer layer 324 may vary. For example, channel 322 could be adjacent to layer 0 instead of layer 1, or could be roughly centered within spacer layer 324. In either of these cases, the signal elements that are placed within channels 322 as a result of performing an assay may be detected in the return path of a laser focused on the operational features present in layer 1 of disc 320.

Co-owned and copending application Ser. No. 09/064,636, filed Apr. 21, 1998, incorporated herein by reference, describes various channeled and other three dimensional assay disc variants.

Figure 27:
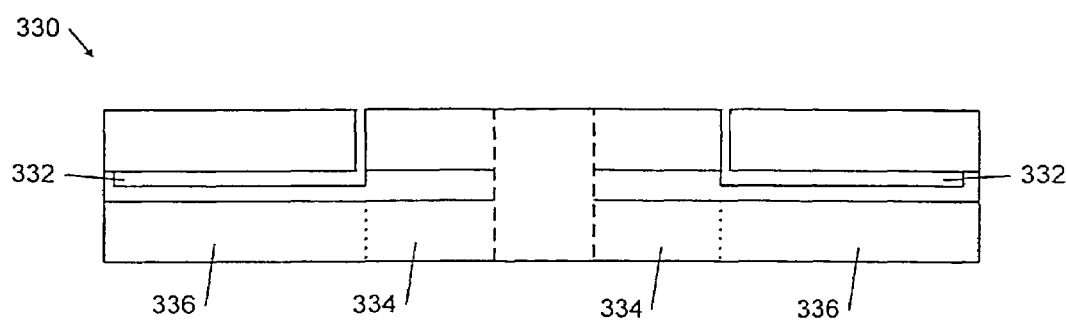
FIG. 27 shows a side cross-sectional view of a dual layer analyte-specific assay disc with internal assay-facilitating features.

FIG. 27 shows a side cross-sectional view of an assay disc similar to disc 320 of FIG. 26. Laser light would be incident from below. In disc 330 of FIG. 27, channels 332 are located towards the outer portion of the disc, leaving a central portion of disc 330 as a "standard" two layer disc. Layer 0 of disc 330 is divided into two sections. Section 334 of layer 0 stores data or programs, as described hereinabove. Section 336 of layer 0 comprises a transparent material having optical properties that may be different from the optical properties of section 334. In a preferred embodiment, the optical properties of section 336 of layer 0 are optimized for focusing a laser beam onto the operational features of the disc, and for detecting the signal elements in channels 332.

Figure 28:
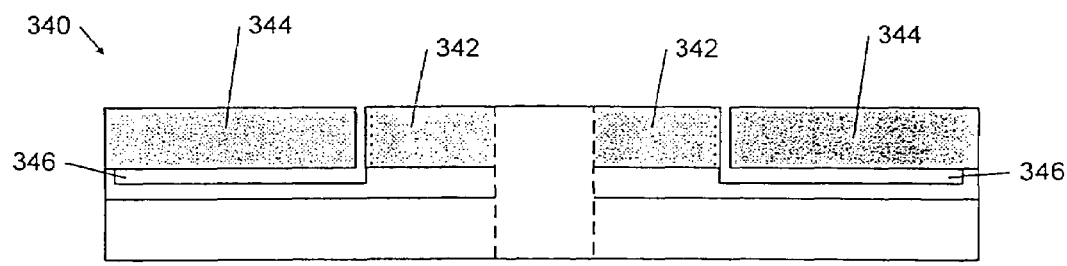
FIG. 28 shows a side cross-sectional view of yet another dual-layer analyte-specific assay disc of the present invention.

Referring to FIG. 28, another dual layer embodiment of an assay disc built in accordance with the principles of the present invention is shown in similar side cross-sectional view. Disc 340 is usable in either a DVD reader, or in a CD-Recordable reader. Layer 0 of disc 340 is arranged according to the DVD format. Data encoded on layer 0 of disc 340 may be read by a standard DVD player. Layer 1 of disc 340 is encoded according to the CD-Recordable format, and therefore uses a wider track pitch, and a lower density arrangement of data. Data may be encoded in central portion 342 of layer 1. Assay portion 344 of layer 1 is embossed with a wobble groove to satisfy the operational requirements of an optical disc reader, and is adjacent to channels 346, which are used for performing assays, as described hereinabove.

Figure 29:
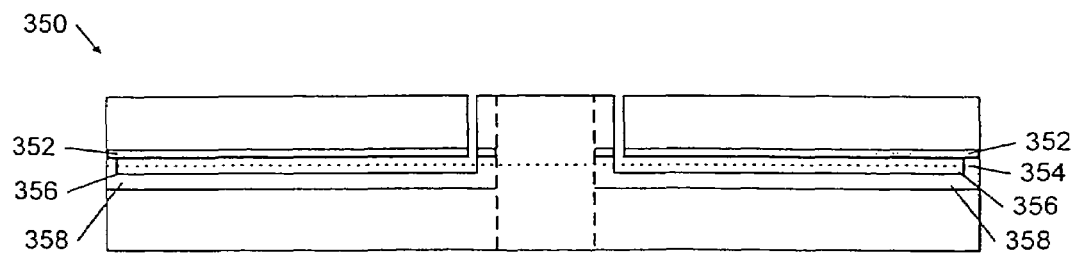
FIG. 29 shows another alternative embodiment of a two-layer analyte-specific disc.

FIG. 29 shows another alternative embodiment of a two-layer disc. On disc 350, the data and operational features of layer 1 of the two layer disc are provided by hologram 352. Hologram 352 is similar to hologram 194 of FIG. 20, so that the operational features and data encoded on hologram 352 appear to the optical disc reader to be located at image plane 354, which may be either laser distal or laser proximal relative to hologram 352. Channels 356 are used for performing assays, so the signal elements may be disposed within spacer layer 358 of disc 350. These signal elements are detectable in the return path of a laser beam that is focused on the operational features of hologram 352.

It will be apparent to one skilled in the art that a hologram similar to hologram 352 may be used to provide layer 1 in nearly any of the foregoing dual layer discs. As shown, image plane 354 is laser proximal relative to the surface of hologram 352, so the signal elements will appear to be placed directly on the surface of layer 1, or within the wobble groove that is simulated by hologram 352.

It will further be apparent to one skilled in the art that many of the foregoing embodiments shown with reference to a two layer disc could be easily extended to use in a multi-layer disc having more than two layers. For example, channels for use in performing assays could be located between each of the layers of a multi layer disc, with each of the layers (except layer 0) providing any operational features needed by the optical disc reader.

The following examples are offered by way of illustration and not by way of limitation.

EXAMPLE 1

Manufacture of a Trackable, Reverse-Image Wobble Groove Optical Disc Suitable for Analyte-Specific Assay An unpunched father part containing an image of a CD-R format wobble groove, manufactured by Cinram (Anaheim, Calif.), was matrixed to form a CD-R mother part by standard procedures. Briefly, the electroforming was performed in a nickel sulfamate bath in an electroforming system manufactured by Digital Matrix, Inc. (Hempstead, N.Y.).

The mother part was cleaned, polished and punched, then used directly as a stamper to manufacture discs having a reverse image spiral groove. A NETSTAL molding machine, manufactured by Netstal Machinery Ltd. (Naefels, Switzerland), and a CD-R mold created by AWM, of Switzerland were used to generate the discs at EXIMPO S. R. O. (Prague, Czech Republic). The molding parameters of the injection molding machine were adjusted to facilitate high venting in the mold, to accurately reproduce a groove. The polycarbonate used to mold the discs was produced by Bayer Plastics.

Polycarbonate discs with the reverse image wobble groove were then metalized with gold, using a metalizer manufactured by First Light Technologies (Saco, Me.).

As shown in the AFM measurements of FIGS. 10–12, the groove depth of these disks was approximately 170 nm with a track pitch of approximately 1.6 $\mu$m.

EXAMPLE 2

Construction of An IgG-Specific Immunoassay Site on A Trackable Optical Disc

A single data layer, first surface reverse-image wobble disc was manufactured according to Example 1. The gold surface of the disc was then derivatized as follows to construct an assay site specific for and capable of detecting human IgG in a blood sample.

An aliquot of 2 mg of N-[6-(biotinamido)hexyl]-3'-(2'-pyridyldithio)propionamide ("Biotin-HPDP") (Pierce, Rockford, Ill.; lot number 97032461) was dissolved in 2 ml of dimethylformamide. Onto each of four intended assay sites, each located at the same radius from the center of the disc, 10 $\mu$l of biotin-HPDP solution was pipetted. The disc was incubated for 2 hours at room temperature, and then washed with 50 mM phosphate buffer (pH 7).

Next, 10 $\mu$l of streptavidin solution (Monobind, Costa Mesa, Calif.; Lot 96–001/MF; 2 mg/ml) was pipetted onto the same assay spots. The disc was incubated one hour at RT, and then washed with 50 mM phosphate buffer.

Biotinylated goat anti-human IgG was obtained from Chemicon International, Inc. (Temecula, Calif.; affinity purified, lot 47797017). An aliquot of 5 $\mu$l was pipetted onto each of the four assay sites. The disc was incubated one hour at RT, then washed with 50 mM phosphate buffer (pH 7).

The geometry of the completed assay site is schematized in FIG. 7A. Biotin-HPDP 70 forms the first molecular layer above the disk surface, bonded to the disk's gold surface (Au) by a gold-sulfur dative (coordinate) bond. Streptavidin, 72, each molecule of which can bind four molecules of biotin at high affinity, forms the next layer. Biotinylated goat anti-human IgG 76, which confers analyte specificity upon the assay site, is then bound to the immobilized streptavidin 72 by its biotin moiety 74. The goat anti-human IgG is biotinylated at a location that permits its immobilization without interfering with antigen (human IgG) binding.

The disc, as so derivatized, was then used to assay for the presence of IgG in human blood.

A 100 µl sample of human blood was drawn from a normal volunteer. A 10 µl aliquot of the blood sample was diluted 10-fold using phosphate-buffered saline ("PBS"). Two further 1:10 serial dilutions in PBS were identically performed. A ten microliter (10 µl) aliquot of each one of the samples—that is, an aliquot of undiluted blood and an aliquot of each of the three serially-diluted blood samples—was separately and individually placed on one of the four disc assay sites.

The disc was incubated under nitrogen in a closed humidified chamber for 2 hrs at room temperature. The disc was then washed with PBS.

To develop the IgG-specific assay, that is, to render it suitable to report the presence of IgG in an applied sample, 5 µl (160 µg) of MagaBeads™ goat anti-human IgG (F$_c$) (Cortex Biochem, Inc., San Leandro, Calif.; lot 7A2201A) was spotted onto each of the four assay sites, and the disc incubated for 4 hours in a closed chamber. The disc was washed with 50 mM phosphate buffer (pH 7) and then with distilled water.

Figure 7B:
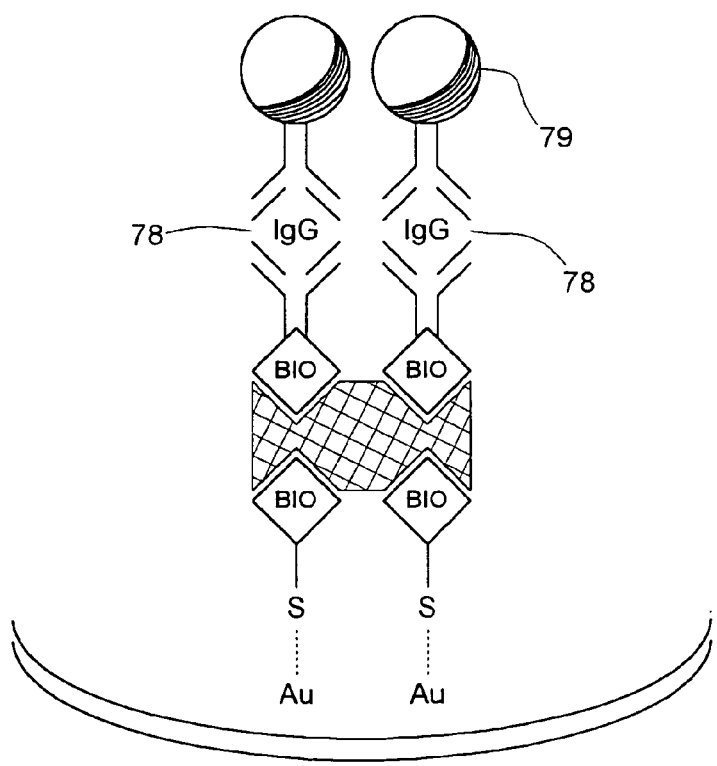

The geometry of the assay site after capture of IgG from blood and development with anti-human IgG MagaBeads™ is schematized in FIG. 7B. IgG 78 that had been present in the blood sample (the analyte) is bound by the biotinylated anti-human IgG 76 immobilized at the assay site. The human IgG 78 then serves further to immobilize the anti-IgG Magabeads™79. Magabeads™ are spherical latex magnetizable particles that are available commercially—either preconjugated with a variety of binding moieties, such as goat anti-human IgG as here, or alternatively with reactive groups that permit custom conjugation.

The disc was dried, and its surface then visualized by light and atomic force microscopy (AFM). FIG. 8 is a video image captured from a light microscopic examination of a portion of the IgG-specific first surface analyte-specific trackable assay disc after application of human blood and antibody-conjugated spheres. FIGS. 9 and 10 are AFM images of a single latex sphere immunospecifically adherent to the disk, at somewhat higher magnification than that used in FIG. 8, with summaries quantitating dimensions observed by the AFM during image acquisition. FIG. 11 is an atomic force microscope image of two latex spheres immunospecifically adherent to a first-surface trackable human IgG-specific disc and present in the same AFM field, with summary quantitating dimensions observed by the AFM during image acquisition.

EXAMPLE 3

Electronic Detection and Characterization of Human Erythrocytes on an RBC-Specific Trackable Immunoassay Optical Disk A single data layer, first surface reverse-image wobble disc was manufactured according to Example 1. The gold surface of the disk was then derivatized as follows.

An aliquot of 2 mg of N-[6-(biotinamido)hexyl]-3'-(2'-pyridyldithio)propionamide ("Biotin-HPDP") (Pierce, Rockford, Ill.; lot number 97032461) was dissolved in 2 ml of dimethylformamide. Onto each of four intended assay sites, each located at the same radius from the center of the disc, 10 µl of biotin-HPDP solution was pipetted. The disc was incubated for 2 hours at room temperature, and then washed with 50 mM phosphate buffer (pH 7).

Next, 10 µl of streptavidin solution (Monobind, Costa Mesa, Calif.; Lot 96-001/MF; 2 mg/ml) was pipetted onto the same assay spots. The disc was incubated one hour at RT, and then washed with 50 mM phosphate buffer.

Monoclonal mouse anti-human glycophorin A antibody (Dako Co., Carpinteria, Calif.; lot 113) was biotinylated as follows. A 100 µl aliquot of antibody was mixed with 0.1 mg of a-Biotin, α-N-hydroxysuccinimidyl ester of poly(ethylene glycol)-carbonate ("Bio-PEG-NHS") (Shearwater Polymers, Inc. Huntsville, Ala.; lot PT-028-27) in 100 µl of phosphate buffer (pH 7) and allowed to react for 1 hour. The biotin-conjugated anti-human glycophorin A was dialyzed overnight against the same buffer (dialysis MWCO=30,000).

The dialyzed biotin-conjugated anti-human glycophorin A antibody was pipetted onto the streptavidin-coated assay spots on the disc and the disc was then incubated for 1 hour at room temperature, followed by wash using 50 mM phosphate buffer (pH 7).

The disc, as so derivatized, was then used to assay for the presence of red blood cells in human blood.

A 100 µl sample of human blood was drawn from a normal volunteer. A 10 µl aliquot of the blood sample was diluted 10-fold using phosphate-buffered saline ("PBS"). Two further 1:10 serial dilutions were identically performed. An aliquot of 10 µl undiluted blood, and a 10 µl aliquot of each of the serially diluted samples was placed individually on the four disc assay sites.

The disc was incubated under nitrogen in a closed humidified chamber for 2 hrs at room temperature. The disc was then washed with PBS.

FIG. 12 is an atomic force microscopic image confirming the immunospecific adherence of RBCs to the assay site of the disc. As noted in the quantitative analysis, the RBC's horizontal size is given as 7.984 µm, in agreement with the known diameter of red blood cells (8 µm); this size is clearly different from the uniform 3 µm diameter of the latex spheres used and observed in Example 2. The height of the RBC above the bottom of a groove is observed to be 1.8 µm.

The disc was washed with a 5% solution of glycerol, dried, and read in the CD-drive as follows.

A CD-R device manufactured for quality control use in the optical disc industry by CD Associates, Inc. (Irvine, Calif.) was used to read the disc. The drive's CD-R wobble tracking system (model RSL100, was modified by addition of a lens 17 to the optical pickup 10 to adjust focus in the absence of a first refractive layer on the disc; the height of the spindle was also raised. The HF (RF, quad sum) signal was amplified by the electronic circuitry in the RSL100, and the buffered HF signal input to a digital oscilloscope.

FIG. 13 presents a representative tracing, with the X axis displaying time and the Y axis displaying the magnitude of the quad sum signal. FIG. 13 demonstrates that the red blood cell is directly visible as a high frequency, high amplitude event in the HF signal of a CD-R reader; for an analyte the size of a mammalian cell, no latex sphere or other exogenous signaling moiety is required to generate an analyte-specific signal.

Also evident from the oscilloscope tracing in FIG. 13 is that the deviation from the HF baseline is a double peak. Although red blood cells are well known to have a characteristic biconcave shape, we have observed this dual peak when latex spheres are used, as in Example 2, to report the presence of analytes. The dual peak appears to result from reproducible changes in reflectance as the laser traverses a sphere in the groove.

A further observation readily apparent from the oscilloscope tracing in FIG. 13 is that the baseline on either side of the signaling event is steady; that is, tracking of the wobble groove (here manufactured as an inverse image wobble groove) does not itself cause significant change in the quad sum signal.

The optical reader, in accordance with CD-R standard, maintained a constant linear velocity irrespective of the location being read on the disc, modifying spindle speed to lock a constant wobble frequency. Based upon the known linear velocity of the disc and the time increments marked on the oscilloscope tracing, each division on the oscilloscope tracing may be shown to correspond to a linear distance on the disc of 13 $\mu$m. As measured on the tracing shown in FIG. 13, the deviation in the quad sum signal baseline thus gives 10 $\mu$m as the approximate uncorrected size of the object in the direction of the tracking groove.

The actual size of the object is smaller. Prior calibration of the reader and oscilloscope using 3 $\mu$m latex spheres had given oscilloscope peaks reporting an apparent size of 5 $\mu$m, 2 $\mu$m wider than the actual object. This likely is accounted for by the 1.5 $\mu$m laser focus diameter at the first surface of the assay disc.

Taking into account the 2 $\mu$m difference between measured and actual size occasioned by the diameter of the laser at the disc surface, the event captured on the oscilloscope tracing in FIG. 13 as a high frequency, high amplitude deviation in quad sum signal reports an object size of 8 $\mu$m, in excellent agreement with the known 8 $\mu$m diameter of a human erythrocyte.

FIG. 14 presents another oscilloscope tracing of the HF event signaled by detection of a separate red cell on the same disc. The biphasic peak is more pronounced. FIGS. 15–17 are additional examples.

FIG. 18 is a digital superimposition of multiple events acquired from various areas of the same disc, demonstrating the reproducibility of the size and shape measurements over several different red blood cells immunospecifically adherent to the disc.

EXAMPLE 4

Calculation of Optimal Signal Element Sizes

Analyte-specific signals may be optimized by adjusting the size of spherical signal elements relative to the size of the tracking groove, as follows.

Figure 30:
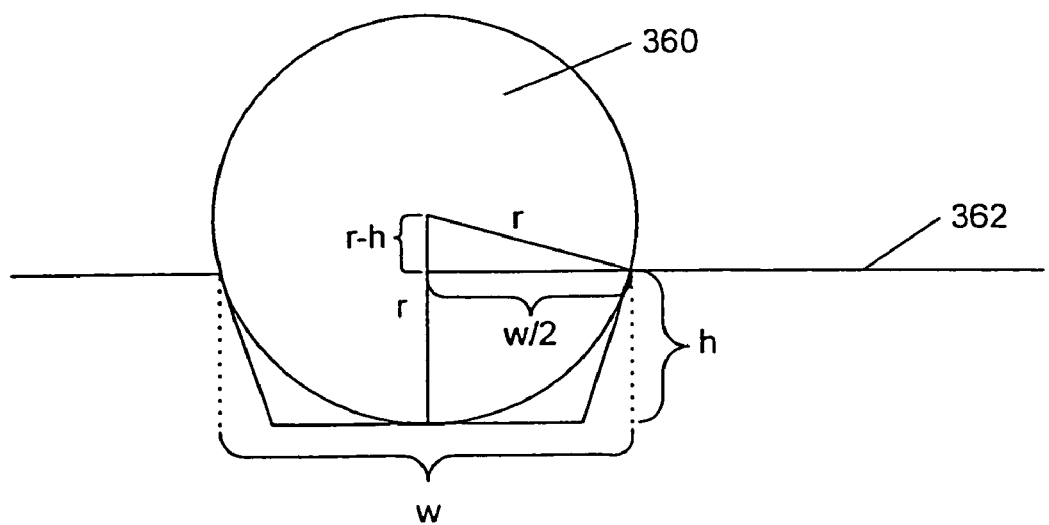
FIG. 30 shows a side cross-sectional view of a spherical signal in a moiety engaged in a disc groove, with various dimensions labeled.

FIG. 30 illustrates a calculation of the size for a spherical signal element 360 to fit into a groove on disc 362 such that the signal element is bound to the groove at three points: one point at the bottom of the groove, and a point at each edge of the groove. In the following formulae, r is the radius of the spherical signal element, w is the width of the groove, and h is the depth of the groove.

By the Pythagorean theorem, the relationship between the radius of the sphere and the width and depth of the groove is:

$$r^2 = (r-h)^2 + \left(\frac{w}{2}\right)^2 \tag{1}$$

Solving for r yields:

$$r = \frac{4h^2 + w^2}{8h} \tag{2}$$

Since the depth of a groove is preferably $\lambda/8$, where $\lambda$ is the wavelength of light used to read the disc, we can express the radius as:

$$r = \frac{4\frac{\lambda^2}{64} + w^2}{\lambda} \tag{3}$$

Simplifying this yields:

$$r = \frac{\lambda}{16} + \frac{w^2}{\lambda} \tag{4}$$

Applying equation (4), if the wavelength of the light used to read the disc is 0.65 $\mu$m (i.e., 650 nm, which is used for DVD), and the groove width is 0.8 $\mu$m (the track pitch for DVD), then the radius of the spherical signal elements should be approximately 1.03 $\mu$m.

EXAMPLE 5

Manufacture of Single Data Layer Optical Discs with Reverse Image Wobble Groove Optimized For First Surface Detection A CD-R mother part was fabricated to order at CINRAM, essentially as set forth in Example 1, to serve directly as a stamper to produce trackable, single data-layer, reverse image wobble groove disks. The mother part was used to stamp about 5000 polycarbonate disks, which were then metalized with gold and stored for subsequent use. The disk molding was performed at EXIMPO S. R. O. (Prague, Czech Republic). Mold settings are set forth in FIGS. 41A–41I.

The disks fabricated in Example 1 (and used in Examples 2 and 3 to generate the data presented in FIGS. 8–18), had groove depths of approximately 170 nm, reported as "vertical distance" in the dimensional summary provided by atomic force microscope, reproduced in FIG. 10. The disks manufactured here, by contrast, were designed with groove depths approximating the first surface theoretical optimum of ⅛ the 780 nm wavelength of the intended incident laser.

Figure 33:
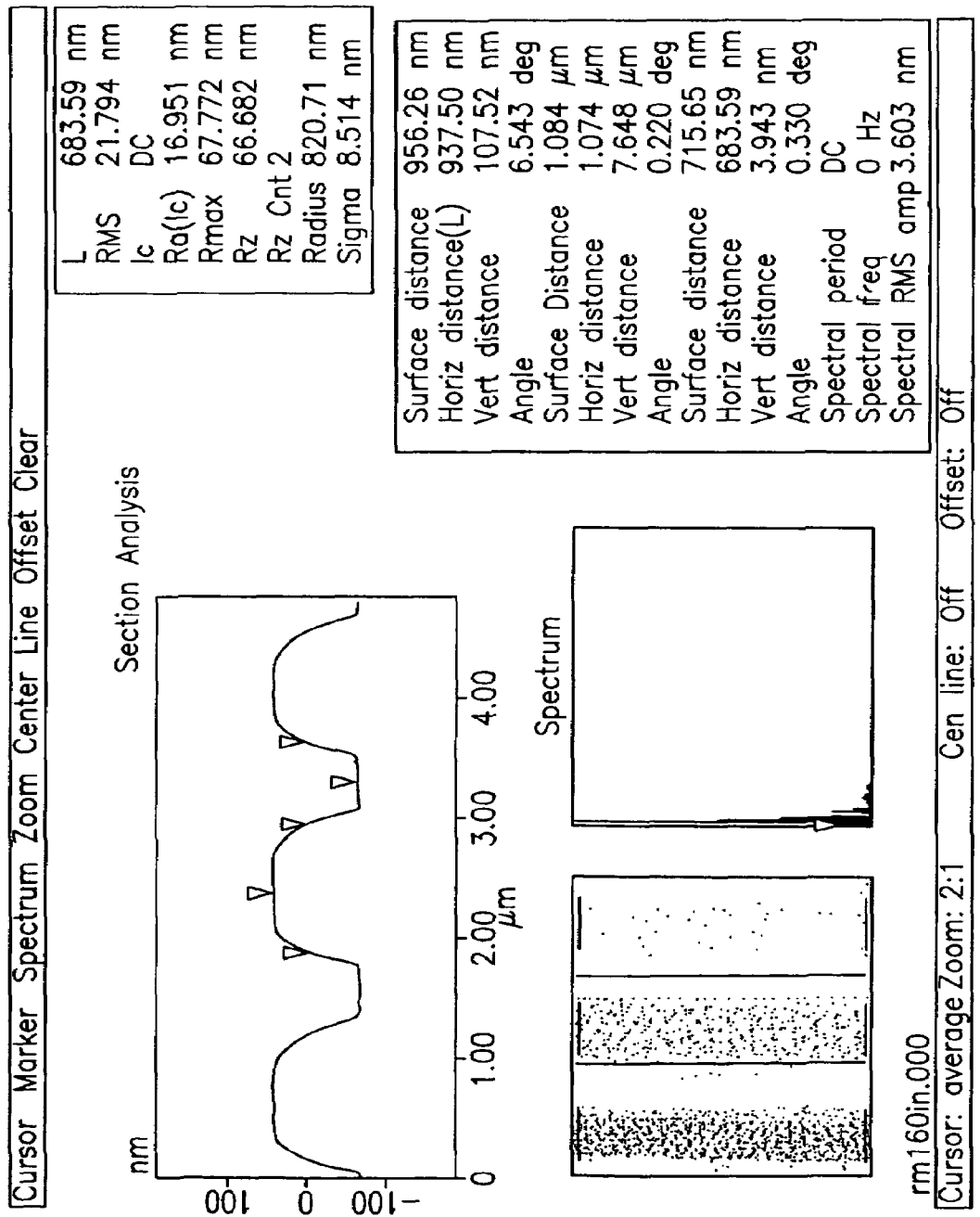
FIG. 33 presents data from atomic force microscopic examination of the inner diameter of the "mother" part used to stamp the disks measured in FIGS. 32 and 33.
Figure 34:
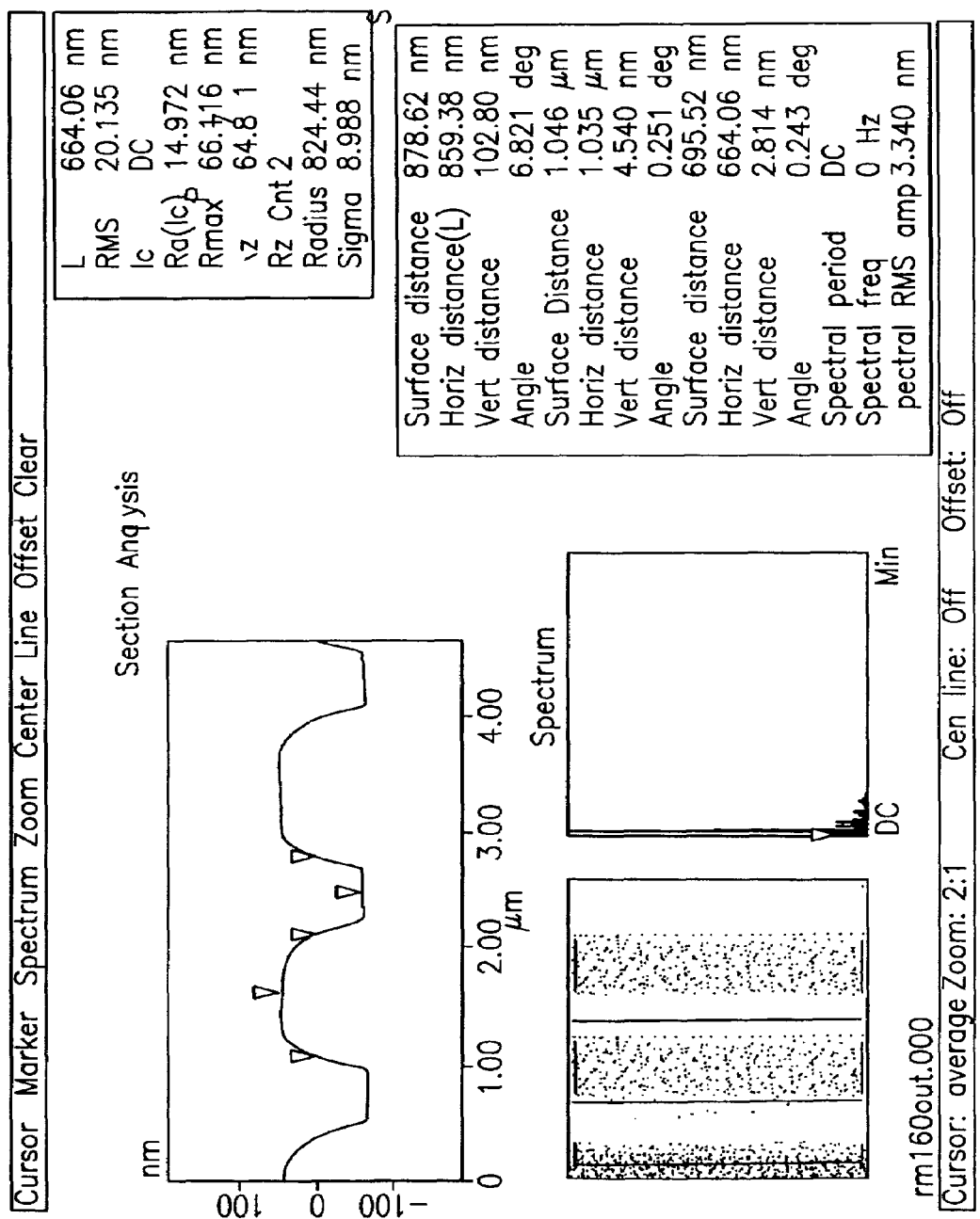
FIG. 34 presents data from atomic force microscopic examination of the outer diameter of the "mother" part used to stamp the disks measured in FIGS. 32 and 33.

FIG. 31 presents data from atomic force microscopic examination of the inner diameter of one of the disks. The dimensional summary reports a groove depth of approximately 100 nm. FIG. 32 presents similar data from atomic force microscopic examination of the outer diameter; as is typical of disk manufacture, the groove depth is slightly greater at the outer diameter (here, 101.23 nm), to accommodate the somewhat increased travel of the outer portion of the disk in the direction of the optical axis. FIG. 33 presents analogous data from atomic force microscopic examination of the inner diameter of the mother part, and FIG. 34 presents data from atomic force microscopic examination of the outer diameter of the mother part.

Also evident in the AFM measurements is that the groove was designed, within the limits imposed by the 1.6 $\mu$m spiral track pitch, to be wider than the lands; this was done to encourage analyte-specific elements—e.g., beads, cells, or other micron-sized elements—to fall into the groove, providing the maximal electronic response. Dimensioning the signal elements according to Example 4 would provide still further increase in signal.

EXAMPLE 6

Manufacture of Laser-Refracting Polycarbonate Covers

Figure 35:
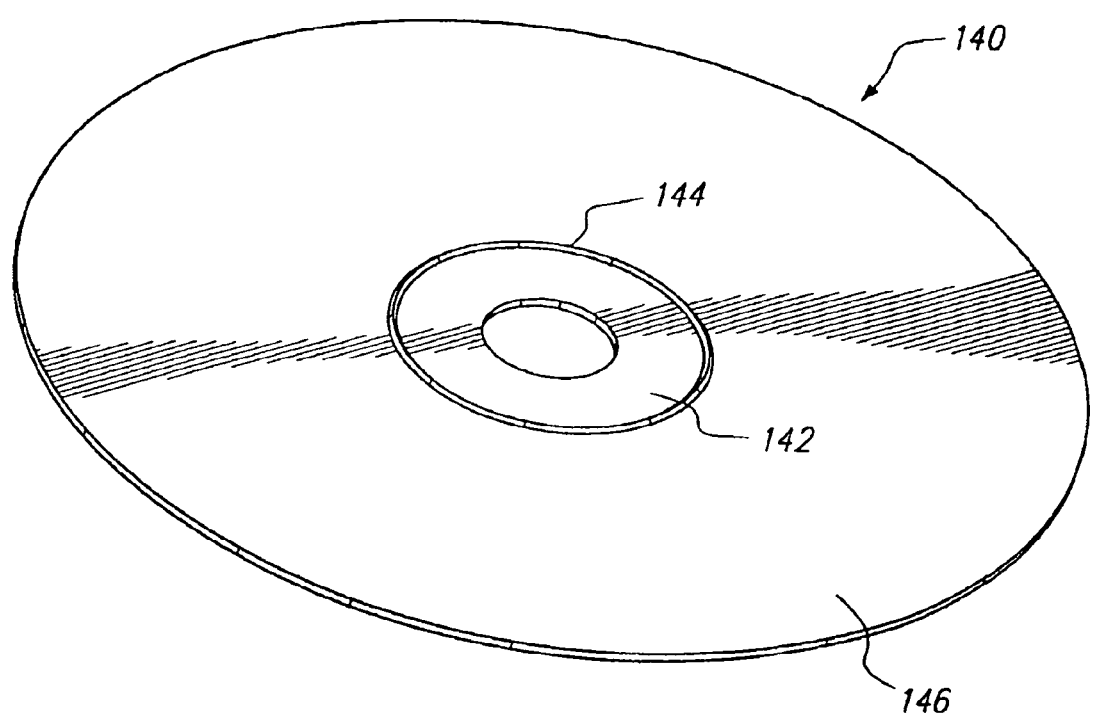
FIG. 35 is a top perspective view of a polycarbonate laser-refracting cover, as used with the disks of FIGS. 31 and 32 to generate the data shown in FIG. 40.

Laser refracting polycarbonate covers, one of which is shown in top perspective view in FIG. 35 and further schematized in FIG. 19 in side sectional view (as assembled to a single data layer analyte-specific disk), were manufactured as follows.

A nickel disk stamper intended for manufacture of a standard CD, but too thick for effective mounting on a molding machine, was placed in a standard stamper polisher. The data surface of the stamper was polished to smoothness, producing a stamper about 260 μm–330 μm thick with two polished faces. The stamper was mounted in a standard CD-R mold and settings were adjusted to give a polycarbonate cover approximately 1.17 mm thick, but otherwise dimensioned identically to a standard 120 mm disk.

The single data layer disks manufactured in Example 5 are about 1.2+/−0.05 mm thick; the cover is about 1.17 mm thick. Together, the two create an assembly that is approximately 2.4 mm thick, outside the maximal physical thickness provided by Red Book standard (1.1–1.5 mm for all layers combined). Empirically, we found that the increased thickness of the disk assembly presented neither optical nor mechanical problems. The data presented in FIG. 40 were obtained using disks manufactured according to Example 5 and assembled, before reading, with a cover manufactured in accordance with this Example. The cover provided sufficient assistance to focusing to obviate addition of a further focusing lens 17 to the drive's optical pickup.

EXAMPLE 7

High Sensitivity Nucleic Acid Sequence-Driven Adherence of Signal Elements to Trackable Optical Disks Single data layer, first surface reverse-image wobble discs were manufactured according to Example 5. The gold surface of the disks was then derivatized as follows. Manipulations were performed in a laminar flow hood in a clean room.

On each of six disks was placed a single spot of 15 μL streptavidin solution (2 mg/mL). The disks were incubated 1 hour, then rinsed in a stream of distilled $H_2O$ ($dH_2O$). An aliquot of 10 μL 2-mercaptoethylamine (137 μg/mL) was added to each spot to block non-specific binding (the solution had been stored at 4° C. for a time sufficient to oxidize the solution). The disks were incubated for 3 minutes, then rinsed with $dH_2O$. The disks were not dried before use.

Nucleic acid probes were synthesized to order by Keystone Laboratories (Foster City, Calif.) with amine-modified 3' or 5' termini as follows:

```
5'-TCGGGTGTACTCAC-amine-3'       (SEQ ID NO:1)
```

-continued
```
5'-amine-TCCAAGAAAGGACC-3'       (SEQ ID NO:2)
```

Each probe was then independently conjugated to biotin through its amine-modified terminus as follows.

A stock solution of biotin-PEG-NHS (α-Biotin, ω-N-hydroxysuccinimidyl ester of polyethylene glycol)-carbonate) (MW=3400, Shearwater Polymers, Inc. Huntsville, Ala.; lot PT-028-27) was prepared by dissolving solid in phosphate buffered saline containing azide as a preservative (PBSAz, pH 7.45) to a final concentration of 23.5 nmol/μL (4.7 mg biotin-PEG-NHS in 58.82 μL).

The 3' aminated probe (SEQ ID NO:1) ("3' probe") was dissolved in PBSAz to a final concentration of 1 nmol/μL (473 nmol in 473 μL). Twenty μL (20 mol) of the 3' probe solution was then added to 10 μL biotin-PEG-NHS stock solution to yield a final nucleic acid concentration of 660 pmol/μL. In parallel, the 5' aminated probe (SEQ ID NO:2) ("0.5° probe") was dissolved in PBSAz to a final concentration of 2 nmol/μL (84 nmol in 42 μL), and 10 μL (20 nmol) of this 5' probe solution was then added to 10 μL biotin-PEG-NHS stock to yield a final nucleic acid concentration of 1 nmol/μL. The solutions were separately incubated at room temperature (RT) for 2 hours.

The 3' probe was then conjugated to the surface of monodispersed superparamagnetic beads (uniformly 2.8 μm in diameter) via the biotin moiety. To a 1 mg aliquot (100 μL, 10 mg/ml) of streptavidin-coated Dynabeads® (Dynal Inc., Lake Success, N.Y.; cat. no. M-280) were added ten successive 10 μL aliquots of 1:10 diluted 3' biotinylated probe prepared as above (66 pmol/μL at 1:10 dilution). A 10 minute incubation at room temperature was performed between the first and second addition of probe solution to the beads, 5 minutes between second and third, and two minutes between the remaining additions.

The 3' probe-conjugated beads were then rinsed twice with 200 μL PBSAz and 200 μL hybridization buffer (923 mM $Na_2HPO_4$, 75 mM $NaH_2PO_4$, 1 mM EDTA, pH 7.34). Beads were recovered quantitatively from the rinse solutions using magnetic separation (Dynal). The beads were resuspended in 1 mL hybridization buffer. Assuming complete conjugation of nucleic acid, the 3' probe is present in this conjugated bead solution at an average concentration of 198 fmol/μL.

The 5' biotinylated probe (20 μL at 1 nmol/μL) was diluted to 1 mL with hybridization buffer (final concentration 20 pmol/μL).

Target nucleic acid was synthesized to order by Keystone Laboratories as follows:

5'-GTGAGTACACCGGAATTGCCAGGACGAC-CGGGTCCTTTCTTGGA-3' (SEQ ID NO:3).

Target was dissolved in PBSAZ to a final concentration of 100 μM. Thereafter, four 1,000-fold (1 μL to 1 mL) serial dilutions were performed with hybridization buffer, yielding target test solutions at concentrations of 100 nM, 100 μM, 100 fM and 100 aM.

Six fluid-phase hybridization reactions were set up in parallel solutions. In each reaction, 2 μL bead-conjugated 3' probe (396 fmoles nucleic acid) and 1 μL biotinylated 5' probe (20 pmoles) were incubated with target DNA (SEQ ID NO:3) as follows:

| | |
|---|---|
| reaction 1 | 1 μL 100 nM target = 100 fmoles target |
| reaction 2 | 1 μL 100 pM target = 100 amoles target |
| reaction 3 | 1 μL 100 fM target = 100 zmoles target |
| reaction 4 | 1 μL 100 aM target = 100 ymoles target |
| reaction 5 | 1 μL hybridization buffer (control) |
| reaction 6 | 1 μL water (control) |

Each tube was incubated at room temperature for 2 hours on a shaker, 300 RPM.

After hybridization was complete, each of the six hybridization reactions was rinsed twice with 100 μL PBSAz, with the beads recovered quantitatively using magnetic separation, and resuspended in 10 μL PBSAZ. For each of the six reactions, 2 μL of bead suspension was then applied to the streptavidin assay spot on a separate one of the disks, yielding target amounts as follows:

| | |
|---|---|
| disk 1 | 20 fmoles (20 × $10^{-15}$ moles) target |
| disk 2 | 20 amoles (20 × $10^{-18}$ moles) target |
| disk 3 | 20 zmoles (20 × $10^{-21}$ moles) target |
| disk 4 | 20 ymoles (20 × $10^{-24}$ moles) target |
| disk 5 | 0 (hybridization buffer control) |
| disk 6 | 0 (water control) |

The beads were incubated 10 minutes on the disk, which was then rinsed with a stream of water. The disks were dried, then visualized by light microscopy.

FIG. 36 schematizes the assay site at the time of visualization. Directly adherent to the gold surface of the trackable optical disk is a coating of streptavidin, bound by van der Waal's forces and by sulfur-gold bonds formed between free sulfyhydryls of the streptavidin protein and the gold surface of the disk. The streptavidin captures the biotin moiety of the 5' probe. The 5' probe, in turn, captures the target nucleic sequence by Watson-Crick complementarity with 14 nucleotides at the 3' end of the target. The target, in turn, captures the 3' probe through Watson-Crick complementarity of 14 nucleotides at its 5' end, thus tethering the Dynabead® to the disk.

FIG. 37 presents light microscopic images taken separately of assay disks 1–3, each disk at two magnifications: adherent spheres and the wobble grooves are clearly visible in the higher magnification panels of all three. Increasing numbers of adherent beads are clearly seen with increasing amounts of nucleic acid target, with disk 3 (FIG. 37C) showing complementarity-driven adherence of spheres to the disk surface at 20 zeptomoles (20×$10^{-21}$ moles; 12×$10^3$ molecules) nucleic acid target, with disk 2 (FIG. 37B) showing complementarity-driven adherence of spheres to the disk surface at 20 attomoles (20×$10^{-18}$ moles; 12×$10^6$ molecules) nucleic acid target, and disk 1 (FIG. 37A) showing complementarity-driven adherence of spheres to the disk surface at 20 femtomoles (20×$10^{-15}$ moles; 12×$10^9$ molecules) of nucleic acid target. No beads were observed on the surface of either control disk (not shown).

All patents, patent publications, and other published references mentioned herein are hereby incorporated by reference in their entirety as if each had been individually and specifically incorporated by reference herein. While preferred illustrative embodiments of the present invention are described, it will be apparent to one skilled in the art that various changes and modifications may be made therein without departing from the invention, and it is intended in the appended claims to cover all such changes and modifications which fall within the true spirit and scope of the invention.

What is claimed is:

1. A trackable optical disc, comprising:
   a first reflective surface comprising a wobble groove trackable by an optical disc reader; and
   a plurality of analyte-specific signal elements disposed readably with said wobble groove, said plurality of analyte-specific signal elements arranged in a pattern to thereby function as encoded data,
   wherein said plurality of analyte-specific signal elements are disposed substantially confocally with said wobble groove such that they are readable by an optical head of the optical disc reader concurrently with said wobble groove.

2. The trackable optical disc of claim 1 wherein said plurality of analyte-specific signal elements and said wobble groove are disposed to produce a signal readable by a single optical pickup of the optical disc reader.

3. The trackable optical disc of claim 1 wherein said wobble groove is radially disposed.

4. The trackable optical disc of claim 1 wherein said plurality of analyte-specific signal elements are disposed with said wobble groove such that a signal from an analyte-specific signal element of said plurality of analyte-specific signal elements is detectable as an amplitude variation in an HF signal generated by tracking said wobble groove with a laser from an optical disc reader reading said optical disc.

5. The trackable optical disc of claim 1 further comprising a first solid substrate, said first reflective surface and said wobble groove being disposed upon the same side of said first solid substrate.

6. The trackable optical disc of claim 5 wherein said plurality of analyte-specific signal elements are disposed on said first reflective surface of said disc substrate on the side of said first reflective surface opposite of said first solid substrate.

7. The trackable optical disc of claim 5 further comprising a light transmissible coating applied to said first reflective surface opposite of said first solid substrate, wherein said plurality of analyte-specific signal elements are disposed upon said light transmissible coating on the side of the light transmissible coating opposite to said first reflective surface.

8. The trackable optical disc of claim 1 wherein said first reflective surface holographically projects a readable image of said wobble groove when illuminated.

9. The trackable optical disc of claim 1 wherein said analyte-specific signal element includes an antibody.

10. The trackable optical disc of claim 1 wherein said analyte-specific signal element includes a nucleic acid.

11. The trackable optical disc of claim 1 wherein said analyte-specific signal element is a cell.

* * * * *